United States Patent
Skerra et al.

(10) Patent No.: US 8,420,051 B2
(45) Date of Patent: Apr. 16, 2013

(54) MUTEINS OF HNGAL AND RELATED PROTEINS WITH AFFINITY FOR A GIVEN TARGET

(75) Inventors: Arne Skerra, Freising (DE); Andreas Eichinger, Unterschleissheim (DE); Hyun-Jin Kim, Seoul (KR)

(73) Assignee: Technische Universitaet Meunchen, Munich (DE)

( * ) Notice: Subject to any disclaimer, the term of this patent is extended or adjusted under 35 U.S.C. 154(b) by 0 days.

(21) Appl. No.: 12/737,240

(22) PCT Filed: Jun. 24, 2009

(86) PCT No.: PCT/EP2009/057925
§ 371 (c)(1),
(2), (4) Date: Jun. 15, 2011

(87) PCT Pub. No.: WO2009/156456
PCT Pub. Date: Dec. 30, 2009

(65) Prior Publication Data
US 2011/0262353 A1     Oct. 27, 2011

Related U.S. Application Data

(60) Provisional application No. 61/075,175, filed on Jun. 24, 2008.

(51) Int. Cl.
| | | |
|---|---|---|
| A61K 49/10 | (2006.01) | |
| A61K 38/17 | (2006.01) | |
| C12N 15/12 | (2006.01) | |
| C12N 15/63 | (2006.01) | |
| C07K 14/47 | (2006.01) | |

(52) U.S. Cl.
USPC ......... 424/1.69; 424/9.1; 424/85.1; 435/69.1; 435/320.1; 435/325; 435/252.33; 530/350; 530/391.7; 530/395; 536/23.5

(58) Field of Classification Search ........................ None
See application file for complete search history.

(56) References Cited

U.S. PATENT DOCUMENTS

| | | |
|---|---|---|
| 7,252,998 B2 | 8/2007 | Skerra et al. |
| 2006/0088908 A1 | 4/2006 | Skerra et al. |
| 2009/0042785 A1 | 2/2009 | Matschiner et al. |

FOREIGN PATENT DOCUMENTS

| | | |
|---|---|---|
| WO | WO 03/029463 A2 | 4/2003 |
| WO | WO 2006/056464 A2 | 6/2006 |

OTHER PUBLICATIONS

Kjeldsen et al, Biochimica et Biophysica Acta, 2000, vol. 1482, pp. 272-283.*
Lazar et al Mol. Cell. Biol., 1988, vol. 8, pp. 1247-1252.*
Wells, 1990, Biochemistry 29:8509-8517.*
Kaufman et al (Blood; 94: 3178-3184, 1999).*
Wang et al. (Nuc. Acids Res. 27, No. 23: 4609-4618, 1999.*
International Search Report mailed Nov. 27, 2009 in PCT/EP2009/057925, 3 pages.
Corneillie et al., "Irreversibly binding anti-metal chelate antibodies: Artificial receptors for pretargeting," Journal of Inorganic Biochemistry, May 1, 2006, 100(5-6):882-890.
Kim et al., "High-Affinity Recognition of Lanthanide(III) Chelate Complexes by a Reprogrammed Human Lipocalin 2," J. Am. Chem. Soc., Mar. 18, 2009, 131(10):3565-3576.
Skerra, Arne, "Anticalins as alternative binding proteins for therapeutic use," Current Opinion in Molecular Therapeutics, Current Drugs, Aug. 1, 2007, 9(4):336-344.

* cited by examiner

*Primary Examiner* — Bridget E Bunner
*Assistant Examiner* — Fozia Hamud
(74) *Attorney, Agent, or Firm* — Foley & Lardner LLP

(57) ABSTRACT

The present invention relates to novel muteins derived from human lipocalin 2 (hNGAL) and related proteins that bind a given non-natural ligand with detectable affinity. The invention also relates to corresponding nucleic acid molecules encoding such a mutein and to a method for their generation. The invention further relates a method for producing such a mutein. Furthermore, the invention is directed to a pharmaceutical composition comprising such a lipocalin mutein as well as to various uses of the mutein.

61 Claims, 9 Drawing Sheets

```
                             SEQUENCE LISTING

<160> NUMBER OF SEQ ID NOS: 34

<210> SEQ ID NO 1
<211> LENGTH: 178
<212> TYPE: PRT
<213> ORGANISM: Homo sapiens

<400> SEQUENCE: 1

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 2
<211> LENGTH: 178
<212> TYPE: PRT
<213> ORGANISM: Artificial
<220> FEATURE:
<223> OTHER INFORMATION: Mutein of hNGAL

<400> SEQUENCE: 2

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Gln Val Gly Arg Ala Gly Asn Ala Ala Leu Arg Glu Asp Lys Asp Pro
            35                  40                  45

Gln Lys Met Thr Ala Gln Ile Tyr Glu Leu Lys Glu Asp Lys Ser Tyr
    50                  55                  60

Asn Val Thr Ala Val Arg Phe Arg Lys Lys Lys Cys Asp Tyr Ala Ile
```

```
                65                  70                  75                  80
Met Thr Phe Val Pro Gly Ser Gln Pro Gly Glu Phe Thr Leu Gly Asn
                        85                  90                  95

Ile Lys Ser Tyr Pro Gly Leu Thr Ser Tyr Leu Val Arg Val Val Ser
                        100                 105                 110

Thr Asn Tyr Asn Gln His Ala Met Val Phe Phe Lys Lys Val Ser Gln
                        115                 120                 125

Asn Arg Glu Tyr Phe Ser Ile Thr Leu Leu Gly Arg Thr Lys Glu Leu
            130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                        165                 170                 175

Asp Gly

<210> SEQ ID NO 3
<211> LENGTH: 178
<212> TYPE: PRT
<213> ORGANISM: Artificial
<220> FEATURE:
<223> OTHER INFORMATION: Mutein of hNGAL

<400> SEQUENCE: 3

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Gln Val Gly Arg Ala Gly Asn Ala Ala Leu Arg Glu Asp Lys Asp Pro
            35                  40                  45

Gln Lys Met Thr Ala Gln Ile Tyr Glu Leu Lys Glu Asp Lys Ser Tyr
50                  55                  60

Asn Val Thr Ala Val Arg Phe Arg Lys Lys Asp Cys Asp Tyr Ala Thr
65                  70                  75                  80

Met Thr Phe Val Pro Gly Ser Gln Pro Gly Glu Phe Thr Leu Gly Asn
                        85                  90                  95

Ile Lys Ser Tyr Pro Gly Leu Thr Ser Tyr Leu Val Arg Val Val Ser
                        100                 105                 110

Thr Asn Tyr Asn Gln His Ala Met Val Phe Phe Lys Lys Val Ser Gln
                        115                 120                 125

Asn Arg Glu Tyr Phe Ser Ile Thr Leu Leu Gly Arg Thr Lys Glu Leu
            130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                        165                 170                 175

Asp Gly

<210> SEQ ID NO 4
<211> LENGTH: 178
<212> TYPE: PRT
<213> ORGANISM: Artificial
<220> FEATURE:
<223> OTHER INFORMATION: Mutein of hNGAL

<400> SEQUENCE: 4

Gln Asp Ser Thr Ser Asp Leu Ile Pro Ala Pro Pro Leu Ser Lys Val
1               5                   10                  15
```

```
Pro Leu Gln Gln Asn Phe Gln Asp Asn Gln Phe His Gly Lys Trp Tyr
            20                  25                  30

Gln Val Gly Arg Ala Gly Asn Ala Ala Leu Arg Glu Asp Lys Asp Pro
        35                  40                  45

Gln Lys Met Thr Ala Gln Ile Tyr Glu Leu Lys Glu Asp Lys Ser Tyr
    50                  55                  60

Asn Val Thr Ala Val Arg Phe Arg Lys Lys Lys Cys Asp Tyr Ala Thr
65                  70                  75                  80

Met Thr Phe Val Pro Gly Ser Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Ser Ile Thr Leu Leu Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 5
<211> LENGTH: 178
<212> TYPE: PRT
<213> ORGANISM: Artificial
<220> FEATURE:
<223> OTHER INFORMATION: Mutein of hNGAL

<400> SEQUENCE: 5

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Gln Val Gly Arg Ala Gly Asn Ala Ala Leu Arg Glu Asp Lys Asp Pro
        35                  40                  45

Gln Lys Met Thr Ala Gln Ile Tyr Glu Leu Lys Glu Asp Lys Ser Tyr
    50                  55                  60

Asn Val Thr Ala Val Arg Ser Arg Glu Lys Lys Cys Asp Tyr Ala Thr
65                  70                  75                  80

Met Thr Phe Val Pro Gly Ser Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Ser Ile Thr Leu Leu Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 6
<211> LENGTH: 178
```

<212> TYPE: PRT
<213> ORGANISM: Artificial
<220> FEATURE:
<223> OTHER INFORMATION: Mutein of hNGAL

<400> SEQUENCE: 6

Gln Asp Ser Thr Ser Asp Leu Ile Pro Ala Pro Leu Ser Lys Val
1               5                   10                  15

Pro Leu Gln Gln Asn Phe Gln Asp Asn Gln Phe His Gly Lys Trp Tyr
            20                  25                  30

Gln Val Gly Arg Ala Gly Asn Ala Ala Leu Arg Glu Asp Lys Asp Pro
        35                  40                  45

Gln Lys Met Thr Ala Gln Ile Tyr Glu Leu Lys Glu Asp Lys Ser Tyr
    50                  55                  60

Asn Val Thr Ala Val Arg Phe Arg Lys Lys Lys Cys Asp Tyr Leu Thr
65                  70                  75                  80

Met Thr Phe Val Pro Gly Ser Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Ser Ile Thr Leu Leu Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 7
<211> LENGTH: 178
<212> TYPE: PRT
<213> ORGANISM: Artificial
<220> FEATURE:
<223> OTHER INFORMATION: Mutein of hNGAL

<400> SEQUENCE: 7

Gln Asp Ser Thr Ser Asp Leu Ile Pro Ala Pro Leu Ser Lys Val
1               5                   10                  15

Pro Leu Gln Gln Asn Phe Gln Asp Asn Gln Phe His Gly Lys Trp Tyr
            20                  25                  30

Gln Val Gly Arg Ala Gly Asn Ala Ala Leu Arg Glu Asp Lys Asp Pro
        35                  40                  45

Gln Lys Met Thr Ala Gln Ile Tyr Glu Leu Lys Glu Asp Lys Ser Tyr
    50                  55                  60

Asn Val Thr Ala Val Arg Phe Arg Lys Lys Lys Cys Asp Tyr Leu Thr
65                  70                  75                  80

Met Thr Phe Val Pro Gly Ser Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Gln Gln
        115                 120                 125

Asn Arg Glu Tyr Phe Ser Ile Thr Leu Leu Gly Arg Thr Lys Glu Leu
    130                 135                 140

Ala Ser Glu Leu Lys Glu Asn Phe Ile Arg Phe Ser Lys Ser Leu Gly

```
                145                 150                 155                 160
Leu Pro Glu Asn His Ile Val Phe Pro Val Pro Ile Asp Gln Cys Ile
                    165                 170                 175

Asp Gly

<210> SEQ ID NO 8
<211> LENGTH: 178
<212> TYPE: PRT
<213> ORGANISM: Artificial
<220> FEATURE:
<223> OTHER INFORMATION: Mutein of hNGAL

<400> SEQUENCE: 8

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Gln Val Gly Arg Ala Gly Asn Ala Ala Leu Arg Glu Asp Lys Asp Pro
            35                  40                  45

Gln Lys Met Thr Ala Gln Ile Tyr Glu Leu Lys Glu Asp Lys Ser Tyr
        50                  55                  60

Asn Val Thr Ala Val Arg Phe Arg Lys Lys Lys Cys Asp Tyr Leu Thr
65                  70                  75                  80

Met Thr Phe Val Pro Gly Ser Gln Pro Gly Glu Phe Thr Leu Gly Asn
                85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Gln Gln
            115                 120                 125

Asn Arg Glu Tyr Phe Ser Ile Ser Leu Leu Gly Arg Thr Lys Glu Leu
        130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                    165                 170                 175

Asp Gly

<210> SEQ ID NO 9
<211> LENGTH: 178
<212> TYPE: PRT
<213> ORGANISM: Artificial
<220> FEATURE:
<223> OTHER INFORMATION: Mutein of hNGAL

<400> SEQUENCE: 9

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Gln Val Gly Arg Ala Gly Asn Ala Ala Leu Arg Glu Asp Lys Asp Pro
            35                  40                  45

Gln Lys Met Thr Ala Gln Ile Tyr Glu Leu Lys Glu Asp Lys Ser Tyr
        50                  55                  60

Asn Val Thr Ala Val Arg Phe Arg Lys Lys Lys Cys Glu Tyr Leu Thr
65                  70                  75                  80

Met Thr Phe Val Pro Gly Ser Gln Pro Gly Glu Phe Thr Leu Gly Asn
                85                  90                  95
```

-continued

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Gln Gln
        115                 120                 125

Asn Arg Glu Tyr Phe Ser Ile Ser Leu Leu Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 10
<211> LENGTH: 178
<212> TYPE: PRT
<213> ORGANISM: Artificial
<220> FEATURE:
<223> OTHER INFORMATION: Mutein of hNGAL

<400> SEQUENCE: 10

Gln Asp Ser Thr Ser Asp Leu Ile Pro Ala Pro Leu Ser Lys Val
1               5                   10                  15

Pro Leu Gln Gln Asn Phe Gln Asp Asn Gln Phe His Gly Lys Trp Tyr
            20                  25                  30

Gln Val Gly Arg Ala Gly Asn Ala Ala Pro Arg Glu Asp Lys Asp Leu
        35                  40                  45

Leu Lys Met Thr Ala Gln Thr Tyr Glu Leu Lys Glu Asp Lys Ser Tyr
    50                  55                  60

Asn Val Thr Ala Val Arg Phe Arg Lys Lys Met Cys Glu Tyr Leu Thr
65                  70                  75                  80

Met Thr Phe Val Pro Gly Ser Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Gln Gln
        115                 120                 125

Asn Arg Glu Tyr Phe Ser Ile Ser Leu Leu Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 11
<211> LENGTH: 71
<212> TYPE: DNA
<213> ORGANISM: artificial
<220> FEATURE:
<223> OTHER INFORMATION: Degerate oligodeoxynucleotide P1
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (46)..(47)

<223> OTHER INFORMATION: n is a, c, g, or t

<400> SEQUENCE: 11
caattccatg ggaagtggta tynsgtaggt ynsgcaggga atgcannsct cagagaagac    60
aaagacccgc a    71

<210> SEQ ID NO 12
<211> LENGTH: 71
<212> TYPE: DNA
<213> ORGANISM: artificial
<220> FEATURE:
<223> OTHER INFORMATION: Degenerate oligodeoxynucleotide P2
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t

<400> SEQUENCE: 12
gtgacattgt agctcttatc ttctttcagc tcatagatsn rggcsnncat cttttgcggg    60
tctttgtctt c    71

<210> SEQ ID NO 13
<211> LENGTH: 79
<212> TYPE: DNA
<213> ORGANISM: artificial
<220> FEATURE:
<223> OTHER INFORMATION: Degenerate oligodeoxynucleotide P3
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t

<400> SEQUENCE: 13
aagagctaca atgtcacann sgtcnnsttt aggaaaaaga agtgtgacta cnnsatcnns    60
acttttgttc caggttccc    79

<210> SEQ ID NO 14
<211> LENGTH: 55
<212> TYPE: DNA
<213> ORGANISM: artificial
<220> FEATURE:
<223> OTHER INFORMATION: Degenerate oligodeoxynucleotide P4
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t

```
<400> SEQUENCE: 14
gccagctcct tggttctccc snrgagsnrg atsnngaagt actccctgtt ttgag         55

<210> SEQ ID NO 15
<211> LENGTH: 28
<212> TYPE: DNA
<213> ORGANISM: artificial
<220> FEATURE:
<223> OTHER INFORMATION: PCR Primer P5

<400> SEQUENCE: 15
ccaggacaac caattccatg ggaagtgg                                       28

<210> SEQ ID NO 16
<211> LENGTH: 26
<212> TYPE: DNA
<213> ORGANISM: artificial
<220> FEATURE:
<223> OTHER INFORMATION: PCR primer P6

<400> SEQUENCE: 16
gttccgaagc cagctccttg gttctc                                         26

<210> SEQ ID NO 17
<211> LENGTH: 42
<212> TYPE: DNA
<213> ORGANISM: artificial
<220> FEATURE:
<223> OTHER INFORMATION: PCR primer mut79back
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t

<400> SEQUENCE: 17
ggaacctgga acaaaagtca tsnnsnngta gtcacacttc tt                       42

<210> SEQ ID NO 18
<211> LENGTH: 19
<212> TYPE: DNA
<213> ORGANISM: artificial
<220> FEATURE:
<223> OTHER INFORMATION: PCR primer mut79for

<400> SEQUENCE: 18 gactttttgtt ccaggttcc                                                19

<210> SEQ ID NO 19
<211> LENGTH: 75
<212> TYPE: DNA
<213> ORGANISM: artificial
<220> FEATURE:
<223> OTHER INFORMATION: PCR primer mut127back
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (61)..(62)
<223> OTHER INFORMATION: n is a, c, g, or t

<400> SEQUENCE: 19
gccagctcct tggttctccc gaggagggtg atggagaagt actccctgtt ttgsnnaacs    60
```
nncttgaaga acacc                                                  75

<210> SEQ ID NO 20
<211> LENGTH: 55
<212> TYPE: DNA
<213> ORGANISM: artificial
<220> FEATURE:
<223> OTHER INFORMATION: PCR primer mut77back
<220> FEATURE:
<221> NAME/KEY: misc_feature
<222> LOCATION: (32)..(33)
<223> OTHER INFORMATION: n is a, c, g, or t

<400> SEQUENCE: 20
ggaacctgga acaaaagtca tggtcaggta snnacacttc tttttcctaa acctg      55

<210> SEQ ID NO 21
<211> LENGTH: 47
<212> TYPE: DNA
<213> ORGANISM: artificial
<220> FEATURE:
<223> OTHER INFORMATION: PCR primer mut136back
<220> FEATURE:
<221> NAME/KEY: misc_feature
<222> LOCATION: (28)..(29)
<223> OTHER INFORMATION: n is a, c, g, or t

<400> SEQUENCE: 21
gccagctcct tggttctccc gaggagsnng atggagaagt actccct               47

<210> SEQ ID NO 22
<211> LENGTH: 39
<212> TYPE: DNA
<213> ORGANISM: artificial
<220> FEATURE:
<223> OTHER INFORMATION: PCR primer mut33for
<220> FEATURE:
<221> NAME/KEY: misc_feature
<222> LOCATION: (22)..(23)
<223> OTHER INFORMATION: n is a, c, g, or t

<400> SEQUENCE: 22
caattccatg ggaagtggta tnnsgtaggt cgggcaggg                        39

<210> SEQ ID NO 23
<211> LENGTH: 40
<212> TYPE: DNA
<213> ORGANISM: artificial
<220> FEATURE:
<223> OTHER INFORMATION: PCR primer mut54back
<220> FEATURE:
<221> NAME/KEY: misc_feature
<222> LOCATION: (21)..(22)
<223> OTHER INFORMATION: n is a, c, g, or t

<400> SEQUENCE: 23
cttctttcag ctcatagats nnggcggtca tcttttgcgg                       40

<210> SEQ ID NO 24
<211> LENGTH: 19
<212> TYPE: DNA
<213> ORGANISM: artificial
<220> FEATURE:
<223> OTHER INFORMATION: PCR primer mut136for

<400> SEQUENCE: 24
atctatgagc tgaaagaag                                              19

<210> SEQ ID NO 25

```
<211> LENGTH: 21
<212> TYPE: DNA
<213> ORGANISM: Artificial
<220> FEATURE:
<223> OTHER INFORMATION: PCR primer NGAL26

<400> SEQUENCE: 25
cccaggactc cacctcagac c                                           21

<210> SEQ ID NO 26
<211> LENGTH: 18
<212> TYPE: DNA
<213> ORGANISM: Artificial
<220> FEATURE:
<223> OTHER INFORMATION: PCR primer L1Mback

<400> SEQUENCE: 26
tggggctgca ttccctgc                                               18

<210> SEQ ID NO 27
<211> LENGTH: 64
<212> TYPE: DNA
<213> ORGANISM: Artificial
<220> FEATURE:
<223> OTHER INFORMATION: PCR primer L1Mfor
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t

<400> SEQUENCE: 27
gcagggaatg cagctccann snnsnnsnns nnsctgctan nsnnsaccgc ctagacttat   60
gagc                                                              64

<210> SEQ ID NO 28
<211> LENGTH: 178
<212> TYPE: PRT
<213> ORGANISM: Artificial
<220> FEATURE:
<223> OTHER INFORMATION: Mutein of hNGAL

<400> SEQUENCE: 28

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30
```

Gln Val Gly Arg Ala Gly Asn Ala Ala Pro Pro Val Asp Pro Glu Leu
            35                  40                  45

Leu Leu Leu Thr Ala Gln Thr Tyr Glu Leu Lys Glu Asp Lys Ser Tyr
 50                  55                  60

Asn Val Thr Ala Val Arg Phe Arg Lys Lys Met Cys Glu Tyr Leu Thr
 65                  70                  75                  80

Met Thr Phe Val Pro Gly Ser Gln Pro Gly Glu Phe Thr Leu Gly Asn
                 85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Gln Gln
                115                 120                 125

Asn Arg Glu Tyr Phe Ser Ile Ser Leu Leu Gly Arg Thr Lys Glu Leu
130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 29
<211> LENGTH: 178
<212> TYPE: PRT
<213> ORGANISM: Artificial
<220> FEATURE:
<223> OTHER INFORMATION: Mutein of hNGAL

<400> SEQUENCE: 29

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
                 20                  25                  30

Gln Val Gly Arg Ala Gly Asn Ala Ala Pro Pro Val Asp Pro Glu Leu
            35                  40                  45

Leu Leu Leu Thr Ala Gln Thr Tyr Glu Leu Lys Glu Asp Lys Ser Tyr
 50                  55                  60

Asp Val Thr Ala Val Arg Phe Arg Lys Lys Met Cys Glu Tyr Leu Thr
 65                  70                  75                  80

Met Thr Phe Val Pro Gly Ser Gln Pro Gly Glu Phe Thr Leu Gly Asn
                 85                  90                  95

Ile Glu Ser Tyr Pro Gly Leu Thr Ser Tyr Leu Val Arg Met Val Ser
                100                 105                 110

Thr Asn Tyr Asn Gln His Ala Met Val Phe Phe Lys Lys Val Gln Gln
                115                 120                 125

Asn Arg Glu Tyr Phe Ser Ile Ser Leu Leu Gly Arg Thr Lys Glu Leu
130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 30
<211> LENGTH: 178
<212> TYPE: PRT
<213> ORGANISM: Artificial
<220> FEATURE:

-continued

<223> OTHER INFORMATION: Mutein of hNGAL

<400> SEQUENCE: 30

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Gln Val Gly Arg Ala Gly Asn Ala Ala Pro Pro Val Asp Pro Glu Leu
        35                  40                  45

Leu Leu Leu Thr Ala Gln Thr Tyr Glu Leu Lys Glu Asp Lys Ser Tyr
    50                  55                  60

Asp Val Thr Ala Val Arg Phe Arg Lys Lys Met Cys Glu Tyr Leu Thr
65                  70                  75                  80

Met Thr Phe Val Pro Ser Ser Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Gln Gln
        115                 120                 125

Asn Arg Glu Tyr Phe Ser Ile Ser Leu Leu Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 31
<211> LENGTH: 178
<212> TYPE: PRT
<213> ORGANISM: Artificial
<220> FEATURE:
<223> OTHER INFORMATION: Mutein of hNGAL

<400> SEQUENCE: 31

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Gln Val Gly Arg Ala Gly Asn Ala Ala Pro Met Asp Pro Glu Leu
        35                  40                  45

Leu Leu Leu Thr Ala Gln Thr Tyr Glu Leu Lys Glu Asp Lys Ser Tyr
    50                  55                  60

Asp Val Thr Ala Val Arg Phe Arg Lys Lys Met Cys Glu Tyr Leu Thr
65                  70                  75                  80

Met Thr Phe Val Pro Ser Pro Gln Pro Gly Glu Phe Thr Leu Gly Asn
                85                  90                  95

Ile Lys Asn Tyr Pro Gly Leu Thr Ser Tyr Phe Val Arg Val Val Ser
            100                 105                 110

Thr Asn Tyr Asn Gln His Ala Met Val Phe Phe Lys Lys Val Gln Gln
        115                 120                 125

Asn Arg Glu Tyr Phe Ser Ile Ser Leu Leu Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
```

-continued

```
                165                 170                 175
Asp Gly

<210> SEQ ID NO 32
<211> LENGTH: 178
<212> TYPE: PRT
<213> ORGANISM: Artificial
<220> FEATURE:
<223> OTHER INFORMATION: Mutein of hNGAL

<400> SEQUENCE: 32

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Gln Val Gly Arg Ala Gly Asn Ala Ala Pro Val Asp Pro Glu Leu
        35                  40                  45

Leu Leu Leu Thr Ala Gln Thr Tyr Glu Leu Arg Glu Asp Lys Ser Tyr
    50                  55                  60

Asp Val Thr Ala Val Arg Phe Arg Lys Lys Met Cys Glu Tyr Leu Thr
65                  70                  75                  80

Met Thr Phe Val Pro Gly Ser Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Gln Gln
        115                 120                 125

Asn Arg Glu Tyr Phe Ser Ile Ser Leu Leu Gly Arg Thr Lys Glu Leu
    130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 33
<211> LENGTH: 178
<212> TYPE: PRT
<213> ORGANISM: Artificial
<220> FEATURE:
<223> OTHER INFORMATION: Mutein of hNGAL

<400> SEQUENCE: 33

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Gln Val Gly Arg Ala Gly Asn Ala Ala Pro Val Asp Pro Glu Leu
        35                  40                  45

Leu Leu Leu Thr Ala Gln Thr Tyr Glu Leu Lys Glu Asp Lys Ser Tyr
    50                  55                  60

Asp Val Thr Ala Val Arg Phe Arg Lys Lys Met Cys Glu Tyr Leu Thr
65                  70                  75                  80

Met Thr Phe Val Pro Gly Phe Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110
```

-continued

```
Thr Asn Tyr Asn Gln His Ala Met Val Phe Phe Lys Lys Val Gln Gln
        115                 120                 125

Asn Arg Glu Tyr Phe Ser Ile Ser Leu Leu Gly Arg Thr Lys Glu Leu
        130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 34
<211> LENGTH: 178
<212> TYPE: PRT
<213> ORGANISM: Artificial
<220> FEATURE:
<223> OTHER INFORMATION: Mutein of hNGAL

<400> SEQUENCE: 34

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Gln Val Gly Arg Ala Gly Asn Ala Ala Pro Pro Val Asp Pro Glu Leu
            35                  40                  45

Leu Leu Leu Thr Ala Gln Thr Tyr Glu Leu Lys Glu Asp Lys Ser Tyr
        50                  55                  60

Asn Val Thr Ala Val Arg Phe Arg Lys Lys Met Cys Glu His Leu Thr
65                  70                  75                  80

Met Thr Phe Val Pro Gly Ser Gln Pro Gly Glu Phe Thr Leu Gly Asn
                85                  90                  95

Ile Lys Ser Tyr Pro Gly Ile Thr Ser Tyr Phe Val Arg Val Ala Ser
            100                 105                 110

Thr Asn Tyr Asn Gln His Ala Met Val Phe Phe Lys Lys Val Gln Gln
        115                 120                 125

Asn Arg Glu Tyr Phe Ser Ile Ser Leu Leu Gly Arg Thr Lys Glu Leu
        130                 135                 140

Ala Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

MUTEINS OF HNGAL AND RELATED PROTEINS WITH AFFINITY FOR A GIVEN TARGET

CROSS-REFERENCE TO RELATED APPLICATIONS

This application is a National Stage application of PCT/EP2009/057925, filed Jun. 24, 2009, which claims the benefit of priority of U.S. provisional application No. 61/075,175 filed Jun. 24, 2008 the contents of which are hereby incorporated by reference it their entirety for all purposes.

FIELD OF THE INVENTION

The present invention relates to novel muteins derived from human lipocalin 2 (hNGAL) and related proteins that bind a given non-natural ligand with detectable affinity. The invention also relates to corresponding nucleic acid molecules encoding such a mutein and to a method for their generation. The invention further relates a method for producing such a mutein. Furthermore, the invention is directed to a pharmaceutical composition comprising such a lipocalin mutein as well as to various uses of the mutein.

BACKGROUND OF THE INVENTION

The lipocalins are a diverse family of small and robust, secretory proteins which serve for the transport or storage of poorly soluble or chemically sensitive vitamins, hormones, and metabolites (such as retinoids, fatty acids, cholesterols, prostaglandins, biliverdins, pheromones, tastants, and odorants) in many organisms (Åkerström et al. Eds. (2006), Lipocalins, Landes Bioscience, Georgetown, Tex.; Pervaiz, S., and Brew, K. (1987) *FASEB J.* 1, 209-214). Although they have, in the past, been classified primarily as transport proteins, it is now clear that the lipocalins fulfill a variety of physiological functions. These include roles in retinol transport, olfaction, pheromone signaling, and the synthesis of prostaglandins. The lipocalins have also been implicated in the regulation of the immune response and the mediation of cell homoeostasis (reviewed, for example, in Flower, D. R. (1996) *Biochem. J.* 318, 1-14 and Flower, D. R. et al. (2000) *Biochim. Biophys. Acta* 1482, 9-24).

The lipocalins share unusually low levels of overall sequence conservation, often with sequence identities of less than 20%. In strong contrast, their overall folding pattern is highly conserved. The central part of the lipocalin structure consists of a single eight-stranded anti-parallel β-sheet closed back on itself to form a continuously hydrogen-bonded β-barrel. One end of the barrel is sterically blocked by the N-terminal peptide segment that runs across its bottom as well as three peptide loops connecting the β-strands. The other end of the β-barrel is open to the solvent and encompasses a target-binding site, which is formed by four peptide loops. It is this diversity of the loops in the otherwise rigid lipocalin scaffold that gives rise to a variety of different binding modes each capable of accommodating targets of different size, shape, and chemical character (reviewed, e.g., in Flower, D. R. (1996), supra; Flower, D. R. et al. (2000), supra, or Skerra, A. (2000) *Biochim. Biophys. Acta* 1482, 337-350).

Among the 10-12 members of the lipocalin family that are found in the human body, human neutrophil gelatinase-associated lipocalin (hNGAL) (Kjeldsen et al. (2000) *Biochim. Biophys. Acta* 1482, 272-283)—also known as lipocalin 2 (Lcn2) or, more recently, dubbed siderocalin (Goetz et al. (2002) *Mol. Cell.* 10, 1033-1043)—plays a role in the innate immune defence against bacterial infections by scavenging $Fe^{3+}$ ions bound to certain bacterial siderophores.

Such siderophores are highly potent iron chelators which are secreted by pathogenic bacteria in response to limiting iron concentrations (Schaible & Kaufmann (2004). *Nat. Rev. Microbiol.* 2, 946-953), as they happen in the human body fluids, to allow iron uptake by specialized bacterial import systems (Braun & Braun (2002) *Curr. Opin. Microbial.* 5, 194-201; Fischbach et al. (2006) *Nat. Chem. Biol.* 2, 132-138). It seems that neutrophils release hNGAL at sites of infection as an antimicrobial strategy. Indeed, the physiological relevance of hNGAL has been demonstrated in corresponding knock-out mice, where this lipocalin was shown to be essential in limiting the spreading of bacteria that rely on enterobactin-mediated iron import (Flo et al. (2004) *Nature* 432, 917-921)

hNGAL (also termed Lcn2, SWISS-PROT Data Bank Accession Number P80188) is a 178 amino acid glycoprotein with strong binding activity towards the catecholate-type siderophore $Fe^{3+}$-enterobactin (or enterochelin), which is characteristic for *Escherichia coli* (Raymond et al. (2003) *Proc. Natl. Acad. Sci. USA* 100, 3584-8). hNGAL is an abundant human plasma protein, whose normal concentration is around 80 µg/L and can increase up to ten-fold upon bacterial infections (Xu and Venge (2000) *Biochim. Biophys. Acta* 1482, 298-307), and its single N-linked glycosylation site is dispensable for folding (Coles et al. (1999) *J. Mol. Biol.* 289, 139-157). Compared with other lipocalins, hNGAL exhibits an unusually large pocket. Therein, a cluster of positively charged side chains confers extraordinary affinity for the negatively charged ferric siderophore, with a dissociation constant ($K_D$) of 0.4 nM (Goetz et al., supra), thus allowing effective competition with the bacterial uptake system. Ligand recognition by hNGAL is rather specific as this lipocalin also forms stable complexes with the chemically related bacillibactin from *Bacillus anthracis* (Abergel et al. (2006) *Proc. Natl. Acad. Sci. USA* 103, 18499-18503) and with carboxymycobactins from *Mycobacterium tuberculosis* (Holmes et al. (2005) *Structure* 13, 29-41), a siderophore type of similar size and shape. However, it does not bind petrobactin, the siderophore that is crucial for virulence of *B. anthracis* (Abergel et al., supra), or C-glycosylated enterobactin analogues such as the salmochelins produced by *Salmonella* spp. and *Klebsiella pneumoniae* (Fischbach et al., supra). Animal homologs to human Lcn2 are rat $\alpha_2$-microglobulin-related protein (A2m; SWISS-PROT Data Bank Accession Number P31052) and mouse 24p3/uterocalin (24p3; SWISS-PROT Data Bank Accession Number P11672).

Proteins that selectively bind to their corresponding targets by way of non-covalent interaction play a crucial role as reagents in biotechnology, medicine, bioanalytics as well as in the biological and life sciences in general. Antibodies, i.e. immunoglobulins, are a prominent example of this class of proteins. Despite the manifold needs for such proteins in conjunction with recognition, binding and/or separation of ligands/targets, almost exclusively immunoglobulins are currently used. The application of other proteins with defined ligand-binding characteristics, for example the lectins, has remained restricted to special cases.

Rather recently, members of the lipocalin family have become subject of research concerning proteins having defined ligand-binding properties. The PCT publication WO 99/16873 discloses polypeptides of the lipocalin family with mutated amino acid positions in the region of the four peptide loops, which are arranged at the end of the cylindrical β-barrel structure encompassing the binding pocket, and which correspond to those segments in the linear polypeptide sequence comprising the amino acid positions 28 to 45, 58 to 69, 86 to 99, and 114 to 129 of the bilin-binding protein of *Pieris brassicae*.

The PCT publication WO 00/75308 discloses muteins of the bilin-binding protein, which specifically bind digoxigenin, whereas the International Patent Applications WO 03/029463 and WO 03/029471 relate to muteins of the human neutrophil gelatinase-associated lipocalin (hNGAL) and apolipoprotein D, respectively. In order to further improve and fine tune ligand affinity, specificity as well as folding stability of a lipocalin variant various approaches using different members of the lipocalin family have been proposed (Skerra, A. (2001) *Rev. Mol. Biotechnol.* 74, 257-275; Schlehuber, S., and Skerra, A. (2002) *Biophys. Chem.* 96, 213-228), such as the replacement of additional amino acid residues. The PCT publication WO 2006/56464 discloses muteins of human neutrophil gelatinase-associated lipocalin with binding affinity for CTLA-4 in the low nanomolar range.

The PCT publication WO 2005/19256 discloses muteins of tear lipocalin with at least one binding site for different or the same target ligand and provides a method for the generation of such muteins of human tear lipocalin. According to this PCT application, certain amino acid stretches within the primary sequence of tear lipocalin, in particular the loop regions comprising amino acids 7-14, 24-36, 41-49, 53-66, 69-77, 79-84, 87-98, and 103-110 of mature human tear lipocalin, are subjected to mutagenesis in order to generate muteins with binding affinities. The resulting muteins have binding affinities for the selected ligand ($K_D$) in the nanomolar range.

The lipocalin muteins disclosed in the above references are selected to preferentially bind large, proteinaceous target molecules and not small molecules. Thus, despite the progress made in this field, it would be desirable to have hNGAL muteins that are specifically adapted to bind small molecules with high binding affinity, for example in the nanomolar range. Such muteins would further improve the suitability of muteins of hNGAL in diagnostic and therapeutic applications.

SUMMARY OF THE INVENTION

This object is accomplished by a mutein of hNGAL or of a related protein having the features of the independent claims.

In a first aspect, the present invention provides a mutein derived from a protein selected from the group consisting of human neutrophil gelatinase-associated lipocalin (hNGAL), rat $\alpha_2$-microglobulin-related protein (A2m) and mouse 24p3/uterocalin (24p3), said mutein including at least one mutated amino acid residue at any of the sequence positions corresponding to the sequence positions 33, 36, 41, 52, 54, 68, 70, 79, 81, 134, 136 and 138 of the linear polypeptide sequence of hNGAL, and wherein the mutein binds a given target with detectable affinity.

DETAILED DESCRIPTION OF THE INVENTION

In this context, it s noted that the invention is based on the surprising finding that subjecting human neutrophil gelatinase-associated lipocalin (hNGAL), rat $\alpha_2$-microglobulin-related protein (A2m) and mouse 24p3/uterocalin (24p3) to mutagenesis at one or more of these above-mentioned 12 sequence position provides for muteins that have a sufficiently affine binding to pre-defined target with low molecular weight.

In this context, it is also noted that in modern medicine, compounds of low molecular weight such as metal-chelate complexes play an increasing role for medical purposes, for example, the purposes of radio-immuno therapy (RIT)) and also for diagnostic purposes, for example in vivo imaging (Kenanova and Wu (2006) *Expert Opin, Drug Deliv.* 3, 53-70). Typically, for such a purpose, antibodies directed against tumor-specific cell surface markers—or peptides specific for disease-related receptors—have so far chemically conjugated to potent synthetic chelating agents (Milenic et al. (2004) *Nat. Rev. Drug Discov.* 3, 488-499), in particular DOTA (1,4,7,10-tetra-azacylcododecane-N,N',N'',N'''-tetraacetic acid) and DTPA (diethylenetriamine pentaacetic acid) or their derivatives, which are then charged with radionuclides of the rare earth elements such as $Y^{3+}$ or $Lu^{3+}$ or similar trivalent metal ions, e.g. $In^{3+}$ or $Bi^{3+}$. Two radionuclide-conjugated antibodies directed against CD20, Zevalin® and Bexxar®, have been approved for the therapy of non-Hodgkin's lymphoma and many antibodies and their fragments are currently subject to protein engineering for improved pharmacokinetics and tumor targeting (Kenanova and Wu, supra).

A major obstacle of humanized antibodies for nuclear medicine is the long circulation time, which leads to low contrast for imaging and limited tumor specificity during RIT. To circumvent this problem, so-called pre-targeting strategies have been developed, where the tumor-targeting antibody is uncoupled from the chelated radionuclide (Chang et al. (2002) *Mol. Cancer. Ther,* 1, 553-563). This enables the slow process of antibody localization and clearance from circulation in the first stage, prior to the fast and specific delivery of the small molecule radioactive payload in the second stage. Initially, antibody-streptavidin conjugates were applied in conjunction with biotinylated radionuclide chelates and, later, bispecific antibodies together with epitope peptide-conjugated chelate complexes. Moreover, monoclonal antibodies were developed which can directly bind the metal chelate (Le Doussal et al. (1990) *Cancer Res.* 50, 3445-3452; Corneillie et al. (2003) *J. Am. Chem. Soc.* 125, 3436-3437; Corneillie et al. (2003) *J. Am. Chem. Soc.* 125, 15039-15048).

The ideal system, however, would be a small metal chelate-specific binding protein, comprising a single polypeptide chain with robust folding properties, which can simply be coupled to a targeting peptide/protein module—e.g. a natural receptor ligand, an antibody fragment (Kenanova and Wu, supra) or an alternative binding protein (Skerra (2007) *Curr. Opin. Biotechnol.* 18, 295-304; Skerra (2007) *Curr. Opin. Mol. Ther.* 9, 336-344)—using a gene fusion strategy. The muteins of hNGAL, rat $\alpha_2$-microglobulin-related protein (A2m) and mouse 24p3/uterocalin (24p3) provide such a protein having high binding affinity for such small target molecules.

The term "human neutrophil gelatinase-associated lipocalin" or "hNGAL" or "lipocalin 2" or "Lcn2" as used herein to refer to the mature hNGAL with the SWISS-PROT Data Bank Accession Number P80188. The amino acid sequence of human neutrophil gelatinase-associated lipocalin is set forth in SEQ ID NO: 1. The terms "rat $\alpha_2$-microglobulin-related protein" or "A2m" and "mouse 24p3/uterocalin" or "24p3" as used in the present application refer to mature A2m or 24p3 with the SWISS-PROT Data Bank Accession Numbers P31052 and P11672, respectively.

The given target may be any desired non-natural target/ligand. The term "non-natural ligand" refers to any compound, which does not bind to native mature hNGAL under physiological conditions. The target (ligand) may be any chemical compound in free or conjugated form which exhibits features of an immunological hapten, for example, a small organic molecule, such as a metal-chelating agent, or a peptide, for example of 2 to about 25 or about 30 or about 35 amino acids length (see below).

The term "organic molecule" or "small organic molecule" as used herein denotes an organic molecule comprising at least two carbon atoms, but preferably not more than 7 or 12 rotatable carbon bonds, having a molecular weight in the range between 100 and 2000 Dalton, preferably between 100 and 1000 Dalton, and optionally including one or two metal atoms.

The term "peptide" as used herein with reference to a target molecule refers to a dipeptide or an oligopeptide with of 2-40, 2-35, 2-30, 2-25, 2-20, 2-15 or 2-10 amino acid residues. The peptide may be a naturally occurring or synthetic peptide and may comprise—besides the 20 naturally occurring L-amino acids—D-amino acids, non-naturally occurring amino acids and amino acid analogs.

An hNGAL mutein (or the mutein of rat $\alpha_2$-microglobulin-related protein (A2m) and mouse 24p3/uterocalin (24p3) of the invention may comprise the wild type (natural) amino acid sequence outside the mutated amino acid sequence positions. On the other hand, the lipocalin muteins disclosed herein may also contain amino acid mutations outside the sequence positions subjected to mutagenesis as long as those mutations do not interfere with the binding activity and the folding of the mutein. Such mutations can be accomplished very easily on DNA level using established standard methods (Sambrook, I. et al. (1989) *Molecular Cloning: A Laboratory Manual,* 2nd Ed., Cold Spring Harbor Laboratory Press, Cold Spring Harbor, N.Y.). Possible alterations of the amino acid sequence are insertions or deletions as well as amino acid substitutions. Such substitutions may be conservative, i.e. an amino acid residue is replaced with a chemically similar amino acid residue. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan. One the other hand, it is also possible to introduce non-conservative alterations in the amino acid sequence. In addition, instead of replacing single amino acid residues, it is also possible to either insert or delete one or more continuous amino acids of the primary structure of hNGAL as long as these deletions or insertion result in a stable folded/functional mutein.

Such modifications of the amino acid sequence include directed mutagenesis of single amino acid positions in order to simplify sub-cloning of the mutated lipocalin gene or its parts by incorporating cleavage sites for certain restriction enzymes. In addition, these mutations can also be incorporated to further improve the affinity of a lipocalin mutein for a given target. Furthermore, mutations can be introduced in order to modulate certain characteristics of the mutein such as to improve folding stability, serum stability, protein resistance or water solubility or to reduce aggregation tendency, if necessary. For example, naturally occurring cysteine residues may be mutated to other amino acids to prevent disulphide bridge formation. However, it is also possible to deliberately mutate other amino acid sequence position to cysteine in order to introduce new reactive groups, for example for the conjugation to other compounds, such as polyethylene glycol (PEG), hydroxyethyl starch (HES), biotin, peptides or proteins, or for the formation of non-naturally occurring disulphide linkages. Exemplary possibilities of such a mutation to introduce a cysteine residue into the amino acid sequence of an hNGAL mutein include the introduction of a cysteine (Cys) residue at least one of the sequence positions that correspond to sequence positions 14, 21, 60, 84, 88, 116, 141, 145, 143, 146 or 158 of the wild type sequence of hNGAL. The generated thiol moiety at the side of any of the amino acid positions 14, 21, 60, 84, 88, 116, 141, 145, 143, 146 and/or 158 may be used to PEGylate or HESylate the mutein, for example, in order to increase the serum half-life of a respective hNGAL mutein.

In one embodiment of the invention, the mutein includes mutated amino acid residues at least any 2, 3, 4, 5, 6, 7, 8, 9, 10, 11 or all 12 of the sequence positions corresponding to the sequence positions 33, 36, 41, 52, 54, 68, 70, 79, 81, 134, 136 and 138 of the linear polypeptide sequence of hNGAL.

In a further embodiment of the invention, the mutein further includes at least one mutated amino acid residue at any of the sequence positions corresponding to the sequence positions 42, 48, 49, 55, 75, 77, 80 and 127 of the linear polypeptide sequence of hNGAL. Such a mutein may, for example, include at least 9 mutated amino acid residues at any of the sequence positions corresponding to the sequence positions 33, 36, 41, 42, 48, 49, 52, 54, 55, 68, 70, 75, 77, 79, 80, 81, 127, 134, 136 and 138 of the linear polypeptide sequence of hNGAL. In one embodiment of the present invention, the mutein includes mutated amino acid residues at least any 10, 14, 15 or all 20 of the above-listed sequence positions. The mutein may further comprise at least one mutated amino acid residue at any of the sequence positions corresponding to the sequence positions 43, 44, 46, 47, 50, 51, 59, 65, 78, 86, 87, 98, 99, 103, 107, 110 and 111 of the linear polypeptide sequence of hNGAL. Such a mutein may, for example, include at least 9 mutated amino acid residues at any of the sequence positions corresponding to the sequence positions 33, 36, 41, 42, 43, 44, 46, 47, 48, 49, 50, 51, 52, 54, 55, 59, 65, 68, 70, 75, 77, 78, 79, 80, 81, 86, 87, 98, 99, 103, 107, 110, 111, 127, 134, 136 and 138 of the linear polypeptide sequence of hNGAL.

In one embodiment of the present invention, the mutein includes mutated amino acid residues at least any 10, 14, 15, 20, 22, 24, 26, 28, 29, 30, 31, 32, 33, 35 or all 37 of the above-listed sequence positions.

In a still further embodiment of the present invention, the mutein includes with respect to the mature hNGAL wild type amino acid sequence additional amino acid replacements at least one of the sequence positions that correspond to sequence positions 65, 71, 73, 74, 116, 125 and 135 of the wild type sequence of hNGAL.

In still another embodiment, the muteins of the present invention may further include one or more of the amino acid replacements selected from the group consisting of Glu28→His, Cys87→Ser, and Tlu-145→Ala.

The lipocalin muteins of the invention are able to bind the desired target with detectable affinity, i.e. with a dissociation constant of at least 200 nM. Preferred in some embodiments are lipocalin muteins, which bind the desired target with a dissociation constant for a given target of at least 100, 20, 1 nM or even less. The binding affinity of a mutein to the desired target can be measured by a multitude of methods such as fluorescence titration, competition ELISA or surface plasmon resonance (Biacore).

It is readily apparent to the skilled person that complex formation is dependent on many factors such as concentration of the binding partners, the presence of competitors, ionic strength of the buffer system etc. Selection and enrichment is generally performed under conditions allowing the isolation of lipocalin muteins having, in complex with the desired target, a dissociation constant of at least 200 nM. However, the washing and elution steps can be carried out under varying stringency. A selection with respect to the kinetic characteristics is possible as well. For example, the selection can be performed under conditions, which favor complex formation of the target with muteins that show a slow dissociation from the target, or in other words a low $k_{off}$ rate. Alternatively, selection can be performed under conditions, which favor fast formation of the complex between the mutein and the target, or in other words a high $k_{on}$ rate.

An hNGAL mutein of the invention typically exists as monomeric protein. However, it is also possible that an inventive lipocalin mutein is able to spontaneously dimerise or oligomerise. Although the use of lipocalin muteins that form stable monomers may be preferred for some applications, e.g. because of faster diffusion and better tissue penetration, the use of lipocalin muteins that form stable homodimers or multimers may be advantageous in other instances, since such multimers can provide for a (further) increased affinity and/or avidity to a given target. Furthermore, oligomeric forms of the lipocalin mutein may have slower dissociation rates or prolonged serum half-life.

According to one embodiment of the present invention, the mutein binds a small organic molecule. The small organic molecule may be a metal-chelating agent or a pharmaceutical agent, such as a carboxy or amino group containing metal chelating-agent. Non-limiting examples for such chelating agents are ethylene-diamine-tetraacetic acid (EDTA), diethylenetriamine pentaacetic acid (DPTA), 1,4,7,10-tetra-azacylcododecane-N,N',N'',N'''-tetraacetic acid (DOTA) or derivatives thereof such as 2-methyl-6-(p-isothiocyanatobenzyl)-1,4,7,10-tetraazacyclododecane-1,4,7,10-tetraacetic acid (1B4M-DOTA), 2-(p-isothiocyanatobenzyl)-5,6-cyclohexano-1,4,7,10-tetraazacyclododecane-1,4,7,10-tetraacetate (CHX-DOTA), 2-(p-isothiocyanatobenzyl)-1,4,7,10-tetraazacyclododecane-1,4,7,10-tetraacetic acid (C-DOTA) and 1,4,7,10-Tetraaza-N-(1-carboxy-3-(4-nitrophenyl)propyl)-N',N'',N'''-tris(acetic acid) cyclododecane (PA-DOTA) (see for example, Chappell, L, Synthesis and evaluation of novel bifunctional chelating agents based on 1,4,7,10-tetraazacyclododecane-N,N',N'',N'''-tetraacetic acid for radiolabeling proteins. Nuclear Medicine and Biology, Volume 30, Issue 6, Pages 581-595), to name only a few illustrative examples. The DPTA, DOTA or derivative thereof may be complexed with a metal ion, which, for example, is selected from the group consisting of yttrium (Y), terbium (Tb), indium (In), lutetium (Lu) and bismuth (Bi). The DTPA derivative may, for example, be cyclohexyl-DTPA, including the diethylenetriamine pentaacetic acid (DTPA) series of amino acids described in U.S. Pat. Nos. 5,124,471, 5,286,850 and 5,434,287. Another example of chelating agents which can be bound by muteins of the present invention are hydroxamic acid-based bifunctional chelating agents as described in U.S. Pat. No. 5,756,825. Another example is the chelating agent termed p-SCN-Bz-HEHA (1,4,7,10,13,16-hexaazacyclo-octadecane-N,N',N'',N''',N'''',N''''''-hexaacetic acid) (Deal et al., J. Med. Chem. 42: 2988, 1999), which is an effective chelator of radionuclides such as 225Ac.

In this context, it is noted that it is possible using the present invention to generate a mutein that can bind to any chelating agent that in turn complexes a given radionuclide. Characteristics such as physical and chemical properties and the nature of the radiation are determinants of the suitability of a radionuclide for therapy. Cytotoxic radionuclides may be divided into 3 groups of radiochemicals: halogens (iodine, $^{211}$At) metals ($^{90}$Y, $^{67}$Cu, $^{213}$Bi, $^{212}$Bi), and transitional elements ($^{186}$Re). Radionuclides can further be categorized into 4 types of cytotoxic agents: pure β-emitters ($^{67}$Cu, $^{90}$Y); α-emitters ($^{213}$Bi, $^{211}$At) β-emitters that emit γ-radiation ($^{177}$Lu, $^{186}$Re, $^{131}$I), and Auger emitters and radionuclides that decay by internal conversion, including $^{125}$I and $^{67}$Ga. The use of muteins that bind to a chelating agent that forms complexes with any of these radionuclides is contemplated in the present invention (cf., for example, Yuliya S. Jhanwar & Chaitanya Divgi, Current Status of Therapy of Solid Tumors, Journal of Nuclear Medicine Vol. 46 No. 1 (Suppl) 141S-150S, 2005).

Another purely illustrative example of a small molecule that can serve as given target are haptens such as norbornene haptens that have found interest as transition state analogue for the [4+2] Diels-Alder reaction (see for example, Xu et al., Science, 1999, Vol. 286, 2345-2348 or Hilvert et al., J. Am. Chem. Soc. 1989, Vol. 111, 9261-9262). Such a hapten has been used in Example 16 to illustrate the suitability of the present invention to generate muteins with affinity towards every possible small molecule against which also an immune response (that means production of antibodies) can be generated. Thus, it is noted here again that the given target can be any hapten.

Alternatively, in another embodiment of the invention, the mutein of the present invention may bind a peptide, for example a peptide of 2-40, 2-35, 2-30, 2-25, 2-20, 2-15, or 2-10 amino acids length. The peptide may be a naturally occurring peptide, such as, for example, an angiotensin (angiotensin I-IV), a natriuretic peptide (ANP, BNP, CNP), a vasopressin, an oxytocin or an opioid peptide (enkephalin, endorphin, dynorphin), or a synthetic peptide.

According to one embodiment of the present invention, the mutein of hNGAL binds a chelating agent such as DOTA or cyclohexyl-DTPA with a $K_D$ of 50 nM or less.

An hNGAL mutein of the invention that binds a chelating agent such as DOTA or cyclohexyl-DTPA may comprise with respect to the amino acid sequence of mature hNGAL at least at least 3, 4, 5, 6, 7, 8, 9, 10, 11, or 12 amino acid replacements selected from the group consisting of Val33→Gln; Leu36→Arg; Ile41→Ala; Tyr52→Thr; Thr54→Gln; Ser68→Ala; Leu70→Arg; Trp79→Ala, Len; Arg81→Met; Lys134→Ser; Thr136→Ser and Tyr138→Leu. Generally, such a mutein binds cyclohexyl-DTPA with a $K_D$ of 200 nM or less, 100 nM or less, 20 nM or less, or 1 nM or even less with a $K_D$ in the picomolar range. Thus, the invention also encompasses hNGAL muteins that bind cyclohexyl-DTPA with a $K_D$ of 900 pM or less, 600 pM or less, 500 pM or less, 250 pM, 100 pM or less, 60 pM or less or 40 pM or less. Suitable methods to determine $K_D$ values of a mutein-ligand complex are known to those skilled in the art and include fluorescence titration, competition ELISA, calorimetric methods, such as isothermal titration calorimetry (ITC), and surface plasmon resonance. Examples for such methods are detailed below (See, e.g., Examples).

In this context it is also noted that the complex formation between the respective mutein and its ligand is influenced by many different factors such as the concentrations of the respective binding partners, the presence of competitors, pH and the ionic strength of the buffer system used, and the experimental method used for determination of the dissociation constant $K_D$ (for example fluorescence titration, competition ELISA or surface plasmon resonance, just to name a few) or even the mathematical algorithm which is used for evaluation of the experimental data.

Therefore, it is also clear to the skilled person that the $K_D$ values (dissociation constant of the complex formed between the respective mutein and its ligand) given here may vary within a certain experimental range, depending on the method and experimental setup that is used for determining the affinity of a particular lipocalin mutein for a given ligand. This means, there may be a slight deviation in the measured $K_D$ values or a tolerance range depending, for example, on whether the $K_D$ value was determined by surface plasmon resonance (Biacore) or by competition ELISA.

In a specific embodiment of the invention, such a mutein further includes with respect to the mature hNGAL wild type amino acid sequence an amino acid replacement selected from the group consisting of Leu42→Pro; Pro48→Leu; Gln49→Leu; Ile55→Thr; Lys75→Met; Asp77→Glu; Ile80→Thr; and Ser127→Gln.

In one embodiment of the present invention, the hNGAL mutein binding cyclohexyl-DPTA includes the amino acid substitutions: Val33→Gln; Leu36→Arg; Ile41→Ala; Tyr52→Thr; Thr54→Gln; Ser68→Ala; Leu70→Arg; Trp79 Ala or Leu; Arg81→Met; Lys134→Ser; Thr136→Ser; and Tyr138→Leu. Such a mutein may further include with respect to the mature hNGAL wild type amino acid sequence one or more amino acid replacement selected from the group consisting of Leu42→Pro; Pro 48→Leu; Gln49→Leu; Ile55→Thr; Lys75→Met; Asp77→Glu; Ile80→Thr; and Ser127→Gln.

In another embodiment, the hNGAL mutein includes with respect to the mature hNGAL wild type amino acid sequence the amino acid replacements:
  (a) Val33→Gln; Leu36→Arg; Ile41→Ala; Tyr52→Thr; Thr54→Gln; Ser68→Ala; Leu70→Arg; Trp79→Ala; Arg81 Met; Lys134→Ser; and Tyr138→Leu;
  (b) Val33 Gln; Leu36→Arg; Ile41→Ala; Tyr52→Thr; Thr54→Gln; Ser68→Ala; Leu70→Arg; Trp79→Leu; Arg81→Met; Lys134→Ser; and Tyr138→Len; or
  (c) Val33→Gln; Leu36→Arg; Ile41→Ala; Tyr52→Thr; Thr54→Gln; Ser68→Ala; Leu70→Arg; Trp79→Leu; Arg81→Met; Lys134→Ser; Thr136→Ser; and Tyr138→Leu.

In such an embodiment, the mutein may further include with respect to the mature hNGAL wild type amino acid sequence an amino acid replacement selected from the group consisting of Leu42→Pro, Pro48→Leu, Gln49→Leu, Ile55→Thr, Lys75→Met, Asp77→Glu, Ile80→Thr, and Ser127→Gln. The mutein may further include with respect to the mature hNGAL wild type amino acid sequence an amino acid replacement selected from the group consisting of Arg43→Pro, Glu44→Val, Glu44→Met, Lys46→Pro, Asp47→Glu, Lys50→Leu, Met51→Leu, Lys59→Arg, Asn65→Asp, Tyr78→His, Gly86→Ser, Ser87→Pro, Ser87→Phe, Lys98→Glu, Ser99→Asn, Leu103→Ile, Leu107→Phe, Val110→Met, and Val111→Ala.

In one embodiment of the present invention, the mutein comprises with respect to the mature hNGAL wild type amino acid sequence the amino acid replacements:
  (a) Val33→Gln; Leu36→Arg; Ile41→Ala; Tyr52→Thr; Thr54→Gln; Ser68→Ala; Leu70→Arg; Trp79→Ala; Ile80→Thr; Arg81→Met; Lys134→Ser; and Tyr138→Leu;
  (b) Val33→Gln; Leu36→Arg; Ile41→Ala; Tyr52→Thr; Thr54→Gln; Ser68→Ala; Leu70→Arg; Trp79→Leu; Ile80→Thr; Arg81→Met; Lys134→Ser; and Tyr138→Leu;
  (c) Val33→Gln; Leu36→Arg; Ile41→Ala; Tyr52→Thr; Thr54→Gln; Ser68→Ala; Leu70→Arg; Trp79→Leu; Ile80→Thr; Arg81→Met; Ser127→Gln; Lys134→Ser; and Tyr138→Leu;
  (d) Val33→Gln; Leu36→Arg; Ile41→Ala; Tyr52→Thr; Thr54→Gln; Ser68→Ala; Leu70→Arg; Trp79→Leu; Ile80→Thr; Arg81→Met; Lys134→Ser; Thr136→Ser; and Tyr138→Leu;
  (e) Val33→Gln; Leu36→Arg; Ile41→Ala; Tyr52→Thr; Thr54→Gln; Ser68→Ala; Leu70→Arg; Trp79→Leu; Ile80→Thr; Arg81→Met; Ser127→Gln; Lys134→Ser; Thr136→Ser; and Tyr138→Len;
  (f) Val33→Gln; Leu36→Arg; Ile41→Ala; Tyr52→Thr; Thr54→Gln; Ser68→Ala; Leu70→Arg; Asp77→Glu; Trp79→Len; Ile80→Thr; Arg81→Met; Ser127→Gln; Lys134→Ser; Thr136→Ser; and Tyr138→Leu;
  (g) Val33→Gln; Leu36→Arg; Ile41→Ala; Leu42→Pro; Pro48→Leu; Gln49→Leu; Tyr52→Thr; Thr54→Gln; Ile55→Thr; Ser68→Ala; Leu70→Arg; Lys75→Met; Asp77→Glu; Trp79→Leu; Ile80→Thr; Arg81→Met; Ser127→Gln; Lys134→Ser; Thr136→Ser; and Tyr138→Leu;
  (h) Val33→Gln; Leu36→Arg; Ile41→Ala; Leu42→Pro; Arg43→Pro; Glu44→Val; Lys46→Pro; Asp47→Glu; Pro48→Leu; Gln49→Leu; Lys50→Leu; Met51→Leu; Tyr52→Thr; Thr54→Gln; Ile55→Thr; Ser68→Ala; Leu70→Arg; Lys75→Met; Asp77→Glu; Trp79→Leu; Ile80→Thr; Arg81→Met; Ser127→Gln; Lys134→Ser; Thr136→Ser; and Tyr138→Leu;
  (i) Val33→Gln; Leu36→Arg; Ile41→Ala; Leu42→Pro; Arg43→Pro; Glu44→Val; Lys46→Pro; Asp47→Glu; Pro48→Leu; Gln49→Leu; Lys50→Leu; Met51→Leu; Tyr52→Thr; Thr54 Gln; Ile55→Thr; Asn65→Asp; Ser68→Ala; Leu70→Arg; Lys75→Met; Asp77→Glu; Trp79→Leu; Ile80→Thr; Arg81→Met; Lys98→Glu; Val110→Met; Ser127→Gln; Lys134→Ser; Thr136→Ser; and Tyr138→Leu;
  (j) Val33→Gln; Leu36→Arg; Ile41→Ala; Leu42→Pro; Arg43→Pro; Glu44→Val; Lys46→Pro; Asp47→Glu; Pro48→Leu; Gln49→Leu; Lys50→Leu; Met51→Leu; Tyr52→Thr; Thr54→Gln; Ile55→Thr; Asn65→Asp; Ser68→Ala; Leu70→Arg; Lys75→Met; Asp77→Glu; Trp79→Leu; Ile 80→Thr; Arg81→Met; Gly86→Ser; Ser127→Gln; Lys134→Ser; Thr136→Ser; and Tyr138→Leu;
  (k) Val33→Gln; Leu36→Arg; Ile41→Ala; Leu42→Pro; Arg43→Pro; Glu44→Met; Lys46→Pro; Asp47→Glu; Pro48→Leu; Gln49→Leu; Lys50→Leu; Met51→Leu; Tyr52→Thr; Thr54→Gln; Ile55→Thr; Asn65→Asp; Ser68→Ala; Leu70→Arg; Lys75→Met; Asp77→Glu; Trp79→Leu; Ile80→Thr; Arg81→Met; Gly86 Ser; Ser87→Pro; Ser99→Asn; Leu107→Phe; Ser127→Gln; Lys134→Ser; Thr136→Ser; and Tyr138→Leu;
  (l) Val33→Gln; Leu36→Arg; Ile41→Ala; Leu42→Pro; Arg43→Pro; Glu44→Val; Lys46→Pro; Asp47→Glu; Pro48→Leu; Gln49→Leu; Lys50→Leu; Met51→Leu; Tyr52→Thr; Thr54→Gln; Ile55→Thr; Lys59→Arg; Asn65→Asp; Ser68→Ala; Leu70→Arg; Lys75→Met; Asp77→Glu; Trp79→Leu; Ile80→Thr; Arg81→Met; Ser127→Gln; Lys134→Ser; Thr136→Ser; and Tyr138→Leu;
  (m) Val33→Gln; Leu36→Arg; Ile41→Ala; Leu42→Pro; Arg43→Pro; Glu44→Val; Lys46→Pro; Asp47→Glu; Pro48→Leu; Gln49→Leu; Lys50→Leu; Met51→Leu; Tyr52→Thr; Thr54→Gln; Ile55→Thr; Asn65→Asp; Ser68→Ala; Leu70→Arg; Lys75→Met; Asp77→Glu; Trp79→Len; Ile80→Thr; Arg81→Met; Ser87→Phe; Ser127→Gln; Lys134→Ser; Thr136→Ser; and Tyr138→Leu; or
  (n) Val33→Gln; Leu36→Arg; Ile41→Ala; Leu42→Pro; Arg43→Pro; Glu44→Val; Lys46→Pro; Asp47→Glu; Pro48→Leu; Gln49→Leu; Lys50→Leu; Met51→Leu; Tyr52→Thr; Thr54→Gln; Ile55→Thr; Ser68→Ala; Leu70→Arg; Lys75→Met; Asp77→Glu; Tyr78→His; Trp79→Leu; Ile80→Thr; Arg81→Met; Leu103→Ile;

Leu107→Phe; Val111→Ala; Ser127→Gln; Lys134→Ser; Thr136→Ser; and Tyr138→Leu.

In any of the afore-mentioned embodiments, the mutein may further include with respect to the mature hNGAL wild type amino acid sequence one, two or all three amino acid replacements selected from the group consisting of Glu28→His, Cys87→Ser, and Thr145→Ala.

The mutein may have an amino acid sequence selected from the group consisting of the sequences set forth in SEQ ID NOs. 2-10 and 28-34.

The hNGAL mutein binding cyclohexyl-DPTA may comprise, consists essentially of or consist of any one of the amino acid sequences set forth in SEQ ID NOs.: 2-10 or 28-34 or a fragment or variant thereof. In one embodiment, the mutein according to the invention comprises, consists essentially of or consists of the amino acid sequence set forth in SEQ ID NO: 8, 9, 10 or 28-34 or a fragment or variant thereof. In this regard, it is noted that all of the muteins disclosed herein can be linked, either N- or C-terminal to a affinity tag such as pentahistidine tag, a hexahistidine tag or a Streptag®. Thus, the present application encompasses also all explicitly and generic described muteins equipped with such tags.

The term "fragment" as used in the present invention in connection with the muteins of the invention relates to proteins or peptides derived from full-length mature hNGAL that are N-terminally and/or C-terminally shortened, i.e. lacking at least one of the N-terminal and/or C-terminal amino acids. Such fragments comprise preferably at least 10, more preferably 20, most preferably 30 or more consecutive amino acids of the primary sequence of mature hNGAL and are usually detectable in an immunoassay of mature hNGAL.

The term "variant" as used in the present invention relates to derivatives of a protein or peptide that comprise modifications of the amino acid sequence, for example by substitution, deletion, insertion or chemical modification. Preferably, such modifications do not reduce the functionality of the protein or peptide. Such variants include proteins, wherein one or more amino acids have been replaced by their respective D-stereoisomers or by amino acids other than the naturally occurring 20 amino acids, such as, for example, ornithine, hydroxyproline, citrulline, homoserine, hydroxylysine, norvaline. However, such substitutions may also be conservative, i.e. an amino acid residue is replaced with a chemically similar amino acid residue. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan.

Also included in the scope of the present invention are the above muteins, which have been altered with respect to their immunogenicity.

Cytotoxic T-cells recognize peptide antigens on the cell surface of an antigen-presenting cell in association with a class I major histocompatibility complex (MHC) molecule. The ability of the peptides to bind to MHC molecules is allele specific and correlates with their immunogenicity. In order to reduce immunogenicity of a given protein, the ability to predict which peptides in a protein have the potential to bind to a given MHC molecule is of great value. Approaches that employ a computational threading approach to identify potential T-cell epitopes have been previously described to predict the binding of a given peptide sequence to MHC class I molecules (Altuvia et al. (1995) *J. Mol. Biol.* 249: 244-250).

Such an approach may also be utilized to identify potential T-cell epitopes in the muteins of the invention and to make depending on its intended use a selection of a specific mutein on the basis of its predicted immunogenicity. It may be furthermore possible to subject peptide regions which have been predicted to contain T-cell epitopes to additional mutagenesis to reduce or eliminate these T-cell epitopes and thus minimize immunogenicity. The removal of amphipathic epitopes from genetically engineered antibodies has been described (Mateo et al. (2000) *Hybridoma* 19(6):463-471) and may be adapted to the muteins of the present invention.

The muteins thus obtained may possess a minimized immunogenicity, which is desirable for their use in therapeutic and diagnostic applications, such as those described below.

For some applications, it is also useful to employ the muteins of the invention in a conjugated form. Accordingly, the invention is also directed to lipocalin muteins which are conjugated to a conjungation partner that may be selected from the group consisting of an enzyme label, a colored label, a cytostatic agent, a label that can be photoactivated and which is suitable for use in photodynamic therapy, haptens, digoxigenin, biotin, a chemotherapeutic metal, or a chemotherapeutic metal, and colloidal gold, to name only a few evocative examples. The mutein may also be conjugated to an organic drug molecule. The conjugation can be carried out using any conventional coupling method known in the art.

In general, it is possible to label an hNGAL mutein described herein with any appropriate chemical substance or enzyme, which directly or indirectly generates a detectable compound or signal in a chemical, physical, optical, or enzymatic reaction. An example for a physical reaction and at the same time optical reaction/marker is the emission of fluorescence upon irradiation. Alkaline phosphatase, horseradish peroxidase or β-galactosidase are examples of enzyme labels (and at the same time optical labels) which catalyze the formation of chromogenic reaction products. In general, all labels commonly used for antibodies (except those exclusively used with the sugar moiety in the Fc part of immunoglobulins) can also be used for conjugation to the muteins of the present invention. The muteins of the invention may also be conjugated with any suitable therapeutically active agent, e.g., for the targeted delivery of such agents to a given cell, tissue or organ or for the selective targeting of cells, e.g., of tumor cells without affecting the surrounding normal cells. Examples of such therapeutically active agents include radionuclides, toxins, small organic molecules, and therapeutic peptides (such as peptides acting as agonists/antagonists of a cell surface receptor or peptides competing for a protein binding site on a given cellular target). Examples of suitable toxins include, but are not limited to pertussis-toxin, diphtheria toxin, ricin, saporin, pseudomonas exotoxin, calicheamicin or a derivative thereof, a taxoid, a maytansinoid, a tubulysin or a dolastatin analogue. The dolastatin analogue may be auristatin E, monomethylauristatin E, auristatin PYE and auristatin PHE. Examples of cytostatic agent include, but are not limited to Cisplatin, Carboplatin, Oxaliplatin, 5-Fluorouracil, Taxotere (Docetaxel), Paclitaxel, Anthracycline (Doxorubicin), Methotrexate, Vinblastin, Vincristine, Vindesine, Vinorelbine, Dacarbazine, Cyclophosphamide, Etoposide, Adriamycine, Camptotecine, Combretatastin A-4 related compounds, sulfonamides, oxadiazolines, benzo[b]thiophenessynthetic spiroketal pyrans, monotetrahydrofuran compounds, curacin and curacin derivatives, methoxyestradiol derivatives and Leucovorin. The lipocalin muteins of the invention may also be conjugated with therapeutically active nucleic acids such as antisense nucleic acid molecules, small interfering RNAs, micro RNAs or ribozymes. Such conjugates can be produced by methods well known in the art.

In one embodiment, the muteins of the invention may also be coupled to a targeting moiety that targets a specific body region in order to deliver the inventive muteins to a desired region or area within the body. One example wherein such modification may be desirable is the crossing of the blood-brain-barrier. In order to cross the blood-brain barrier, the muteins of the invention may be coupled to moieties that facilitate the active transport across this barrier (see Gaillard P J, et al. (2005) *International Congress Series.* 1277, 185-198 or Gaillard P J, et al. (2005) *Expert Opin Drug Deliv.* 2(2), 299-309). Such moieties are for example available under the trade name 2B-Trans™ (to-BBB technologies BV, Leiden, NL). Other exemplary targeting molecules to which the muteins of the present invention may be coupled include antibodies, antibody fragments or lipocalin muteins with affinity for a desired target molecule. The target molecule of the targeting moieties may, for example, be a cell-surface antigen. Cell-surface antigens may be specific for a cell or tissue type, such as, for example, cancer cells. Illustrative examples of such cell surface proteins are HER-2 or proteoglycans such as NEU-2.

As indicated above, a mutein of the invention may in some embodiments be conjugated to a moiety that extends the serum half-life of the mutein (in this regard see also PCT publication WO 2006/56464 where such conjugation strategies are described with references to muteins of human neutrophil gelatinase-associated lipocalin with binding affinity for CTLA-4). The moiety that extends the serum half-life may be a polyalkylene glycol molecule, hydroxyethyl starch, fatty acid molecules, such as palmitic acid (Vajo & Duckworth (2000) *Pharmacol. Rev.* 52, 1-9), an Fc part of an immunoglobulin, a CH3 domain of an immunoglobulin, a CH4 domain of an immunoglobulin, albumin or a fragment thereof, an albumin binding peptide, or an albumin binding protein, transferrin to name only a few. The albumin binding protein may be a bacterial albumin binding protein, an antibody, an antibody fragment including domain antibodies (see U.S. Pat. No. 6,696,245, for example), or a lipocalin mutein with binding activity for albumin. Accordingly, suitable conjugation partners for extending the half-life of a lipocalin mutein of the invention include albumin (Osborn et al. (2002) *J. Pharmacol. Exp. Ther.* 303, 540-548), or an albumin binding protein, for example, a bacterial albumin binding domain, such as the one of streptococcal protein G (König, T. and Skerra, A. (1998) *J. Immunol. Methods* 218, 73-83). Other examples of albumin binding peptides that can be used as conjugation partner are, for instance, those having a Cys-$Xaa_1$-$Xaa_2$-$Xaa_3$-$Xaa_4$-Cys consensus sequence, wherein $Xaa_1$ is Asp, Asn, Ser, Thr, or Trp; $Xaa_2$ is Asn, Gln, H is, Ile, Leu, or Lys; $Xaa_3$ is Ala, Asp, Phe, Trp, or Tyr; and $Xaa_4$ is Asp, Gly, Leu, Phe, Ser, or Thr as described in US patent application 2003/0069395 or Dennis et al. (Dennis et al. (2002) *J. Biol. Chem.* 277, 35035-35043).

In other embodiments, albumin itself or a biological active fragment of albumin can be used as conjugation partner of a lipocalin mutein of the invention. The term "albumin" comprises all mammal albumins such as human serum albumin or bovine serum albumin or rat albumin. The albumin or fragment thereof can be recombinantly produced as described in U.S. Pat. No. 5,728,553 or European patent applications EP 0 330 451 and EP 0 361 991. Recombinant human albumin (Recombumin®) for use as a protein stabilizer is for example available from Novozymes Delta Ltd. (Nottingham, UK).

If the albumin-binding protein is an antibody fragment it may be a domain antibody. Domain Antibodies (dAbs) are engineered to allow precise control over biophysical properties and in vivo half-life to create the optimal safety and efficacy product profile. Domain Antibodies are for example commercially available from Domantis Ltd. (Cambridge, UK and MA, USA).

Using transferrin as a moiety to extend the serum half-life of the muteins of the invention, the muteins can be genetically fused to the N or C terminus, or both, of non-glycosylated transferrin. Non-glycosylated transferrin has a half-life of 14-17 days, and a transferrin fusion protein will similarly have an extended half-life. The transferrin carrier also provides high bioavailability, biodistribution and circulating stability. This technology is commercially available from BioRexis (BioRexis Pharmaceutical Corporation, PA, USA). Recombinant human transferrin (DeltaFerrin™) for use as a protein stabilizer is also commercially available from Novozymes Delta Ltd. (Nottingham, UK).

If an Fc part of an immunoglobulin is used for the purpose to prolong the serum half-life of the muteins of the invention, the SynFusion™ technology, commercially available from Syntonix Pharmaceuticals, Inc (MA, USA), may be used. The use of this Fc-fusion technology allows the creation of longer-acting biopharmaceuticals and may for example consist of two copies of the mutein linked to the Fc region of an antibody to improve pharmacokinetics, solubility, and production efficiency.

Yet another alternative to prolong the half-life of a mutein of the invention is to fuse to the N- or C-terminus of a mutein of the invention long, unstructured, flexible glycine-rich sequences (for example poly-glycine with about 20 to 80 consecutive glycine residues). This approach disclosed in WO2007/038619, for example, has also been term "rPEG" (recombinant PEG).

If polyalkylene glycol is used as conjugation partner, the polyalkylene glycol can be substituted or unsubstituted. It can also be an activated polyalkylene derivative. Examples of suitable compounds are polyethylene glycol (PEG) molecules as described in WO 99/64016, in U.S. Pat. No. 6,177,074 or in U.S. Pat. No. 6,403,564 in relation to interferon, or as described for other proteins such as PEG-modified asparaginase, PEG-adenosine deaminase (PEG-ADA) or PEG-superoxide dismutase (see for example, Fuertges et al. (1990) The Clinical Efficacy of Poly (Ethylene Glycol)-Modified Proteins *J. Control. Release* 11, 139-148). The molecular weight of such a polymer, preferrably polyethylene glycol, may range from about 300 to about 70.000 Dalton, including, for example, polyethylene glycol with a molecular weight of about 10.000, of about 20.000, of about 30.000 or of about 40.000 Dalton. Moreover, as e.g. described in U.S. Pat. Nos. 6,500,930 or 6,620,413, carbohydrate oligo- and polymers such as starch or hydroxyethyl starch (HES) can be conjugated to a mutein of the invention for the purpose of serum half-life extension.

If one of the above moieties is conjugated to the hNGAL mutein of the invention, conjugation to an amino acid side chain can be advantageous. Suitable amino acid side chains may occur naturally in the amino acid sequence of hNGAL or may be introduced by mutagenesis. In case a suitable binding site is introduced via mutagenesis, one possibility is the replacement of an amino acid at the appropriate position by a cysteine residue. In one embodiment, such mutation includes the introduction of a Cys residue at least one of the sequence positions that correspond to sequence positions 14, 21, 60, 84, 88, 116, 141, 145, 143, 146 or 158 of the wild type sequence of hNGAL. The newly created cysteine residue at any of these positions can in the following be utilized to conjugate the mutein to moiety prolonging the serum half-life of the mutein, such as PEG or an activated derivative thereof.

In another embodiment, in order to provide suitable amino acid side chains for conjugating one of the above moieties to the muteins of the invention artificial amino acids may be introduced by mutagenesis. Generally, such artificial amino acids are designed to be more reactive and thus to facilitate the conjugation to the desired moiety. One example of such an artificial amino acid that may be introduced via an artificial tRNA is para-acetyl-phenylalanine.

For several applications of the muteins disclosed herein it may be advantageous to use them in the form of fusion proteins. In some embodiments, the inventive hNGAL mutein is fused at its N-terminus or its C-terminus to a protein, a protein domain or a peptide such as a signal sequence and/or an affinity tag.

For pharmaceutical applications a mutein of the invention may be fused to a fusion partner that extends the in vivo serum half-life of the mutein (see again PCT publication WO 2006/56464 where suitable fusion partner are described with references to muteins of human neutrophile gelatinase-associated lipocalin with binding affinity for CTLA-4). Similar to the conjugates described above, the fusion partner may be an Fc part of an immunoglobulin, a CH3 domain of an immunoglobulin, a CH4 domain of an immungloubulin, albumin, an albumin binding peptide or an albumin binding protein, to name only a few. Again, the albumin binding protein may be a bacterial albumin binding protein or a lipocalin mutein with binding activity for albumin. Accordingly, suitable fusion partners for extending the half-life of a lipocalin mutein of the invention include albumin (Osborn, B. L. et al. (2002) supra *J. Pharmacol. Exp. Ther.* 303, 540-548), or an albumin binding protein, for example, a bacterial albumin binding domain, such as the one of streptococcal protein G (König, T. and Skerra, A. (1998) supra *J. Immunol. Methods* 218, 73-83). The albumin binding peptides described in Dennis et al, supra (2002) or US patent application 2003/0069395 having a Cys-$Xaa_1$-$Xaa_2$-$Xaa_3$-$Xaa_4$-Cys consensus sequence, wherein $Xaa_1$ is Asp, Asn, Ser, Thr, or Trp; $Xaa_2$ is Asn, Gln, His, Ile, Leu, or Lys; $Xaa_3$ is Ala, Asp, Phe, Trp, or Tyr; and $Xaa_4$ is Asp, Gly, Leu, Phe, Ser, or Thr can also be used as fusion partner. It is also possible to use albumin itself or a biological active fragment of albumin as fusion partner of a lipocalin mutein of the invention. The term "albumin" comprises all mammal albumins such as human serum albumin or bovine serum albumin or rat serum albumin. The recombinant production of albumin or fragments thereof is well known in the art and for example described in U.S. Pat. No. 5,728,553, European patent application EP 0 330 451 or EP 0 361 991.

The fusion partner may confer new characteristics to the inventive lipocalin mutein such as enzymatic activity or binding affinity for other molecules. Examples of suitable fusion proteins are alkaline phosphatase, horseradish peroxidase, gluthation-S-transferase, the albumin-binding domain of protein G, protein A, antibody fragments, oligomerization domains, lipocalin muteins of same or different binding specificity (which results in the formation of "duocalins", cf. Schlehuber, S., and Skerra, A. (2001), Duocalins, engineered ligand-binding proteins with dual specificity derived from the lipocalin fold Biol. Chem. 382, 1335-1342), or toxins.

In particular, it may be possible to fuse a lipocalin mutein of the invention with a separate enzyme active site such that both "components" of the resulting fusion protein together act on a given therapeutic target. The binding domain of the lipocalin mutein attaches to the disease-causing target, allowing the enzyme domain to abolish the biological function of the target.

Affinity tags such as the Strep-tag® or Strep-tag® II (Schmidt, T. G. M. et al. (1996) *J. Mol. Biol.* 255, 753-766), the myc-tag, the FLAG-tag, the $His_6$-tag or the HA-tag or proteins such as glutathione-S-transferase also allow easy detection and/or purification of recombinant proteins are further examples of preferred fusion partners. Finally, proteins with chromogenic or fluorescent properties such as the green fluorescent protein (GFP) or the yellow fluorescent protein (YFP) are suitable fusion partners for a lipocalin mutein of the invention as well.

The term "fusion protein" as used herein also comprises lipocalin muteins according to the invention containing a signal sequence. Signal sequences at the N-terminus of a polypeptide direct this polypeptide to a specific cellular compartment, for example the periplasm of *E. coli* or the endoplasmatic reticulum of eukaryotic cells. A large number of signal sequences is known in the art. A preferred signal sequence for secretion a polypeptide into the periplasm of *E. coli* is the OmpA-signal sequence.

The present invention also relates to nucleic acid molecules (DNA and RNA) comprising nucleotide sequences coding for muteins as described herein. Since the degeneracy of the genetic code permits substitutions of certain codons by other codons specifying the same amino acid, the invention is not limited to a specific nucleic acid molecule encoding a mutein of the invention but includes all nucleic acid molecules comprising nucleotide sequences encoding a functional mutein.

Therefore, the present invention also includes a nucleic acid sequence encoding a mutein according to the invention including a mutation at least one codon of any of the amino acid sequence positions 33, 36, 41, 52, 54, 68, 70, 79, 81, 134, 136 and 138 of the linear polypeptide sequence of hNGAL.

The invention as disclosed herein also includes nucleic acid molecules encoding hNGAL muteins, which comprise additional mutations outside the indicated sequence positions of experimental mutagenesis. Such mutations are often tolerated or can even prove to be advantageous, for example if they contribute to an improved folding efficiency, serum stability, thermal stability or ligand binding affinity of the mutein.

A nucleic acid molecule disclosed in this application may be "operably linked" to a regulatory sequence (or regulatory sequences) to allow expression of this nucleic acid molecule.

A nucleic acid molecule, such as DNA, is referred to as "capable of expressing a nucleic acid molecule" or capable "to allow expression of a nucleotide sequence" if it comprises sequence elements which contain information regarding to transcriptional and/or translational regulation, and such sequences are "operably linked" to the nucleotide sequence encoding the polypeptide. An operable linkage is a linkage in which the regulatory sequence elements and the sequence to be expressed are connected in a way that enables gene expression. The precise nature of the regulatory regions necessary for gene expression may vary among species, but in general these regions comprise a promoter which, in prokaryotes, contains both the promoter per se, i.e. DNA elements directing the initiation of transcription, as well as DNA elements which, when transcribed into RNA, will signal the initiation of translation. Such promoter regions normally include 5' non-coding sequences involved in initiation of transcription and translation, such as the −35/−10 boxes and the Shine-Dalgarno element in prokaryotes or the TATA box, CAAT sequences, and 5'-capping elements in eukaryotes. These regions can also include enhancer or repressor elements as well as translated signal and leader sequences for targeting the native polypeptide to a specific compartment of a host cell.

In addition, the 3' non-coding sequences may contain regulatory elements involved in transcriptional termination, polyadenylation or the like. If, however, these termination sequences are not satisfactory functional in a particular host cell, then they may be substituted with signals functional in that cell.

Therefore, a nucleic acid molecule of the invention can include a regulatory sequence, preferably a promoter sequence. In another preferred embodiment, a nucleic acid molecule of the invention comprises a promoter sequence and a transcriptional termination sequence. Suitable prokaryotic promoters are, for example, the tet promoter, the lacUV5 promoter or the T7 promoter. Examples of promoters useful for expression in eukaryotic cells are the SV40 promoter or the CMV promoter.

The nucleic acid molecules of the invention can also be part of a vector or any other kind of cloning vehicle, such as a plasmid, a phagemid, a phage, a baculovirus, a cosmid or an artificial chromosome.

In one embodiment, the nucleic acid molecule is comprised in a phasmid. A phasmid vector denotes a vector encoding the intergenic region of a temperent phage, such as M13 or f1, or a functional part thereof fused to the cDNA of interest. After superinfection of the bacterial host cells with such an phagemid vector and an appropriate helper phage (e.g. M13K07, VCS-M13 or R408) intact phage particles are produced, thereby enabling physical coupling of the encoded heterologous cDNA to its corresponding polypeptide displayed on the phage surface (reviewed, e.g., in Kay, B. K. et al. (1996) *Phage Display of Peptides and Proteins—A Laboratory Manual*, 1st Ed., Academic Press, New York N.Y.; Lowman, H. B. (1997) *Annu. Rev. Biophys. Biomol. Struct.* 26, 401-424, or Rodi, D. J., and Makowski, L. (1999) *Curr. Opin. Biotechnol.* 10, 87-93).

Such cloning vehicles can include, aside from the regulatory sequences described above and a nucleic acid sequence encoding a lipocalin mutein of the invention, replication and control sequences derived from a species compatible with the host cell that is used for expression as well as selection markers conferring a selectable phenotype on transformed or transfected cells. Large numbers of suitable cloning vectors are known in the art, and are commercially available.

The DNA molecule encoding lipocalin muteins of the invention, and in particular a cloning vector containing the coding sequence of such a lipocalin mutein can be transformed into a host cell capable of expressing the gene. Transformation can be performed using standard techniques (Sambrook, J. et al. (1989), supra).

Thus, the invention is also directed to a host cell containing a nucleic acid molecule as disclosed herein.

The transformed host cells are cultured under conditions suitable for expression of the nucleotide sequence encoding a fusion protein of the invention. Suitable host cells can be prokaryotic, such as *Escherichia coli* (*E. coli*) or *Bacillus subtilis*, or eukaryotic, such as *Saccharomyces cerevisiae*, *Pichia pastoris*, SF9 or High5 insect cells, immortalized mammalian cell lines (e.g. HeLa cells or CHO cells) or primary mammalian cells The invention also relates to a method for the production of a mutein of the invention, wherein the mutein, a fragment of the mutein or a fusion protein of the mutein and another polypeptide is produced starting from the nucleic acid coding for the mutein by means of genetic engineering methods. The method can be carried out in vivo, the mutein can for example be produced in a bacterial or eucaryotic host organism and then isolated from this host organism or its culture. It is also possible to produce a protein in vitro, for example by use of an in vitro translation system.

When producing the mutein in vivo a nucleic acid encoding a mutein of the invention is introduced into a suitable bacterial or eukaryotic host organism by means of recombinant DNA technology (as already outlined above). For this purpose, the host cell is first transformed with a cloning vector comprising a nucleic acid molecule encoding a mutein of the invention using established standard methods (Sambrook, J. et al. (1989), supra). The host cell is then cultured under conditions, which allow expression of the heterologous DNA and thus the synthesis of the corresponding polypeptide. Subsequently, the polypeptide is recovered either from the cell or from the cultivation medium.

In one aspect, the present invention relates to a method for the generation of a mutein of the invention, comprising:
(a) subjecting a nucleic acid molecule encoding an hNGAL protein to mutagenesis at a nucleotide triplet coding for at least one of any of the sequence positions corresponding to the sequence positions 33, 36, 41, 52, 54, 68, 70, 79, 81, 134, 136, and 138 of the linear polypeptide sequence of hNGAL, resulting in one or more mutein nucleic acid molecule(s)
(b) expressing the one more mutein nucleic acid molecule(s) obtained in (a) in a suitable expression system, and
(c) enriching the one or more mutein(s) having a detectable binding affinity for a given target by means of selection and/or isolation.

The term "mutagenesis" as used herein means that the experimental conditions are chosen such that the amino acid naturally occurring at a given sequence position of hNGAL (Swiss-Prot data bank entry P80188) can be substituted by at least one amino acid that is not present at this specific position in the respective natural polypeptide sequence. The term "mutagenesis" also includes the (additional) modification of the length of sequence segments by deletion or insertion of one or more amino acids. Thus, it is within the scope of the invention that, for example, one amino acid at a chosen sequence position is replaced by a stretch of three random mutations, leading to an insertion of two amino acid residues compared to the length of the respective segment of the wild type protein. Such an insertion of deletion may be introduced independently from each other in any of the peptide segments that can be subjected to mutagenesis in the invention. In one exemplary embodiment of the invention, an insertion of several mutations may be introduced into the loop AB of the chosen lipocalin scaffold (cf. International Patent Application WO 2005/019256 which is incorporated by reference its entirety herein). The term "random mutagenesis" means that no predetermined single amino acid (mutation) is present at a certain sequence position but that at least two amino acids can be incorporated with a certain probability at a predefined sequence position during mutagenesis.

The coding sequence of hNGAL is used as a starting point for the mutagenesis of the peptide segments selected in the present invention. For the mutagenesis of the recited amino acid positions, the person skilled in the art has at his disposal the various established standard methods for site-directed mutagenesis (Sambrook, J. et al. (1989), supra). A commonly used technique is the introduction of mutations by means of PCR (polymerase chain reaction) using mixtures of synthetic oligonucleotides, which bear a degenerate base composition at the desired sequence positions. For example, use of the codon NNK or NNS (wherein N=adenine, guanine or cytosine or thymine; K=guanine or thymine; S=adenine or cytosine) allows incorporation of all 20 amino acids plus the amber stop codon during mutagenesis, whereas the codon VVS limits the number of possibly incorporated amino acids to 12, since it excludes the amino acids Cys, Ile, Leu, Met, Phe, Trp, Tyr, Val from being incorporated into the selected position of the polypeptide sequence; use of the codon NMS (wherein M=adenine or cytosine), for example, restricts the number of possible amino acids to 11 at a selected sequence position since it excludes the amino acids Arg, Cys, Gly, Ile, Leu, Met, Phe, Trp, Val from being incorporated at a selected sequence position. In this respect it is noted that codons for other amino acids (than the regular 20 naturally occurring amino acids) such as selenocystein or pyrrolysine can also be incorporated into a nucleic acid of a mutein. It is also possible, as described by Wang, L., et al. (2001) *Science* 292, 498-500, or Wang, L., and Schultz, P. G. (2002) *Chem. Comm.* 1, 1-11, to use "artificial" codons such as UAG which are usually recognized as stop codons in order to insert other unusual amino acids, for example o-methyl-L-tyrosine or p-aminophenylalanine.

The use of nucleotide building blocks with reduced base pair specificity, as for example inosine, 8-oxo-2' deoxyguanosine or 6(2-deoxy-β-D-ribofuranosyl)-3,4-dihydro-8H-pyrimindo-1,2-oxazine-7-one (Zaccolo et al. (1996) *J. Mol. Biol.* 255, 589-603), is another option for the introduction of mutations into a chosen sequence segment.

A further possibility is the so-called triplet-mutagenesis. This method uses mixtures of different nucleotide triplets, each of which codes for one amino acid, for incorporation into the coding sequence (Virnekäs B, Ge L, Plückthun A, Schneider K C, Wellnhofer G, Moroney S E. 1994 Trinucleotide phosphoramidites: ideal reagents for the synthesis of mixed oligonucleotides for random mutagenesis. *Nucleic Acids Res* 22, 5600-5607).

One possible strategy for introducing mutations in the selected regions of the respective polypeptides is based on the use of four oligonucleotides, each of which is partially derived from one of the corresponding sequence segments to be mutated. When synthesizing these oligonucleotides, a person skilled in the art can employ mixtures of nucleic acid building blocks for the synthesis of those nucleotide triplets which correspond to the amino acid positions to be mutated so that codons encoding all natural amino acids randomly arise, which at last results in the generation of a lipocalin peptide library. For example, the first oligonucleotide corresponds in its sequence—apart from the mutated positions—to the coding strand for the peptide segment to be mutated at the most N-terminal position of the lipocalin polypeptide. Accordingly, the second oligonucleotide corresponds to the non-coding strand for the second sequence segment following in the polypeptide sequence. The third oligonucleotide corresponds in turn to the coding strand for the corresponding third sequence segment. Finally, the fourth oligonucleotide corresponds to the non-coding strand for the fourth sequence segment. A polymerase chain reaction can be performed with the respective first and second oligonucleotide and separately, if necessary, with the respective third and fourth oligonucleotide.

The amplification products of both of these reactions can be combined by various known methods into a single nucleic acid comprising the sequence from the first to the fourth sequence segments, in which mutations have been introduced at the selected positions. To this end, both of the products can for example be subjected to a new polymerase chain reaction using flanking oligonucleotides as well as one or more mediator nucleic acid molecules, which contribute the sequence between the second and the third sequence segment. In the choice of the number and arrangement within the sequence of the oligonucleotides used for the mutagenesis, the person skilled in the art has numerous alternatives at his disposal.

The nucleic acid molecules defined above can be connected by ligation with the missing 5'- and 3'-sequences of a nucleic acid encoding a lipocalin polypeptide and/or the vector, and can be cloned in a known host organism. A multitude of established procedures are available for ligation and cloning (Sambrook, J. et al. (1989), supra). For example, recognition sequences for restriction endonucleases also present in the sequence of the cloning vector can be engineered into the sequence of the synthetic oligonucleotides. Thus, after amplification of the respective PCR product and enzymatic cleavage the resulting fragment can be easily cloned using the corresponding recognition sequences.

Longer sequence segments within the gene coding for the protein selected for mutagenesis can also be subjected to random mutagenesis via known methods, for example by use of the polymerase chain reaction under conditions of increased error rate, by chemical mutagenesis or by using bacterial mutator strains. Such methods can also be used for further optimization of the target affinity or specificity of a lipocalin mutein. Mutations possibly occurring outside the segments of experimental mutagenesis are often tolerated or can even prove to be advantageous, for example if they contribute to an improved folding efficiency or folding stability of the lipocalin mutein.

According to one embodiment of the present invention, the above method includes subjecting the nucleic acid molecule encoding an hNGAL protein to mutagenesis at least 9, 10, 11 or all 12 nucleotide triplets coding for any of the above indicated sequence positions of hNGAL.

In one further embodiment, the method further includes subjecting the nucleic acid molecule to mutagenesis at least one nucleotide triplet coding for any of the sequence positions corresponding to the sequence positions 42, 48, 49, 55, 75, 77, 80, and 127 of the linear polypeptide sequence of hNGAL. The method may further include subjecting the nucleic acid molecule to mutagenesis at least one nucleotide triplet coding for any of the sequence positions corresponding to the sequence positions 43, 44, 46, 47, 50, 51, 59, 65, 78, 86, 87, 98, 99, 103, 107, 110 and 111 of the linear polypeptide sequence of hNGAL.

In still another embodiment of the present invention, the method further includes subjecting the nucleic acid molecule to mutagenesis at nucleotide triplets coding for at least any 9 of the sequence positions corresponding to the sequence positions 33, 36, 41, 42, 48, 49, 52, 54, 55, 68, 70, 75, 77, 79, 80, 81, 127, 134, 136 and 138 of the linear polypeptide sequence of hNGAL.

In a still further embodiment, the method includes subjecting the nucleic acid molecule to mutagenesis at nucleotide triplets coding for at least any 9 of the sequence positions corresponding to the sequence positions 33, 36, 41, 42, 43, 44, 46, 47, 48, 49, 50, 51, 52, 54, 55, 59, 65, 68, 70, 75, 77, 78, 79, 80, 81, 86, 87, 98, 99, 103, 107, 110, 111, 127, 134, 136 and 138 of the linear polypeptide sequence of hNGAL.

According to the method of the invention a mutein is obtained starting from a nucleic acid encoding hNGAL. Such a nucleic acid is subjected to mutagenesis and introduced into a suitable bacterial or eukaryotic host organism by means of recombinant DNA technology. Obtaining a nucleic acid library of hNGAL can be carried out using any suitable technique that is known in the art for generating lipocalin muteins with antibody-like properties, i.e. muteins that have affinity towards a given target. Examples of such combinatorial methods are described in detail in the international patent applications WO 99/16873, WO 00/75308, WO 03/029471, WO 03/029462, WO 03/029463, WO 2005/019254, WO 2005/019255, WO 2005/019256, or WO 2006/56464 for instance. The content of each of these patent applications is incorporated by reference herein in its entirety. After expression of the nucleic acid sequences that were subjected to mutagenesis in an appropriate host, the clones carrying the genetic information for the plurality of respective lipocalin muteins, which bind a given target can be selected from the library obtained. Well known techniques can be employed for the selection of these clones, such as phage display (reviewed in Kay, B. K. et al. (1996) supra; Lowman, H. B. (1997) supra or Rodi, D. J., and Makowski, L. (1999) supra), colony screening (reviewed in Pini, A. et al. (2002) *Comb. Chem. High Throughput Screen.* 5, 503-510), ribosome display (reviewed in Amstutz, P. et al. (2001) *Curr. Opin. Biotechnol.* 12, 400-405) or mRNA display as reported in Wilson, D. S. et al. (2001) *Proc. Natl. Acad. Sci. USA* 98, 3750-3755 or the methods specifically described in WO 99/16873, WO 00/75308, WO 03/029471, WO 03/029462, WO 03/029463, WO 2005/019254, WO 2005/019255, WO 2005/019256, or WO 2006/56464.

In accordance with this disclosure, step (c) further comprises in another embodiment of the above methods:
  (i) providing as a given ligand a compound selected from the group consisting of a chemical compound in free or conjugated form that exhibits features of an immunological hapten, a peptide, a protein or another macromolecule such as a polysaccharide, a nucleic acid molecule (DNA or RNA, for example) or an entire virus particle or viroid, for example,
  (ii) contacting the plurality of muteins with said ligand in order to allow formation of complexes between said ligand and muteins having binding affinity for said ligand, and
  (iii) removing muteins having no or no substantial binding affinity.

In specific embodiments of the invention, the ligand may be a small organic molecule, such as a metal-chelating agent.

In one embodiment of the methods of the invention, the selection in step (c) is carried out under competitive conditions. Competitive conditions as used herein means that selection of muteins encompasses at least one step in which the muteins and the given non-natural ligand of hNGAL (target) are brought in contact in the presence of an additional ligand, which competes with binding of the muteins to the target. This additional ligand may be a physiological ligand of the target, an excess of the target itself or any other non-physiological ligand of the target that binds at least an overlapping epitope to the epitope recognized by the muteins of the invention and thus interferes with target binding of the muteins. Alternatively, the additional ligand competes with binding of the muteins by complexing an epitope distinct from the binding site of the muteins to the target by allosteric effects.

An embodiment of the phage display technique (reviewed in Kay, B. K. et al. (1996), supra; Lowman, H. B. (1997) supra or Rodi, D. J., and Makowski, L. (1999), supra) using temperent M13 phage is given as an example of a selection method that can be employed in the present invention. Another embodiment of the phage display technology that can be used for selection of muteins of the invention is the hyperphage phage technology as described by Broders et al. (Broders et al. (2003) "Hyperphage. Improving antibody presentation in phage display." *Methods Mol. Biol.* 205:295-302). Other temperent phage such as f1 or lytic phage such as T7 may be employed as well. For the exemplary selection method, M13 phagemids are produced which allow the expression of the mutated lipocalin nucleic acid sequence as a fusion protein with a signal sequence at the N-terminus, preferably the OmpA-signal sequence, and with the capsid protein pIII of the phage M13 or fragments thereof capable of being incorporated into the phage capsid at the C-terminus.

The C-terminal fragment ΔpIII of the phage capsid protein comprising amino acids 217 to 406 of the wild type sequence is preferably used to produce the fusion proteins. Especially preferred in one embodiment is a C-terminal fragment of pIII, in which the cysteine residue at position 201 is missing or is replaced by another amino acid.

Accordingly, a further embodiment of the methods of the invention involves operably fusing a nucleic acid coding for the plurality of muteins of hNGAL and resulting from mutagenesis at the 3' end with a gene coding for the coat protein pIII of a filamentous bacteriophage of the M13-family or for a fragment of this coat protein, in order to select at least one mutein for the binding of a given ligand.

The fusion protein may comprise additional components such as an affinity tag, which allows the immobilization, detection and/or purification of the fusion protein or its parts. Furthermore, a stop codon can be located between the sequence regions encoding the lipocalin or its muteins and the phage capsid gene or fragments thereof, wherein the stop codon, preferably an amber stop codon, is at least partially translated into an amino acid during translation in a suitable suppressor strain.

For example, the phasmid vector pTLPC27, now also called pTlc27 that is described here can be used for the preparation of a phagemid library encoding hNGAL muteins. The inventive nucleic acid molecules coding for the hNGAL muteins are inserted into the vector using the two BstXI restriction sites. After ligation a suitable host strain such as *E. coli* XL1-Blue is transformed with the resulting nucleic acid mixture to yield a large number of independent clones. A respective vector can be generated for the preparation of a hyperphagemid library, if desired.

The resulting library is subsequently superinfected in liquid culture with an appropriate M13-helper phage or hyperphage in order to produce functional phagemids. The recombinant phagemid displays the lipocalin mutein on its surface as a fusion with the coat protein pIII or a fragment thereof, while the N-terminal signal sequence of the fusion protein is normally cleaved off. On the other hand, it also bears one or more copies of the native capsid protein pIII supplied by the helper phage and is thus capable of infecting a recipient, in general a bacterial strain carrying an F- or F'-plasmid. In case of hyperphage display, the hyperphagemids display the lipocalin muteins on their surface as a fusion with the infective coat protein pIII but no native capsid protein. During or after infection with helper phage or hyperphage, gene expression of the fusion protein between the lipocalin mutein and the capsid protein pIII can be induced, for example by addition of anhydrotetracycline. The induction conditions are chosen such that a substantial fraction of the phagemids obtained displays at least one lipocalin mutein on their surface. In case of hyperphage display induction conditions result in a population of hyperphagemids carrying between three and five fusion proteins consisting of the lipocalin mutein and the capsid protein pIII. Various methods are known for isolating the phagemids, such as precipitation with polyethylene glycol. Isolation typically occurs after an incubation period of 6-8 hours.

The isolated phasmids can then be subjected to selection by incubation with the desired target, wherein the target is presented in a form allowing at least temporary immobilization of those phagemids which carry muteins with the desired binding activity as fusion proteins in their coat. Among the various embodiments known to the person skilled in the art, the target can, for example, be conjugated with a carrier protein such as serum albumin and be bound via this carrier protein to a protein binding surface, for example polystyrene.

Microtiter plates suitable for ELISA techniques or so-called "immuno-sticks" can preferrably be used for such an immobilization of the target. Alternatively, conjugates of the target with other binding groups, such as biotin, can be used. The target can then be immobilized on a surface which selectively binds this group, for example microtiter plates or paramagnetic particles coated with streptavidin, neutravidin or avidin. If the target is fused to an Fc portion of an immunoglobulin, immobilization can also be achieved with surfaces, for example microtiter plates or paramagnetic particles, which are coated with protein A or protein G.

Non-specific phagemid-binding sites present on the surfaces can be saturated with blocking solutions as they are known for ELISA methods. The phagemids are then typically brought into contact with the target immobilized on the surface in the presence of a physiological buffer. Unbound phagemids are removed by multiple washings. The phagemid particles remaining on the surface are then eluted. For elution, several methods are possible. For example, the phagemids can be eluted by addition of proteases or in the presence of acids, bases, detergents or chaotropic salts or under moderately denaturing conditions. A preferred method is the elution using buffers of pH 2.2, wherein the eluate is subsequently neutralized. Alternatively, a solution of the free target can be added in order to compete with the immobilized target for binding to the phagemids or target-specific phagemids can be eluted by competition with immunoglobulins or natural liganding proteins which specifically bind to the target of interest.

Afterwards, E. coli cells are infected with the eluted phagemids. Alternatively, the nucleic acids can be extracted from the eluted phagemids and used for sequence analysis, amplification or transformation of cells in another manner. Starting from the E. coli clones obtained in this way, fresh phagemids or hyperphagemids are again produced by superinfection with M13 helper phages or hyperphage according to the method described above and the phagemids amplified in this way are once again subjected to a selection on the immobilized target. Multiple selection cycles are often necessary in order to obtain the phagemids with the muteins of the invention in sufficiently enriched form. The number of selection cycles is preferably chosen such that in the subsequent functional analysis at least 0.1% of the clones studied produce muteins with detectable affinity for the given target. Depending on the size, i.e. the complexity of the library employed, 2 to 8 cycles are typically required to this end.

For the functional analysis of the selected muteins, an E. coli strain is infected with the phagemids obtained from the selection cycles and the corresponding double stranded phasmid DNA is isolated. Starting from this phasmid DNA, or also from the single-stranded DNA extracted from the phagemids, the nucleic acid sequences of the selected muteins of the invention can be determined by the methods known in the art and the amino acid sequence can be deduced therefrom. The mutated region or the sequence of the entire hNGAL mutein can be subcloned on another expression vector and expressed in a suitable host organism. For example, the vector pTLPC26 now also called pTlc26 can be used for expression in E. coli strains such as E. coli TG1. The muteins of hNGAL thus produced can be purified by various biochemical methods. The hNGAL muteins produced, for example with pTlc26, carry the affinity peptide Strep-tag II (Schmidt et al., supra) at their C-termini and can therefore preferably be purified by streptavidin affinity chromatography.

The selection can also be carried out by means of other methods. Many corresponding embodiments are known to the person skilled in the art or are described in the literature.

Moreover, a combination of methods can be applied. For example, clones selected or at least enriched by "phage display" can additionally be subjected to "colony screening". This procedure has the advantage that individual clones can directly be isolated with respect to the production of an hNGAL mutein with detectable binding affinity for a target.

In addition to the use of E. coli as host organism in the "phage display" technique or the "colony screening" method, other bacterial strains, yeast or also insect cells or mammalian cells can be used for this purpose. Further to the selection of an hNGAL mutein from a random library as described above, evolutive methods including limited mutagenesis can also be applied in order to optimize a mutein that already possesses some binding activity for the target with respect to affinity or specificity for the target after repeated.

Once a mutein with affinity to a given target has been selected, it is additionally possible to subject such a mutein to another mutagenesis in order to subsequently select variants of even higher affinity or variants with improved properties such as higher thermostability, improved serum stability, thermodynamic stability, improved solubility, improved monomeric behavior, improved resistance against thermal denaturation, chemical denaturation, proteolysis, or detergents etc. This further mutagenesis, which in case of aiming at higher affinity can be considered as in vitro "affinity maturation", can be achieved by site specific mutation based on rational design or a random mutation. Another possible approach for obtaining a higher affinity or improved properties is the use of error-prone PCR, which results in point mutations over a selected range of sequence positions of the lipocalin mutein. The error-prone PCR can be carried out in accordance with any known protocol such as the one described by Zaccolo et al. (1996) *J. Mol. Biol.* 255, 589-603. Other methods of random mutagenesis that are suitable for such purposes include random insertion/deletion (RID) mutagenesis as described by Murakami et al. (2002) *Nat. Biotechnol.* 20, 76-81 or nonhomologous random recombination (NRR) as described by Bittker et al. (2002) *Nat. Biotechnol.* 20, 1024-1029. If desired, affinity maturation can also be carried out according to the procedure described in WO 00/75308 or Schlehuber et al. (2000) *J. Mol. Biol.* 297, 1105-1120, where muteins of the bilin-binding protein having high affinity to digoxigenin were obtained. A further approach for improving the affinity is to carry out positional saturation mutagenesis. In this approach "small" nucleic acid libraries can be created in which amino acid exchanges/mutations are only introduced at single positions within any of the four loop segments. These libraries are then directly subjected to a selection step (affinity screening) without further rounds of panning. This approach allows the identification of residues that contribute to improved binding of the desired target and allows identification of "hot spots" that are important for the binding.

In one embodiment, the above method for modifying a mutein further includes introducing a Cys residue at least one of any of the sequence positions that correspond to sequence positions 14, 21, 60, 84, 88, 116, 141, 145, 143, 146 or 158 of the wild type sequence of hNGAL and coupling a moiety that is able to modify the serum half time of said mutein via the thiol group of a Cys residue introduced at least one of any of the sequence positions that correspond to sequence positions 14, 21, 60, 84, 88, 116, 141, 145, 143, 146 or 158 of the wild type sequence of hNGAL. The moiety that is able to modify the serum half time of said mutein may be selected from the group consisting of a polyalkylene glycol molecule and hydroxyethylstarch.

In a further aspect, the present invention is directed to a mutein of hNGAL having detectable binding affinity to a given non-natural ligand of hNGAL, which is obtainable by or obtained by the above-detailed methods of the invention.

In some hNGAL muteins of the invention, the naturally occurring disulfide bond between Cys 76 and Cys 175 is removed. Accordingly, such muteins (or any other hNGAL mutein that does not comprise an intramolecular disulfide bond) can be produced in a cell compartment having a reducing redox milieu, for example, in the cytoplasma of Gram-negative bacteria.

In case a lipocalin mutein of the invention comprises intramolecular disulfide bonds, it may be preferred to direct the nascent polypeptide to a cell compartment having an oxidizing redox milieu using an appropriate signal sequence. Such an oxidizing environment may be provided by the periplasm of Gram-negative bacteria such as E. coli, in the extracellular milieu of Gram-positive bacteria or in the lumen of the endoplasmatic reticulum of eukaryotic cells and usually favors the formation of structural disulfide bonds.

It is, however, also possible to produce a mutein of the invention in the cytosol of a host cell, preferably E. coli. In this case, the polypeptide can either be directly obtained in a soluble and folded state or recovered in form of inclusion bodies, followed by renaturation in vitro. A further option is the use of specific host strains having an oxidizing intracellular milieu, which may thus allow the formation of disulfide bonds in the cytosol (Venturi et al. (2002) *J. Mol. Biol.* 315, 1-8.).

However, a mutein of the invention may not necessarily be generated or produced only by use of genetic engineering. Rather, a lipocalin mutein can also be obtained by chemical synthesis such as Merrifield solid phase polypeptide synthesis or by in vitro transcription and translation. It is for example possible that promising mutations are identified using molecular modeling and then to synthesize the wanted (designed) polypeptide in vitro and investigate the binding activity for a given target. Methods for the solid phase and/or solution phase synthesis of proteins are well known in the art (reviewed, e.g., in Lloyd-Williams et al. (1997) *Chemical Approaches to the Synthesis of Peptides and Proteins.* CRC Press, Boca Raton, Fields, GB, and Colowick (1997) *Solid-Phase Peptide Synthesis*, Academic Press, San Diego, or Bruckdorfer et al. (2004) *Curr. Pharm. Biotechnol.* 5, 29-43).

In another embodiment, the muteins of the invention may be produced by in vitro transcription/translation employing well-established methods known to those skilled in the art.

The invention also relates to a pharmaceutical composition comprising at least one inventive mutein of hNGAL or a fusion protein or conjugate thereof and, optionally, a pharmaceutically acceptable excipient.

The lipocalin muteins according to the invention can be administered via any parenteral or non-parenteral (enteral) route that is therapeutically effective for proteinaceous drugs. Parenteral application methods comprise, for example, intracutaneous, subcutaneous, intramuscular or intravenous injection and infusion techniques, e.g. in the form of injection solutions, infusion solutions or tinctures, as well as aerosol installation and inhalation, e.g. in the form of aerosol mixtures, sprays or powders. Non-parenteral delivery modes are, for instance, orally, e.g. in the form of pills, tablets, capsules, solutions or suspensions, or rectally, e.g. in the form of suppositories. The muteins of the invention can be administered systemically or topically in formulations containing conventional non-toxic pharmaceutically acceptable excipients or carriers, additives and vehicles as desired.

In one embodiment of the present invention the pharmaceutical is administered parenterally to a mammal, and in particular to humans. Corresponding administration methods include, but are not limited to, for example, intracutaneous, subcutaneous, intramuscular or intravenous injection and infusion techniques, e.g. in the form of injection solutions, infusion solutions or tinctures as well as aerosol installation and inhalation, e.g. in the form of aerosol mixtures, sprays or powders. A combination of intravenous and subcutaneous infusion and/or injection might be most convenient in case of compounds with a relatively short serum half life. The pharmaceutical composition may be an aqueous solution, an oil-in water emulsion or a water-in-oil emulsion.

In this regard it is noted that transdermal delivery technologies, e.g. iontophoresis, sonophoresis or microneedle-enhanced delivery, as described in Meidan and Michniak (2004) *Am. J. Ther.* 11(4), 312-316, can also be used for transdermal delivery of the muteins described herein. Non-parenteral delivery modes are, for instance, oral, e.g. in the form of pills, tablets, capsules, solutions or suspensions, or rectal administration, e.g. in the form of suppositories. The muteins of the invention can be administered systemically or topically in formulations containing a variety of conventional non-toxic pharmaceutically acceptable excipients or carriers, additives, and vehicles.

The dosage of the mutein applied may vary within wide limits to achieve the desired preventive effect or therapeutic response. It will, for instance, depend on the affinity of the compound for a chosen ligand as well as on the half-life of the complex between the mutein and the ligand in vivo. Further, the optimal dosage will depend on the biodistribution of the mutein or its fusion protein or its conjugate, the mode of administration, the severity of the disease/disorder being treated as well as the medical condition of the patient. For example, when used in an ointment for topical applications, a high concentration of the hNGAL mutein can be used. However, if wanted, the mutein may also be given in a sustained release formulation, for example liposomal dispersions or hydrogel-based polymer microspheres, like PolyActive™ or OctoDEX™ (cf. Bos et al., *Business Briefing: Pharmatech* 2003: 1-6).

Accordingly, the muteins of the present invention can be formulated into compositions using pharmaceutically acceptable ingredients as well as established methods of preparation (Gennaro and Gennaro (2000) *Remington: The Science and Practice of Pharmacy,* 20th Ed., Lippincott Williams & Wilkins, Philadelphia, Pa.). To prepare the pharmaceutical compositions, pharmaceutically inert inorganic or organic excipients can be used. To prepare e.g. pills, powders, gelatine capsules or suppositories, for example, lactose, talc, stearic acid and its salts, fats, waxes, solid or liquid polyols, natural and hardened oils can be used. Suitable excipients for the production of solutions, suspensions, emulsions, aerosol mixtures or powders for reconstitution into solutions or aerosol mixtures prior to use include water, alcohols, glycerol, polyols, and suitable mixtures thereof as well as vegetable oils.

The pharmaceutical composition may also contain additives, such as, for example, fillers, binders, wetting agents, glidants, stabilizers, preservatives, emulsifiers, and furthermore solvents or solubilizers or agents for achieving a depot effect. The latter is that fusion proteins may be incorporated into slow or sustained release or targeted delivery systems, such as liposomes and microcapsules.

The formulations can be sterilized by numerous means, including filtration through a bacteria-retaining filter, or by incorporating sterilizing agents in the form of sterile solid compositions which can be dissolved or dispersed in sterile water or other sterile medium just prior to use.

A mutein of the present invention or a fusion protein or a conjugate thereof can be employed in many applications. In general, such a mutein can be used in all applications antibodies are used, except those with specifically rely on the glycosylation of the Fc part.

Therefore, in another aspect of the invention, the invented muteins of hNGAL are used for the binding and/or detection of a given non-natural ligand of hNGAL. Such use may comprise the steps of contacting the mutein with a sample suspected of containing the given ligand under suitable conditions, thereby allowing formation of a complex between the mutein and the given ligand, and detecting the complexed mutein by a suitable signal.

The detectable signal can be caused by a label, as explained above, or by a change of physical properties due to the binding, i.e. the complex formation, itself. One example is plasmon surface resonance, the value of which is changed during binding of binding partners from which one is immobilized on a surface such as a gold foil.

The muteins of hNGAL disclosed herein may also be used for the separation of a given non-natural ligand of hNGAL. Such use may comprise the steps of contacting the mutein with a sample supposed to contain said ligand under suitable conditions, thereby allowing formation of a complex between the mutein and the given ligand, and separating the mutein/ligand complex from the sample.

In both the use of the mutein for the detection of a given non-natural ligand as well as the separation of a given ligand, the mutein and/or the target may be immobilized on a suitable solid phase.

The hNGAL muteins of the invention may also be used to target a compound to a pre-selected site. In one such embodiment, a mutein of hNGAL is used for the targeting of a pharmaceutically active compound to a pre-selected site in an organism or tissue, comprising of:
 a) conjugating the mutein with said compound, and
 b) delivering the mutein/compound complex to the pre-selected site.

For such a purpose the mutein is contacted with the compound of interest in order to allow complex formation. Then the complex comprising the mutein and the compound of interest are delivered to the pre-selected site. This may, for example, be achieved by coupling the mutein to a targeting moiety, such as an antibody, antibody fragment or lipocalin mutein or lipocalin mutein fragment with binding affinity for the selected target.

This use is in particular suitable, but not restricted to, for delivering a drug (selectively) to a pre-selected site in an organism, such as an infected body part, tissue or organ which is supposed to be treated with the drug. Besides formation of a complex between mutein and compound of interest, the mutein can also be reacted with the given compound to yield a conjugate of mutein and compound. Similar to the above complex, such a conjugate may be suitable to deliver the compound to the pre-selected target site. Such a conjugate of mutein and compound may also include a linker that covalently links mutein and compound to each other. Optionally, such a linker is stable in the bloodstream but is cleavable in a cellular environment.

The muteins disclosed herein and its derivatives can thus be used in many fields similar to antibodies or fragments thereof. In addition to their use for binding to a support, allowing the target of a given mutein or a conjugate or a fusion protein of this target to be immobilized or separated, the muteins can be used for labeling with an enzyme, an antibody, a radioactive substance or any other group having biochemical activity or defined binding characteristics. By doing so, their respective targets or conjugates or fusion proteins thereof can be detected or brought in contact with them. For example, muteins of the invention can serve to detect chemical structures by means of established analytical methods (e.g. ELISA or Western Blot) or by microscopy or immunosensorics. Here, the detection signal can either be generated directly by use of a suitable mutein conjugate or fusion protein or indirectly by immunochemical detection of the bound mutein via an antibody.

Numerous possible applications for the inventive muteins also exist in medicine. In addition to their use in diagnostics and drug delivery, a mutant polypeptide of the invention, which binds, for example, tissue- or tumor-specific cellular surface molecules can be generated. Such a mutein may, for example, be employed in conjugated form or as a fusion protein for "tumor imaging" or directly for cancer therapy.

Thus, the present invention also involves the use of the hNGAL muteins of the invention for complex formation with a given non-natural ligand or target.

In a further aspect, the present invention also encompasses the use of a mutein according to the invention for the manufacture of a pharmaceutical composition. The pharmaceutical composition thus obtained may be suited for use in radioimmune therapy (RIT) or for in vivo imaging. The pharmaceutical composition may be used as monotherapy or as combination therapy.

In still another aspect, the present invention features a diagnostic or analytical kit comprising a mutein according to the present invention.

Another aspect of the present invention relates to a method of treating a subject with radioimmunotherapy (RIT), including administering a mutein of the invention or a pharmaceutical composition comprising a mutein of the invention to a subject in need thereof. The subject may be afflicted by a disease or disorder amenable to such treatment, and may be, for example, cancer or another cell-proliferative disorder.

The subject in need of such a treatment may be a mammal, such as a human, a dog, a mouse, a rat, a pig, an ape such as cymologous monkeys to name only a few illustrative examples.

In still another aspect, the present invention features a method for in vivo imaging in a subject, including administering to said subject a mutein of the invention or a pharmaceutical composition comprising a mutein of the invention. The subject may be defined as above.

The invention is further illustrated by the following non-limiting Examples and the attached drawings in which:

BRIEF DESCRIPTION OF THE DRAWINGS

FIG. 2 shows the properties of hNGAL variants with Me•DTPA binding activity.

FIG. 4 (A) shows a bispecific fusion protein or conjugate comprising (i) an NGAL mutein with Me•DPTA binding activity according to this invention (black) and (ii) an antibody/fragment or an alternative binding protein (e.g. another lipocalin mutein) with specificity for a tumor target is applied to the blood stream. FIG. 4(B) shows the fusion protein accumulating at the tumor while unbound fusion protein is eliminated via the kidney. FIG. 4(C): A radionuclide-DPTA complex is applied to the bloodstream. FIG. 4(D): The radionuclide-DTPA complex is bound by the tumor-associated fusion protein while excess complex is rapidly excreted via the kidney. FIG. 4(E): Local decay of the bound radionuclide leads to efficient cell death in the tumor, also taking advantage of a bystander effect. FIG. 4(D*): Application of a bivalent version of the Me•DPTA complex leads to tighter binding at the tumor site via an avidity effect, thus allowing a prolonged retardation of the radionuclide.

EXAMPLES

Example 1

Figure 1A:
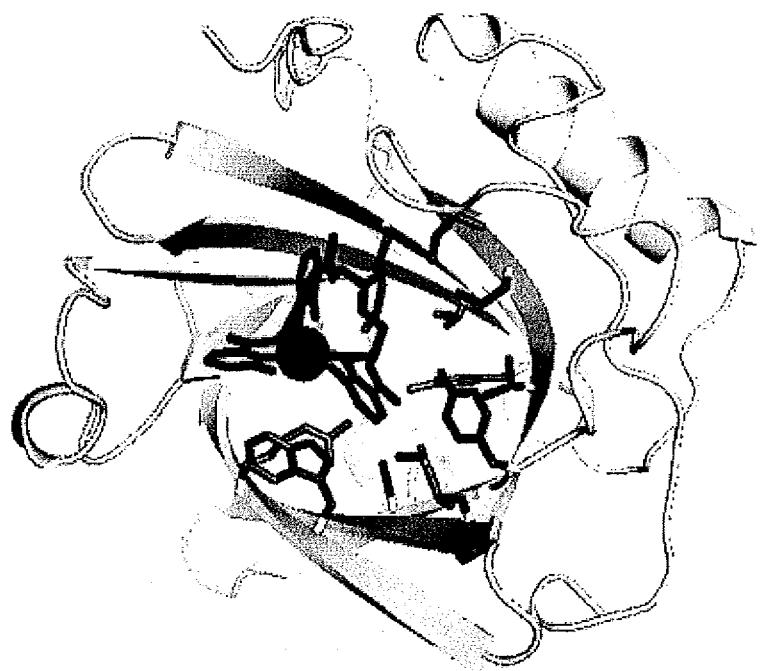
FIG. 1A shows the three-dimensional structure of human hNGAL in complex with enterobactin (PDB entry 1 L6M, chain A, containing the intact ligand; courtesy of Dr. Roland Strong). The polypeptide backbone is shown as shown as ribbon in light grey whereas the natural ligand is colored black. Side chains randomized in the initial "naive" library are shown in grey.

Preparation of Me•DTPA Complex Conjugates 365 nmol (5 mg) bovine pancreatic ribonuclease A (RNase A; Fluka Chemie, Buchs, Switzerland), which exhibits up to ten Lys side chains as well as its free amino-terminus for covalent coupling, dissolved in 1 ml 100 mM $NaHCO_3$ (>99.5%; Carl Roth GmbH & Co, Karlsruhe, Germany), pH 8.3, was reacted with a solution of 1.8 μmol (1.28 mg) p-SCN-Bn-CHX-A"-DTPA ([(R)-2-amino-3-(4-isothio cyanatophenyl)propyl]-trans-(S,S)-cyclohexane-1,2-diamine-pentaacetic acid•3HCl; Macrocyclics, Dallas, Tex.) in 10 μl DMSO over night at 4° C. under agitation. Typically, under these conditions one activated DTPA group reacted per protein molecule as quantified either by ESI-MS (QtoF Ultima Global; Waters GmbH, Eschborn, Germany). Similarly, 150 nmol (10 mg) bovine serum albumin (BSA; Sigma-Aldrich, Munich, Germany) was coupled with 750 nmol (528 μg) p-SCN-Bn-CHX-A"-DTP A. For removal of excess reagent and buffer exchange a gel filtration on a PD-10 column (Amersham Pharmacia Biotech, Freiburg, Germany) was performed with 0.1 M ammonium acetate (>99.9%, Sigma-Aldrich)/acetic acid, pH 5 (Wu et al., Bioorg Med Chem 5, 1925-1934 (1997). Then, an equimolar solution (with respect to the carrier protein) of $TbCl_3$— or $YCl_3$, $LuCl_3$, $GdCl_3$, $InCl_3$ (all from Sigma-Aldrich)—in the same ammonium acetate buffer was added and, after incubation for 10 min at room temperature, the resulting conjugate was stored at −80° C. Using this procedure a Me•DTPA-RNase conjugate with average 1:1:1 stoichiometry was obtained, as was confirmed by fluorescence titration of a sample of the gel-filtrated DTPA-RNase with the gravimetrically prepared $TbCl_3$ solution (λ=295 nm, $\lambda_{Em}$=545 nm; FluoroMax-3; Jovin Yvon, Longjumeau, France), revealing a well detectable increase of Tb luminescence until saturation was achieved.

A double conjugate of RNase (or BSA) with DTPA and digoxigenin (DIG) was prepared by first reacting 915 nmol p-SCN-Bn-CHX-A"-DTPA in 10 μl DMSO with 183 nmol of the carrier protein dissolved in 970 μl 100 mM $NaHCO_3$, pH 8.3, over night at 4° C. and then adding 366 nmol digoxigenin-3-O-methylcarbonyl-c-aminocaproic acid-N-hydroxysuccinimide ester (DIG-NHS; Roche Diagnostics, Mannheim, Germany) in 20 μl DMSO for one hour at room temperature, followed by gel filtration and complex formation with the metal ion as above.

An Y-DTPA-Tris conjugate was prepared for co-crystallization with hNGAL variants by incubating 528 μg (750 nmol) p-SCN-Bn-CHX-A"-DTPA in 100 μL 100 mM tris(hydroxymethyl)aminomethane (Tris; >99.9%, AppliChem, Darmstadt, Germany)/HCl, pH 8.0, over night at room temperature—to achieve thiourea formation—and adding 227 µg (750 nmol) $Y^{3+}$, resulting in a final ligand concentration of 7.5 mM.

A direct conjugate of Me•DTPA with DIG-NHS was prepared by dissolving 2 µmol p-NH$_2$-Bn-CHX-A"-DTPA ([(R)-2-amino-3-(4-aminophenyl)propyl]-trans-(S,S)-cyclohexane-1,2-diamine-pentaacetic acid•4HCl; Macrocyclics) in 100 µl DMF with the addition of 1.7 µL (12 µmol) diisopropylethylamine (Fluka) and reacting with 2 µmol DIG-NHS over night at room temperature. 10 µl of this solution was diluted with 980 µl of the ammonium acetate buffer and 10 µl of 200 nmol YCl$_3$ or TbCl$_3$ in the same buffer was added.

Example 2

Construction of a Mutant hNGAL Phage Display Library

A combinatorial library of hNGAL variants was generated on the basis of the cloned cDNA (Breustedt et al. (2006) *Biochim. Biophys. Acta* 1764, 161-173), which carried the amino acid substitutions Cys87Ser, to remove the single unpaired thiol side chain (Goetz et al. (2000) *Biochemistry* 39, 1935-1941), as well as Gln28His and Thr145Ala to introduce two unique BstXI restriction sites with noncompatible overhangs, thus permitting unidirectional cloning of the mutagenized central gene cassette. Mutagenesis and polymerase chain reaction (PCR) assembly of this region was performed according to published strategy (Beste et al. (1999) *Proc. Natl. Acad. Sci. USA* 96, 1898-1903; Skerra (2001) *J. Biotechnol.* 74, 257-275) in two steps: First, two DNA fragments were separately amplified using pairs of degenerate oligodeoxynucleotides P1, 5'-CAA TTC CAT GGG AAG TGG TAT YNS GTA GGT YNS GCA GGG AAT GCA NNS CTC AGA GAA GAC AAA GAC CCG CA-3' (SEQ ID NO:11); and P2,5'-GTG ACA TTG TAG CTC TTA TCT TCT TTC AGC TCA TAG ATS NRG GCS NNC ATC TTT TGC GGG TCT TTG TCT TC-3' (SEQ ID NO:12); as well as P3,5'-AAG AGC TAC AAT GTC ACA NNS GTC NNS TTT AGG AAA AAG AAG TGT GAC TAC NNS ATC NNS ACT TTT GTT CCA GGT TCC C-3' (SEQ ID NO:13); and P4,5'-GCC AGC TCC TTG GTT CTC CCS NRG AGS NRG ATS NNG AAG TAC TCC CTG TTT TGA G-3' (SEQ ID NO:14), covering the amino acid positions 33/36/41, 52/54, 68/70/79/81, and 134/136/138, respectively. Second, both resulting PCR products were mixed in the presence of the two flanking primers P5,5'-CCA GGA CAA CCA ATT CCA TGG GAA GTG G-3' (SEQ ID NO:15) and P6,5'-GTT CCG AAG CCA GCT CCT TGG TTC TC-3' (SEQ ID NO:16), followed by a few cycles of PCR for assembly and amplification of the full length central gene cassette. All PCR steps were performed using Taq DNA polymerase (Fermentas MBI, St.Leon-Roth, Germany) as described (Schlehuber et al. (2000) *J. Mol. Biol.* 297, 1105-1120). Oligodeoxynucleotides were purchased in HPLC grade from Thermo Fisher Scientific (Ulm, Germany) and further purified by urea PAGE as necessary. The resulting DNA library was cut with BstXI (Promega, Mannheim, Germany) and cloned on the phagemid vector pNGAL35, which is based on the generic expression vector pASK75 (Skerra (1994) *Gene* 151, 131-135) and codes for a fusion protein composed of the OmpA signal peptide, T7-tag, the modified mature hNGAL, followed by an amber codon, and the C-terminal fragment of the gene III coat protein of the filamentous bacteriophage M13, i.e. similar as previously described for the bilin-binding protein (Beste et al., supra; Skerra, supra). After electroporation of *E. coli* XL1-Blue (Bullock et al. (1987) *Biotechniques* 5, 376-378) with the ligation mixture of 6 µg PCR product and 56 µg digested plasmid DNA, ca. $6.5 \times 10^{10}$ transformants were obtained.

Example 3

Selection of hNGAL Variants with Affinity to Metal Chelate Complex, Y•p-NH$_2$-Bn-CHX-A"-DTPA by Phage Display and Colony Screening For production of recombinant phagemids, a culture of *E. coli* XL1-Blue transformed with the pNGAL35 library was infected with VCS-M13 helper phages (Stratagene, Amsterdam Zuidoost, The Netherlands), whereby biosynthesis of the hNGAL-pIII fusion protein was induced with 25 µg/L anhydrotetracycline (Acres, Geel, Belgium) following published protocols (Beste et al., supra; Schlehuber et al., supra).

For each panning cycle about $10^{12}$ recombinant phagemids in PBS (4 mM KH$_2$PO$_4$, 16 mM Na$_2$HPO$_4$, 115 mM NaCl, pH 7.4) were incubated for 1 h with ImmunoSticks (Nunc, Wiesbaden, Germany) that had been coated with 100 µg/ml of the Tb•DTPA-RNase conjugate and blocked for 2 h with 1.2 ml blocking buffer (PBS containing 0.1% (v/v) Tween 20 [polyoxyethylene sorbitan monolaurate; AppliChem] and 2% (w/v) BSA). After 8 washing steps with PBS/T (PBS containing 0.1% (v/v) Tween 20), bound phagemids were eluted for 15 min with 0.1 M glycine/HCl, pH 2.2, followed by immediate neutralization with 0.5 M Tris base. The phagemids were titered and reamplified prior to the next panning. After 7 cycles, an enrichment of the acid-eluted phagemids by a factor 1000 compared with the phagemid number after the first cycle was observed.

Using the pooled phasmid preparation from the last panning step, the mutagenized gene cassette was subcloned via BstXI on the plasmid pNGAL38, which encodes a fusion of the OmpA signal peptide, the hNGAL coding region with the C-terminal Strep-tag II (Schmidt and Skerra (2007) *Nat. Protoc.* 2, 1528-1535) followed by an amber stop codon as well as a gene for the albumin-binding domain (ABD) from Streptococcal protein G (Schlehuber et al., supra). Then, a filter sandwich colony screening assay was performed, whereby the hNGAL-ABD fusion proteins are released from the live colonies plated on a hydrophilic filter membrane and functionally captured on an underlying second membrane coated with human serum albumin (HSA) (Schlehuber et al., supra). This membrane was probed with 150 nM Tb•DTPA-BSA-DIG—or the corresponding RNase conjugate—in PBS/T for 1 h, followed by development with an anti-DIG Fab/alkaline phosphatase (AP) conjugate (Roche Diagnostics) and chromogenic staining according to the published protocol. Having identified spots with intense colour signals on this membrane, the corresponding colonies were picked from the first filter and propagated for plasmid isolation and/or side by side comparison in a secondary colony screen. During this step DTPA conjugates not charged with a metal ion were used as negative control and, to avoid erroneous signals arising from trace metal ion contamination, the high purity 0.1 M ammonium acetate buffer (>99.9%), pH 7.1, was employed.

For the subsequent improvement of affinity of the selected hNGAL variant Tb7 (SEQ ID NO:2), the corresponding BstXI cassette was subjected to error-prone PCR as described further below, followed by phagemid display. In this case, $10^{11}$ recombinant phagemids were incubated for 1 h with ImmunoSticks that had been coated with 25 µg/ml of Tb•DTPA-RNase conjugate for the first cycle and with 10 µg/ml of Tb•DTPA-RNase conjugate for the second to fourth cycles.

For affinity maturation of the hNGAL variant Yd5 (SEQ ID NO:9), the corresponding BstXI cassette was subjected to error-prone PCR (see below), followed by phagemid display, however, under conditions of limiting off-rate. To this end, $10^{12}$ phagemids were incubated for 1 h at room temperature with ImmunoSticks that had been coated with 10 μg/ml of Y•DTPA-RNase conjugate. After 8 washing steps, the sticks were incubated with 800 μL, of a 500 μM solution of the free metal chelate complex, Y•p-$NH_2$-Bn-CHX-A"-DTPA, in PBS for 30 min at room temperature to achieve competition. After another 3 washing steps with PBS, remaining bound phagemids were eluted under acid conditions as above. In this case, three selection cycles were carried out in total.

For some of the affinity maturation steps, the mutagenized hNGAL libraries were directly applied to the colony screen, yet under increasingly stringent conditions, by lowering the concentration of the Tb/Y•DTPA-RNase-DIG conjugate from 50 nM to 5 nM. To raise the stringency even further, the strictly monovalent Tb/Y•DTPA-DIG small molecule conjugate at concentrations of 20 nM to 1 nM was applied. Finally, a competitive colony screen was performed by incubating the second membrane first for 1 h with 10 nM Y•DTPA-DIG and then, after washing three times with PBS/T, with 10 μM of the free complex Y•p-$NH_2$-Bn-CHX-A"-DTPA, followed by washing, detection, and staining as above.

Example 4 hNGAL Mutagenesis by Error-Prone PCR

The construction of a second generation mutant library was carried out by PCR of the gene encoding Tb7 cloned on pNGAL15 with dNTP analogues (Zaccolo et al. (1996) *J. Mol. Biol.* 255, 589-603). The 20 μl reaction mixture contained 10 ng template DNA, 25 μM of each the dNTP analogues 8-oxo-dGTP(8-oxo-2'-deoxyguanosine-5'-triphosphate) and dPTP(6-(2-deoxy-β-D-ribofuranosyl)-3,4-dihydro-8H-pyrimido-[4,5-c][1,2]-oxazine-7-one-5'-triphosphate) (both from TriLink, San Diego, Calif.), 500 μM conventional dNTPs, 0.5 μM flanking primers P5 and P6, 2 mM $MgCl_2$, and 2.5 units of Taq DNA polymerase. 10 cycles were carried out with temperatures of 92° C. for 1 min, 55° C. for 1.5 min, and 72° C. for 5 min. Then reamplification was perfomed with 5 μl sample from above in 100 μl volume under the same conditions but without the analogues using 20 cycles.

Randomization of the variant Yd5 was similarly performed by error-prone PCR using primers P5 and P6 in the presence of 50 μM dPTP, 50 μM 8-oxo-dGTP, one unit of 9° $N_m$ DNA polymerase (New England Biolabs, Frankfurt am Main, Germany) and followed by reamplification as above. The mutant 9° $N_m$ DNA polymerase has 1-5% proofreading exonuclease activity in comparison with the wild type enzyme (Southworth et al. (1996) *Proc. Natl. Acad. Sci. USA* 93, 5281-5285) and was applied to enhance the transversion frequency.

The PCR products were purified by agarose gel electrophoresis (Sambrook and Russel, supra), cut with BstXI, and subcloned on pNGAL35 for phage display selection.

Example 5

Targeted Random Mutagenesis of Amino Acid Subsets in the First hNGAL Variant

For randomization of positions 79 and 80, primers P5 (SEQ ID NO:15) and mut79back, 5'-GGA ACC TGG AAC AAA AGT CAT SNN SNN GTA GTC AC A CTT CTT-3' (SEQ ID NO:17), were applied in a PCR with Taq DNA polymerase as above using pNGAL15-Tb7 as template. A second PCR fragment was generated using primers mut79for, 5'-GAC TTT TGT TCC AGG TTC C-3' (SEQ ID NO:18), and P6 (SEQ ID NO:16). Both fragments were assembled using the flanking primers P5 (SEQ ID NO:15) and P6 (SEQ ID NO:16) as described further above. To randomize positions 125 and 127, primers P5 (SEQ ID NO:15) and mut127back, 5'-GCC AGC TCC TTG GTT CTC CCG AGG AGG GTG ATG GAG AAG TAC TCC CTG TTT TGS NNA ACS NNC TTG AAG AAC ACC-3' (SEQ ID NO:19), were applied in a PCR using pNGAL15-Tb7.N9 as template. The PCR product was extended to full length via reamplification with primers P5 (SEQ ID NO:15) and P6 (SEQ ID NO:16). To randomize positions 77 and 136, primers P5 (SEQ ID NO:15) and mut77back, 5'-GGA ACC TGG AAC AAA AGT CAT GGT CAG GTA SNN ACA CTT CTT TTT CCT AAA CCT G-3' (SEQ ID NO:20), were applied in a PCR using pNGAL15-Tb7.N9.N34 as template. A second PCR fragment was generated using primers mut79for (SEQ ID NO:18) and mut136back, 5'-GCC AGC TCC TTG GTT CTC CCG AGG AGS NNG ATG GAG AAG TAC TCC CT-3' (SEQ ID NO:21). Again, the two fragments were assembled using the primers P5 and P6 (SEQ ID NO:15 and 16).

To simultaneously randomize positions 33, 54, and 136, primers mut33for, 5'-CAA TTC CAT GGG AAG TGG TAT NNS GTA GGT CGG GCA GGG-3' (SEQ ID NO:22), and mut54back, 5'-CTT CTT TCA GCT CAT AGA TSN NGG CGG TCA TCT TTT GCG G-3' (SEQ ID NO:23), were applied in a PCR using pNGAL15-Tb7.N9.N34 as template. A second PCR fragment was amplified using primers mut136for, 5'-ATC TAT GAG CTG AAA GAA G-3' (SEQ ID NO:24), and mut136back (SEQ ID NO:21). Again, both PCR fragments were assembled with the flanking primers P5 (SEQ ID NO:15) and P6 (SEQ ID NO:16). In each case, the mutagenized DNA fragment was subcloned on pNGAL38 for subsequent colony screen.

Example 6

Soluble Protein Production and Purification

The recombinant hNGAL and its variants were produced by periplasmic secretion in *E. coli* BL21 (Studier and Moffat (1986) *J. Mol. Biol.* 189, 113-130) or the supE strain TG1-F⁻ (a derivative of *E. coli* K12 TG1 (Gibson (1984) Studies on the Epstein-Barr virus genome, Cambridge University, England) that was cured from its episome using acridinium orange with the plasmids pNGAL14 (Breustedt et al., supra) and pNGAL15 for the wild type hNGAL and its variants, respectively, both encoding a fusion of the OmpA signal peptide with the mature hNGAL protein and the C-terminal Strep-tag II, whereby the latter carries the two non-compatible BstXI restriction sites for unidirectional subcloning of the mutated gene cassette. The soluble protein was affinity-purified by means of the Strep-tag II (Schmidt and Skerra, supra), followed by size exclusion chromatograpy (SEC) on a Superdex 75 HR 10/30 column (Amersham) using PBS buffer. Protein purity was checked by SDS-PAGE (Fling and Gregerson (1986) *Anal. Biochem.* 155 83-88) and protein concentrations were determined by absorption measurement at 280 nm using calculatory extinction coefficients of 29,930 $M^{-1}$ $cm^{-1}$ for wtNGAL (SEQ ID NO:1) and of 21,680 $M^{-1}$ $cm^{-1}$ for its variants Tb7 (SEQ ID NO:2), Tb7.14 (SEQ ID NO:4), Tb7.N9 (SEQ ID NO:6), Yd5 (SEQ ID NO:9) and C26 (SEQ ID NO:10) (Gill and von Hippel (1989) *Anal Biochem.* 182, 319-326).

Example 7

Measurement of Binding Activity for the Me•DTPA Group in an ELISA

For selective capturing of the hNGAL variants carrying the C-terminal Strep-tag II (Schmidt and Skerra, supra), a 96-well MaxiSorp polystyrene microliter plate (Nunc) was coated with 50 µl of 5 to 10 µg/mL StrepMAB-Immo (IBA, Gottingen, Germany) in PBS over night at 4° C. and blocked with 1% (w/v) BSA in PBS/T at room temperature for 1 h. After 3 washing steps with PBS/T, 50 µL of a 250 nM solution of the purified hNGAL variant was applied for 1 h to all wells. After washing, 50 µL of a dilution series of the Me•DTPA-RNase-DIG conjugate was added and incubated for 1 h. The wells were washed again and bound conjugate was detected with 50 µL of anti-DIG Fab/AP conjugate diluted 1:1000 in PBST for 1 h, followed by signal development in the presence of 100 µl 0.5 mg/ml p-nitrophenyl phosphate in 100 mM Tris/HCl, pH 8.8, 100 mM NaCl, 5 mM $MgCl_2$. The time course of absorption $\Delta A/\Delta t$ 405 nm was measured in a SpectraMax 250 reader (Molecular Devices, Sunnyvale, Calif.) and the data were fitted with KaleidaGraph software (Synergy software, Reading, Pa.) to the equation $$\Delta A = \Delta A_{max} \times [L]_{tot}/(K_D + [L]_{tot})$$

whereby $[L]_{tot}$ represents the concentration of the applied ligand conjugate and $K_D$ is the dissociation constant (Voss and Skerra (1997) *Protein Eng.* 10, 975-982). Alternatively, a competitive ELISA was performed in a similar manner, whereby the Me•DTPA-RNase-DIG conjugate was applied at a fixed concentration of 2.5 to 5 nM in the presence of varying concentrations of the free Me•p-$NH_2$-Bn-HX-A"-DTPA chelate complex in a range between 0.016 and 100 nM. In this case the data were fitted to the sigmoidal equation $$\Delta A = (\Delta A_{max} - \Delta A_{min})/(1+([L]_{tot}^{free}/K_D)^p) + \Delta A min$$

with curve slope p (Hill coefficient) as a further parameter.

Alternatively, to further lower the concentrations of the stationary assay components, a fluorimetric AP substrate was used. In this case, a black Maxisorp 96-well microplate (Nunc) was coated with 50 µl of 5 µg/ml StrepMAB-Immo, followed by a 100 nM solution of the purified hNGAL variant and a fixed concentration of 2.5 nM Y•DTPA-RNase-DIG was applied. Signals were developed by adding 50 µl of 1 mM AttoPhos (Roche) in a buffer supplied by the manufacturer. Kinetic fluorescence measurements were made on a Fluoro-Max-3 microplate reader ($\lambda_{Ex}$=430 nm, $\lambda_{Em}$=535 nm) and evaluated as above.

Example 8

Measurement of Binding Activity for the Me•DTPA Group Via Surface Plasmon Resonance (SPR)

Real time analysis of hNGAL variants was performed on a BIAcore X system (BIAcore, Uppsala, Sweden) using PBS/t (PBS containing 0.005% (v/v) Tween 20) as running buffer. 5 to 27 µg/ml solutions of the Me•DTPA-RNase conjugate in 10 mM Na-acetate, pH 5.0 were immobilized on a CM5 chip using standard amine coupling chemistry, resulting in a ligand density of 240 to 1800 resonance units (RU). The purified hNGAL variant was applied at a flow rate of 5 or 25 µl/min at concentrations of 0.5 up to 500 nM. The sensorgrams were corrected by subtraction of the corresponding signals measured for the control channel, which had been activated and blocked with ethanolamine. Kinetic data evaluation was performed by global fitting with BIAevaluation software V 3.0 (Karlsson et al. (1991) *J. Immunol. Methods* 145, 229-240). Alternatively, the plateau values at the end of the association phase (after 200 s) were plotted against the applied protein concentration and fitted as in the ELISA (see above) to determine the equilibrium dissociation constants (KO.

Example 9

Crystallization of hNGAL Variants

After dialysis against 100 mM NaCl, 10 mM Tris/HCl, pH 8.0 the hNGAL variants Tb7.14 (SEQ ID NO:4) and Tb7.N9 (SEQ ID NO:6) were concentrated to 18 and 25 mg/ml, respectively, using 10 kDa cut-off Ultrafree concentrators (Millipore, Billerica, Mass.) and sterile filtered with a 0.45 mm Costar Spin-X centrifuge unit (Corning, Corning, N.Y.). Both proteins were crystallized using the hanging drop vapour-diffusion technique (Mc Pherson, Crystallization of biological macromolecules, Cold Spring Harbor, N.Y. Cold Spring Harbor Larboratory Press). For crystallization of Tb7.14, 1 µA solution of the apo-protein was mixed with 1 µl reservoir solution, comprising 2 M $(NH_4)_2SO_4$, 200 mM $Li_2SO_4$, 100 mM Tris/HCl, pH 7.0. Crystals of space group $P4_12_12$ with three molecules per asymmetric unit were obtained after 6 weeks at 20° C. Tb7.N9 (SEQ ID NO:6) was crystallized at a final protein concentration of 22 mg/mL (1.1 mM) after adding a slight excess of Y•DTPA-Tris (1.6 mM). In this case 1 µl protein/ligand solution was diluted with 1 µl water and mixed with 1 µl reservoir solution, comprising 22% (w/v) PEG 3350, 100 mM Bis-tris/HCl, pH 5.5. Crystals of space group $P4_12_12$ with two protein chains per asymmetric unit were obtained after one week at 20° C. Crystals of the two hNGAL variants were soaked in the corresponding precipitant solution supplemented with 30 and 20% (v/v) glycerol, respectively, prior to freezing in liquid nitrogen.

Example 10

Data Collection and Model Building

Crystal diffraction data for the Tb7.14 (SEQ ID NO:4) apo-protein and the Tb7.N9 (SEQ ID NO:6)-ligand complex were collected at BESSY (Berlin, Germany) beamlines 14.1 and 14.2, respectively (Table 1).

TABLE 1

| Data collection and refinement statistics | | |
|---|---|---|
| Dataset | Tb7.14 | Tb7.N9/Y•DTPA-Tris |
| Space group | $P4_12_12$ | $P4_12_12$ |
| Unit cell dimensions a, b, c [Å], $\alpha = \beta = \gamma = 90°$ | 113.59, 113.59, 119.79 | 82.35, 82.35, 115.13 |
| molecules/asymmetric unit | 3 | 2 |
| Wavelength [Å] | 0.95373 | 0.95373 |
| Resolution range [Å]$^a$ | 40.00-2.50 (2.64-2.50) | 40.00-2.00 (2.11-2.00) |
| I/σI | 2.8 (2.0) | 4.1 (2.0) |
| $R_{merge}$ [%]$^a$ | 15.4 (33.1) | 10.9 (37.2) |
| Unique reflections | 27785 | 26827 |
| Multiplicity | 8.7 (8.9) | 9.7 (9.8) |

TABLE 1-continued

Data collection and refinement statistics

| | | |
|---|---|---|
| Completeness[a] | 100.0 (100.0) | 98.2 (97.4) |
| Refinement: | | |
| $R_{cryst}/R_{free}$ | 25.56/30.46 | 21.31/23.38 |
| Protein atoms | 4081 | 2772 |
| Ligand atoms | — | 98 |
| Ion atoms | — | 2 |
| Solvent atoms | 480 | 327 |
| Average B-factor [Å²] | 36.50 | 27.62 |
| Geometry: | | |
| R.m.s.d. bond lengths/angles [Å/deg] | 0.0084/1.44 | 0.0094/1.83 |
| Ramachandran analysis: | | |
| Core, allowed, generously allowed, disallowed [%] | 85.6, 10.9, 1.6, 1.8 | 90.5, 7.8, 0.3, 1.4 |

The data were processed with MOSFLM, scaled with SCALA, and reduced with TRUNCATE (CCP4 (1994) *Acta Crystallogr. D* 50, 760-763). Molecular replacement of the Tb7.14 apo-protein was carried out with the program EPMR (Kissinger et al. (2001) *Acta Crystallogr. D Biol. Crystallogr.* 57, 1474-1479) using the structure of the wild type siderocalin hNGAL with all three molecules of the asymmetric unit (Holmes et al. (2005) *Structure* 13, 29-41) (PDB entry 1X71). Molecular replacement of the liganded Tb7.N9 (SEQ ID NO:6) was subsequently carried out with the program MOLREP (CCP4, supra) using the refined model of Tb7.14 (SEQ ID NO:4).

The atomic models were built with the program 0 (Jones et al. (1991) *Acta Crystallogr. A* 47, 110-119). For Tb7.14 (SEQ ID NO:4), there was electron density—at a resolution of 2.5 Å—for residues Ser3-Leu42, Pro48-Gly178 of molecule 1, Ser3-Ala41, Gln49-Asp177 of molecule 2, and Thr4-Leu42, Pro48-Asp177 of molecule 3. For Tb7.N9 (SEQ ID NO:6), there was electron density—at a resolution of 2.0 Å—for residues Asp6-Ala40, Arg43-Asp177 of molecule 1 and residues Leu7-Ala40, Leu42-Gly178 of molecule 2. The ligand Y•DTPA-Tris was modelled using Insight II (Accelrys, San Diego, Calif.) on the basis of the crystal structure of an In•DTPA complex (CSD entry MOQVOD), and corresponding topology and refinement parameters were generated using PRODRG (Schuttelkopf and van Aalten (2004) *Acta Crystallogr. D Biol. Crystallogr.* 60, 1355-1363). Both crystal structures were refined with CNS (Brünger et al. (1998) *Acta Crystallogr. D Biol. Crystallogr.* 54, 905-921) and water molecules were added. Rotamers of asparagine and glutamine residues were checked with NQ-Flipper (Weichenberger and Sippi (2006) *Bioinformatics* 22, 1397-1398). The refined structural models were validated with PROCKECK (Laskowski et al. (1993) *J. Appl. Cryst.* 26, 283-291) and WHAT_CHECK (Hooft et al. (1996) *Nature* 381, 272). Secondary structure elements were assigned using DSSP (Kabsch and Sander (1983) *Biopolymers* 22, 2577-2637) and protein-ligand contact surfaces were calculated with PISA (Krissinel and Henrick (2007) *J. Mol. Biol.* 372, 774-797). Molecular graphics and structural superpositions were made with PyMOL (DeLano (2002) The PyMOL Molecular Graphics System, DeLano Scientific, San Carlos, Calif., USA) while the protein-ligand interactions diagram was prepared with LIGPLOT (Wallace et al. (1995) *Protein Eng.* 8, 127-134).

Example 11

Figure 1B:
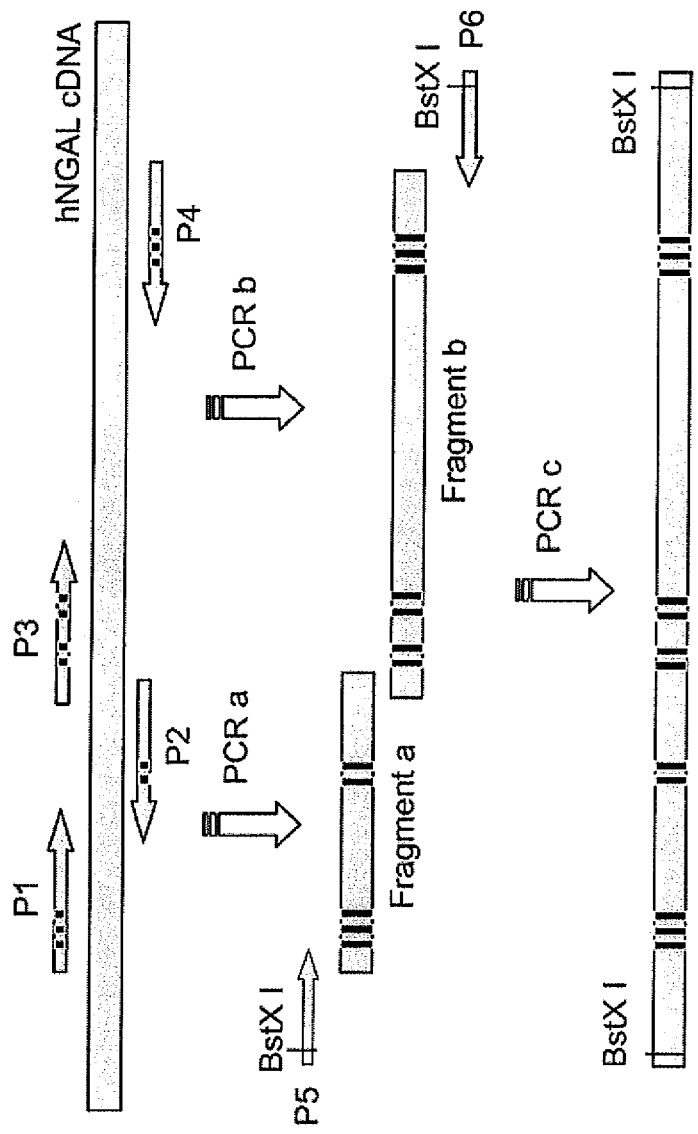
FIG. 1B shows a schematic representation of the assembly PCR strategy for the simultaneous random mutagenesis of the 12 amino acid positions 33, 36, 41, 52, 54, 68, 70, 79, 81, 134, 136, and 138. The structural gene of NGAL was used as template in a PCR with the degenerate oligodeoxynucleotides P1 and P2, resulting in fragment (a), and with the degenerate primers P3 and P4, resulting in fragment (b). Randomized positions are indicated by light bars. Both fragments were isolated, combined and applied in a next amplification carried out with PCR primers P5 and P6. Two different BstXI restriction sites were used for subcloning of the gene cassette on pNGAL35, a plasmid vector for phage display.

Selection of Lipocalin Variants with Me•DTPA Specificity from a Lipocalin Random Library Based on the known crystal structure of hNGAL in complex with its natural ligand enterobactin (Goetz et al., supra) and its cloned cDNA (Breustedt et al., supra), we constructed a combinatorial library by specifically randomizing the codons for 12 amino acid positions in the binding pocket (FIG. 1, Table 2).

Residues at the bottom of the ligand pocket and in close proximity to the natural iron siderophore complex, including two of the three positively charged side chains R81, K125, and K134 (Goetz et al., supra), were preferentially chosen for the targeted mutagenesis. These positions were expected to tolerate both small and large side chain substitutions, reaching as deeply as possible into the cavity without affecting the hydrophobic residue packing in the lower part of the β-barrel.

TABLE 2

Amino acid sequences of selected hNGAL variants.

| Residue No.[a] | hNGAL (SEQ ID NO: 1) | Tb7 (SEQ ID NO: 2) | Tb7.14 (SEQ ID NO: 4) | Tb7.N9 (SEQ ID NO: 6) | Tb7.N9.N34 (SEQ ID NO: 7) | Ya6 (SEQ ID NO: 8) | Yd5 (SEQ ID NO: 9) | C26 (SEQ ID NO: 10) |
|---|---|---|---|---|---|---|---|---|
| [a]28 | Gln | His | His | His | His | His | His | His |
| [a]87 | Cys | Ser | Ser | Ser | Ser | Ser | Ser | Ser |
| [a]145 | Thr | Ala | Ala | Ala | Ala | Ala | Ala | Ala |
| 33 | Val | Gln | Gln | Gln | Gln | Gln | Gln | Gln |
| 36 | Leu | Arg | Arg | Arg | Arg | Arg | Arg | Arg |
| 41 | Ile | Ala | Ala | Ala | Ala | Ala | Ala | Ala |
| 52 | Tyr | Thr | Thr | Thr | Thr | Thr | Thr | Thr |
| 54 | Thr | [b]Gln | Gln | Gln | Gln | Gln | Gln | Gln |
| 68 | Ser | Ala | Ala | Ala | Ala | Ala | Ala | Ala |
| 70 | Leu | Arg | Arg | Arg | Arg | Arg | Arg | Arg |
| 79 | Trp | Ala | Ala | _Leu_ | Leu | Leu | Leu | Leu |
| 81 | Arg | Met | Met | Met | Met | Met | Met | Met |
| 134 | Lys | Ser | Ser | Ser | Ser | Ser | Ser | Ser |
| 136 | Thr | Thr | Thr | Thr | Thr | _Ser_ | _Ser_ | Ser |
| 138 | Tyr | Leu | Leu | Leu | Leu | Leu | Leu | Leu |
| [c]77 | Asp | Asp | Asp | Asp | Asp | Asp | _Glu_ | Glu |
| [c]80 | Ile | Ile | _Thr_ | Thr | Thr | Thr | Thr | Thr |

TABLE 2 -continued

Amino acid sequences of selected hNGAL variants.

| Residue No.[a] | hNGAL (SEQ ID NO: 1) | Tb7 (SEQ ID NO: 2) | Tb7.14 (SEQ ID NO: 4) | Tb7.N9 (SEQ ID NO: 6) | Tb7.N9.N34 (SEQ ID NO: 7) | Ya6 (SEQ ID NO: 8) | Yd5 (SEQ ID NO: 9) | C26 (SEQ ID NO: 10) |
|---|---|---|---|---|---|---|---|---|
| [c]127 | Ser | Ser | Ser | Ser | <u>Gln</u> | Gln | Gln | Gln |
| [d]42 | Leu | Leu | Leu | Leu | Leu | Leu | Leu | <u>Pro</u> |
| [d]48 | Pro | Pro | Pro | Pro | Pro | Pro | Pro | <u>Leu</u> |
| [d]49 | Gln | Gln | Gln | Gln | Gln | Gln | Gln | <u>Leu</u> |
| [d]55 | Ile | Ile | Ile | Ile | Ile | Ile | Ile | <u>Thr</u> |
| [d]75 | Lys | Lys | Lys | Lys | Lys | Lys | Lys | <u>Met</u> |

[a]Sequential numbering of the mature protein sequence (cf SwissProt entry P80188). Positions 28, 87, and 145 were specifically mutated for reasons of genetic manipulation.
[b]The amber stop codon is translated as Gln in the supE background of the bacterial strains that were used for the selection experiments and was later replaced by the codon CAG.
[c]Accidental mutations at positions that were not part of the initial random mutagenesis.
[d]Mutations arising from error-prone PCR with the nucleotide analogues and 9°N$_m$ DNA polymerase.

This strategy could be expected to allow efficient reshaping of the ligand pocket to achieve a novel specificity for the smaller DTPA metal chelate complex, similarly as it was previously demonstrated with an insect lipocalin and organic molecules as ligands (Beste et al., supra; Schlehuber et al., supra).

Concerted random mutagenesis of these positions, which were spread across large part of the hNGAL primary sequence, was realized according to a previously developed PCR assembly strategy (Beste et al., supra; Skerra (2001), supra) with appropriate modifications. To this end, two gene segments, each comprising one pair of the altogether four clusters of randomized residues (#1: 33, 36, 41; #2: 52, 54; #3: 68, 70, 79, 81; #4: 134, 136, 138), were first separately amplified, using oligodeoxynucleotides with degenerate NNS codons at the desired positions. The two resulting PCR products—which included a short overlap in the middle of the NGAL gene—were isolated, mixed, and then assembled in another amplification just with few cycles, using flanking primers that contributed two unique BstXI restriction sites (see above). After unidirectional cloning on a suitable phasmid vector for filamentous phage display (Skerra (2001), supra), a molecular library with a diversity of approximately $6.5 \cdot 10^{10}$ independent transformants was obtained.

This library was employed for the enrichment of Me•DTPA specific hNGAL variants via panning on ImmunoSticks coated with the immobilized ligand. For this purpose, a ligand derivative with a chemically reactive isothiocyanate group, p-SCN-Bn-CHX-A"-DTPA, was covalently coupled to Ribonuclease A, which served as a robust carrier protein devoid of non-specific binding activities (Schlehuber et al., supra), and charged with the transition metal ion $Tb^{3+}$. This lanthanide was chosen as a model ion for the initial selection experiments as it (i) shows a luminescent behaviour strongly dependent on its molecular environment (Martini et al. (1993) Eur. J. Biochem. 211, 467-473; Corneillie et al., supra; Handl and Gillies (2005) Life Sci. 77, 361-371), which was helpful to analyze the proper charging of the protein-DTPA conjugate, and (ii) its radius is not too much different from therapeutically or diagnostically relevant radioactive isotopes such as $^{90}Y^{3+}$, $^{111}In^{3+}$ and $^{177}Lu^{3+}$ (Goldenberg (2002) J. Nucl. Med. 43, 693-713; Boerman et al. (2002) J. Nucl. Med. 44, 400-411; Corneillie et al., supra; Kenanova and Wu, supra).

After seven cycles of phagemid display panning, the enriched pool of hNGAL variant genes was subcloned on another plasmid and subjected to a filter sandwich colony screen (Schlehuber et al., supra). In this experiment the hNGAL variants became secreted from live E. coli colonies as a fusion with a bacterial albumin-binding domain (ABD) and were immediately bound to an underlying filter membrane coated with human serum albumin (HSA). The functionally immobilized hNGAL variants were probed for binding of an RNase double conjugate with Tb•DTPA and digoxigenin groups. After signal development with an anti-DIG Fab/AP conjugate several clones with specific ligand-binding activity were identified. Sequence analysis of 16 selected clones revealed that 7 of these had an identical sequence, which was named Tb7 (SEQ ID NO:2) (Table 2), whereas the remaining clones showed very similar sequences, with up to 4 amino acid exchanges compared with Tb7.

Example 12

Affinity and Specificity of Selected hNGAL Variants for the Me•DTPA Chelate Complex The hNGAL variants were subcloned onto a suitable expression vector and produced as soluble proteins in the periplasm of the E. coli strain BL21, which lacks endogenous enterobactin (Goetz et al., supra). Purification from the periplasmic protein extract by means of the C-terminal Strep-tag II (Schmidt and Skerra, supra) and size exclusion chromatography yielded 0.5-3 mg protein per 1 L shake flask culture, similarly as for the recombinant wild type protein (Breustedt et al., supra). The purity was greater than 95% as determined by Coomassie stained SDS-PAGE (FIG. 2).

Binding activity was first investigated in an EISA for the Tb•DTPA-RNase A conjugate that had also served during the selection procedure (see Materials & Methods). The variant Tb7 showed a strong and metal-dependent signal (FIG. 2B) with an apparent affinity in the low nanomolar range (74.5±7.8 nM) whereas wild-type hNGAL exhibited no measurable binding activity.

Example 13

Affinity Maturation of hNGAL Variant Tb7 for Improved Me•DTPA Binding

Starting with the coding region for the hNGAL variant Tb7, a second generation library was constructed by error-prone PCR of the central gene cassette (flanked by the two BstXI restriction sites at amino acid positions 25-29 and 141-145) in the presence of deoxynucleotide analogues (Zaccolo et al, supra), followed by four cycles of phagemid display and colony screening under more stringent conditions (cf. above). DNA sequencing of 10 clones from the colony screen giving rise to the most intense signals for Tb•DTPA binding showed that nine of them carried the amino acid substitution Ile80Thr, together with one or two additional substitutions at positions 65, 71, 73, 74, 75, 116 or 135. The three variants Tb7.1 (Lys75Asp/Ile80Thr) (SEQ ID NO:3), Tb7.14 (Ile80Thr) (SEQ ID NO:4), and Tb7.17 (Phe71Ser/Lys73Glu/Ile80Thr) (SEQ ID NO:5) were again expressed as soluble proteins in *E. coli* BL21. After purification as above, their ligand-binding properties were investigated in an ELISA (data not shown). These three variants exhibited somewhat higher signal intensities at saturation than Tb7 but their half-maximal concentration values for binding of the Tb-DTPA complex were about 15 nM and, thus, not much improved.

In the second stage, saturation mutagenesis was performed in a consecutive manner for the amino acid sets at positions 79/80, 125/127, and 77/136 as well as 33/54/136. Positions were chosen according to the mutational patterns of promising variants identified so far and by using molecular model building on the basis of the wild type hNGAL structure as well as the crystal structure of its variant Tb7.14 (SEQ ID NO:4; see below). To this end, a PCR assembly strategy similar to the one for the construction of the original library was applied, employing pairs of synthetic oligodeoxynucleotides carrying fully degenerate codon (or anticodon) sequences at the desired positions (cf. above). As the resulting molecular libraries had low combinatorial complexities they were directly subjected to the colony screening assay as before, however using lower ligand concentration during the selection. For mutagenesis of positions 77/136 and 33/54/136, the Y•DTPA-DIG conjugate was applied as target (i.e. switching from $Tb^{3+}$ to the medically more relevant $Y^{3+}$), whereas selection at positions 79/80 and 125/127 was performed with ThDPTA-RNase-DIG conjugate.

After each random mutagenesis the best resuting clone was chosen according to its ligand affinity, yield of soluble periplasmic expression, and stable monomer formation during gel filtration as criteria. During this procedure three promising variants with improved binding activities (up to app. 30-fold) subsequently emerged: Tb7.N9 (A79L/I80T) (SEQ ID NO:6), Tb7.N9.N34 (S127Q) (SEQ ID NO:7), and Yd5 (D77E/T136S) (SEQ ID NO:9) (Table 2). The final variant Yd5 showed the best binding activity, with a $K_D$ value of 3.5 nM (see below and Table 3).

TABLE 3

The dissociation constants and binding kinetics of selected hNGAL variants for $Y^{3+}$•DTPA-RNase/$Tb^{3+}$•DTPA-RNase measured by real-time SPR analysis at a flow rate of 5 µl/min.

| | $Y^{3+}$•DTPA-RNase | | | |
|---|---|---|---|---|
| Lipocalin mutein | $k_{on}$ [$M^{-1}s^{-1}$] | $k_{off}$ [$s^{-1}$] | $K_D$ [nM]$^a$ | $\tau_{1/2}$ [s] |
| Tb7 | $9.98 \times 10^5$ | 0.1 | 100 | 6.9 |
| Tb7.N9 | $1.61 \times 10^6$ | $2.3 \times 10^{-2}$ | 14.3 | 30 |
| Tb7.N9.N34 | $1.57 \times 10^6$ | $2.08 \times 10^{-2}$ | 13.2 | 33 |
| Ya6 | $1.72 \times 10^6$ | $5.53 \times 10^{-3}$ | 3.2 | 125 |
| Yd5 | $9.84 \times 10^5$ | $3.45 \times 10^{-3}$ | 3.5 | 201 |
| C26 | $2.5 \times 10^6$ | $7.04 \times 10^{-4}$ | 0.282 | 984 |

TABLE 3-continued

The dissociation constants and binding kinetics of selected hNGAL variants for $Y^{3+}$•DTPA-RNase/$Tb^{3+}$•DTPA-RNase measured by real-time SPR analysis at a flow rate of 5 µl/min.

| | $Tb^{3+}$•DTPA-RNase | | | |
|---|---|---|---|---|
| Lipocalin mutein | $k_{on}$ ($M^{-1}s^{-1}$) | $k_{off}$ ($s^{-1}$) | $K_D$ [nM]$^a$ | $K_{d/eq}$ [nM]$^b$ | $\tau_{1/2}$ (s) |
| Tb7 | $5.35 \times 10^5$ | $4.01 \times 10^{-2}$ | 74.9 | 50 ± 6.5 | 17 |
| Tb7.N9 | $6.89 \times 10^5$ | $1.05 \times 10^{-2}$ | 15.2 | 25 ± 2.7 | 66 |
| Tb7.N9.N34 | $7.46 \times 10^5$ | $1.14 \times 10^{-2}$ | 15.3 | 21 ± 2.3 | 61 |
| Ya6 | $1.24 \times 10^{-6}$ | $2.96 \times 10^{-3}$ | 2.39 | 5 ± 0.22 | 234 |
| Yd5 | $1 \times 10^6$ | $2.46 \times 10^{-3}$ | 2.34 | 3.8 ± 0.15 | 282 |

$^a$determined from the kinetic analysis
$^b$determined from the concentration-dependent saturation values in an equilibrium analysis
Data analysis was performed by global fit according to the 1:1 binding model In the third stage, another error prone PCR mutagenesis of the whole central coding cassette was performed on the basis of Yd5 (SEQ ID NO:9) and followed by phage display selection towards slow dissociation kinetics by using competitive conditions. To this end, panning was performed with the Y•DTPA-RNase target adsorbed to ImmunoSticks and, after washing, bound phagemids were incubated in the presence of a 500 µM solution of the free metal chelate complex, Y•p-NH$_2$-Bn-CHX-A"-DTPA, as competitor for 30 min, followed by another three washing steps and, finally, acid elution. After three cycles of phagemid selection, the enriched pool of hNGAL variants was subcloned and subjected to the colony screening assay, again applying competitive conditions. 16 variants giving rise to intense staining signals, even in the presence of an approximately thousand-fold molar concentration of the unlabelled ligand, were sequenced. Thus, the variant C26 (SEQ ID NO:10) was isolated, which exhibits five additional mutations (L42P/P48L/Q49L/I55T/K75M), most of them in loop #1.

Example 14

Biochemical Characterization of Selected hNGAL Variants by Competition ELISA and Surface Plasmon Resonance The hNGAL variants resulting from the affinity maturation of Tb7 were produced in *E. coli* as soluble proteins at the shake flask scale and purified via the Strep-tag II and SEC as before. All selected variants exhibited excellent expression characteristics and were purified as stable and fully monomeric proteins (FIG. 2A) from the periplasmic cell extract, showing final yields of 0.5 to 3 mg per liter shake-flask culture.

Figure 2A:
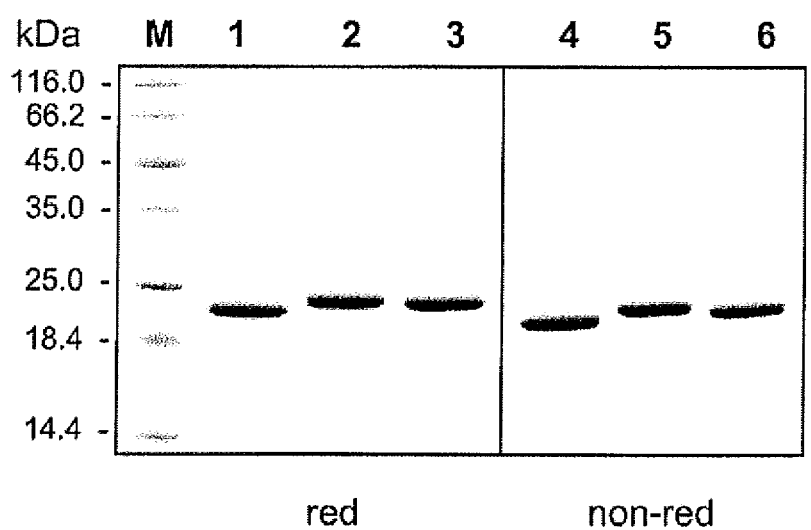
FIG. 2A shows SDS-PAGE analysis of recombinant wild type hNGAL (lanes 1,4) and variants Tb7.N9 (lanes 2,5) as well as C26 (lanes 3,6) after Strep-tag II affinity purification and gel filtration. Lanes 1-3 show samples reduced with 2-mercaptoethanol. The slightly enhanced electrophoretic mobility under non-reducing conditions indicates proper formation of the single disulphide bond in each case.
Figure 2B:
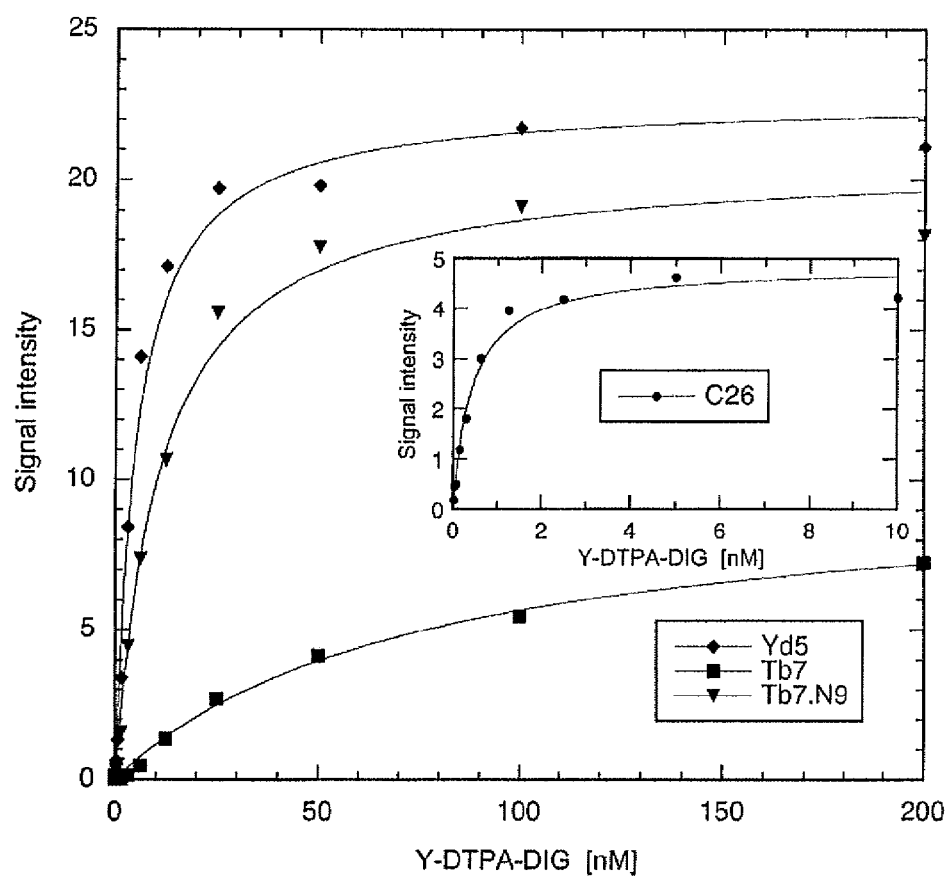
FIG. 2B depicts binding activity in the ELISA. A microtiter plate was coated with the purified hNGAL variants, captured via an antibody specific for the Strep-tag II, and incubated with a dilution series of the Y•DTPA-DIG (small molecule) conjugate, followed by detection with anti-DIG Fab/AP and pNPP substrate (signal intensity is given in mOD/min). Recombinant wild type hNGAL revealed negligible signals in this assay (not shown). Note that the hNGAL variant from the last maturation step, C26 (see inset), was immobilized at a significantly lower density (100 vs. 250 nM with a capture antibody concentration of 2.5 vs. 10 μg/ml).

Binding activities were first compared in an ELISA using the hNGAL variants captured to the microtiter plate and incubating them with varying concentratons of the Y•DTPA-DIG conjugate, which was detected with an anti-DIG Fab/AP conjugate (FIG. 2B). All variants, starting from Tb7 to its most recently improved derivatives, showed hyperbolic saturation curves whereas wild type hNGAL did not reveal any binding activity for the metal chelate complex (not shown). The amplitude of the saturation curves increased while the half-maximal ligand concentration—corresponding to apparent Kg values of 74±8 nM (Tb7), 10.8±1.2 nM (Tb7.N9), 5.0±0.7 nM (Yd5), 0.43±0.06 nM (C26)—decreased over the course of the in vitro affinity maturation.

Figure 2C:
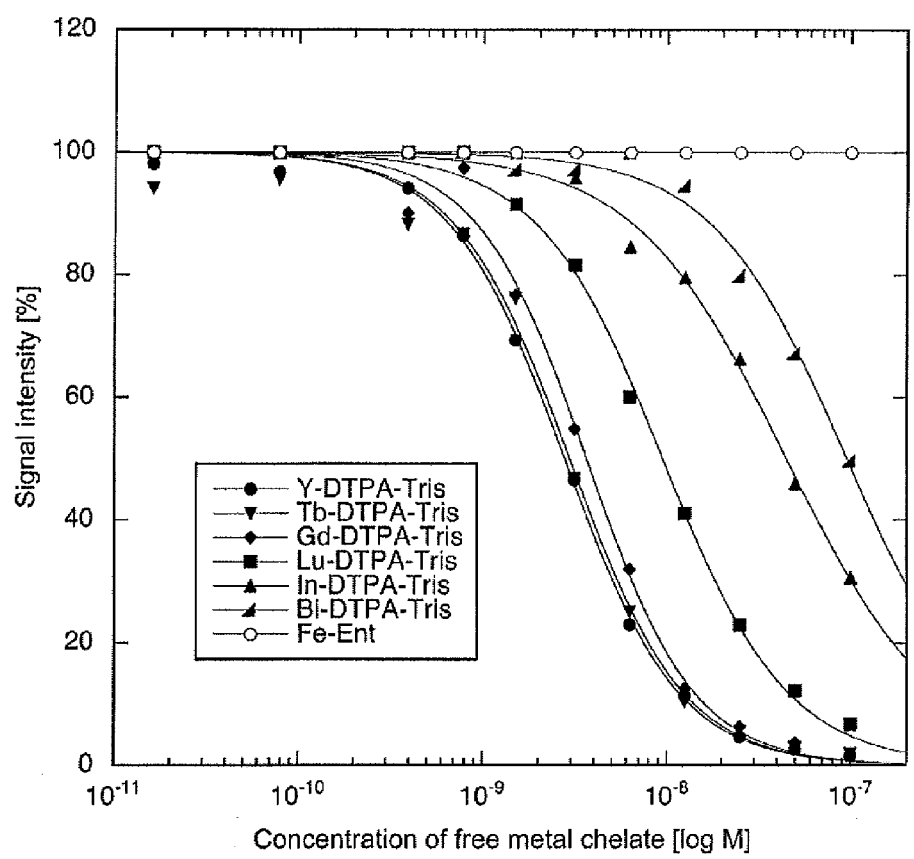
FIG. 2C shows the metal chelate binding activity of hNGAL variant C26 in a competitive ELISA. The setup of this ELISA was similar to the one shown in panel (B), yet using a fixed concentration of the Y•DTPA-RNase-DIG (protein) conjugate as tracer in the presence of a variable concentration of the free Me.Bn-CHX-A"-DTPA-Tris chelate complex or—for comparison—of $Fe^{3+}$•enterobactin.

The binding activity of the hNGAL variants for the small soluble chelate ligand was further investigated in a competition ELISA using microtiter plates coated with Tb•DTPA- RNase and Me•p-NH$_2$-Bn-CHX-A"-DTPA as free ligand competitor, using Tb$^{3+}$ and Y$^{3+}$ as well as other trivalent metal ions. These measurements showed nice inhibition curves for the Tb$^{3+}$/Y$^{3+}$-charged chelate complex especially in case of the variants Tb7.N9, Yd5, and C26 resulting from the affinity maturation. In contrast, the binding activity of Tb7 for the immobilized ligand was probably too weak to yield a proper competition effect. The final variant, C26, was more thoroughly analyzed using different metal ions (FIG. 2C). Its Kg values deduced from the half-maximal free metal chelate concentrations were: 2.7±0.03 nM (Y$^{3+}$), 3.6±0.24 nM (Gd$^{3+}$), 2.9±0.17 nM (Tb$^{3+}$), 9.4±0.33 nM (Lu$^{3+}$), 44.7±2.5 nM (In$^{3+}$), and 95±7 nM (BP). Thus, the engineered hNGAL variants, especially C26, exhibit strong binding activity towards the small metal chelate ligand whereas the context of RNase, which was employed as carrier protein during the selection, does not play a significant role.

Figure 2D:
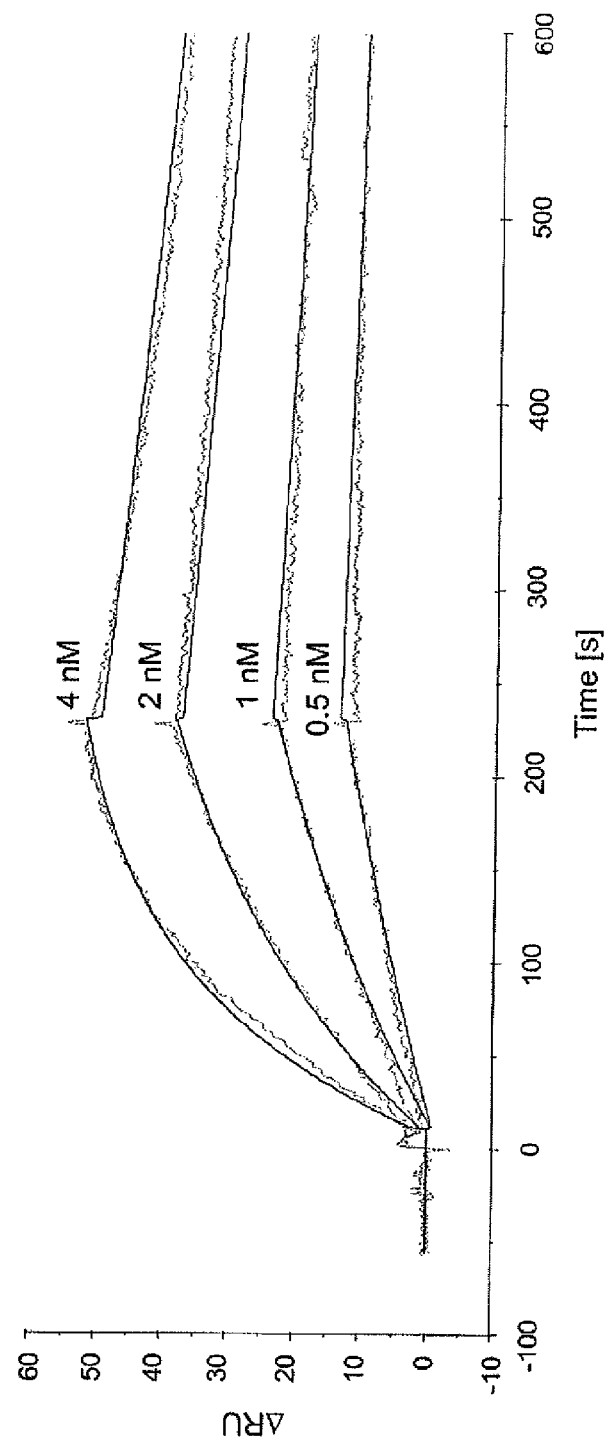
FIG. 2D depicts the kinetic real time analysis of hNGAL variant C26 measured on a Biacore instrument. The Y•DTPA-RNase conjugate was coupled via amine chemistry to a CM5 sensor chip (ΔRU=240) and the purified hNGAL variant C26 was applied at varying concentrations. The measured signal is shown as a grey line whereas the curve fit is depicted as a black line in each case. The kinetic constants determined from this set of curves are listed in Table 3 (Example 13).

Finally, the hNGAL variants were analyzed by SPR using a Biacore CM-5 chip with the covalently attached Y-DTPA-RNaseA conjugate and applying the purified recombinant proteins (Table 3). Again, wild-type hNGAL did not exhibit any significant binding activity whereas moderate binding signals were obtained for Tb7 (not shown). However, its derivatives isolated at different stages of the in vitro affinity maturation showed increasing affinity towards the immobilized target, with higher values around 3 nM for Ya6 and Yd5. This represents an approximately 30-fold improvement over the parental lipocalin mutein Tb7 (K$_D$=75 to 100 nM). The improved K$_D$ values result primarily from slower ligand dissociation. In this respect the two variants with higher affinities differ, whereby Yd5 shows a significantly longer half life of dissociation (ca. 200 s). Notably, the variant, C26 resulting from the competitive selection experiment revealed even a 282 μM affinity to the metal chelate ligand (FIG. 2D).

Example 15

Crystallographic Analysis of hNGAL Variants with Me•DTPA Binding Activity

Figure 3:
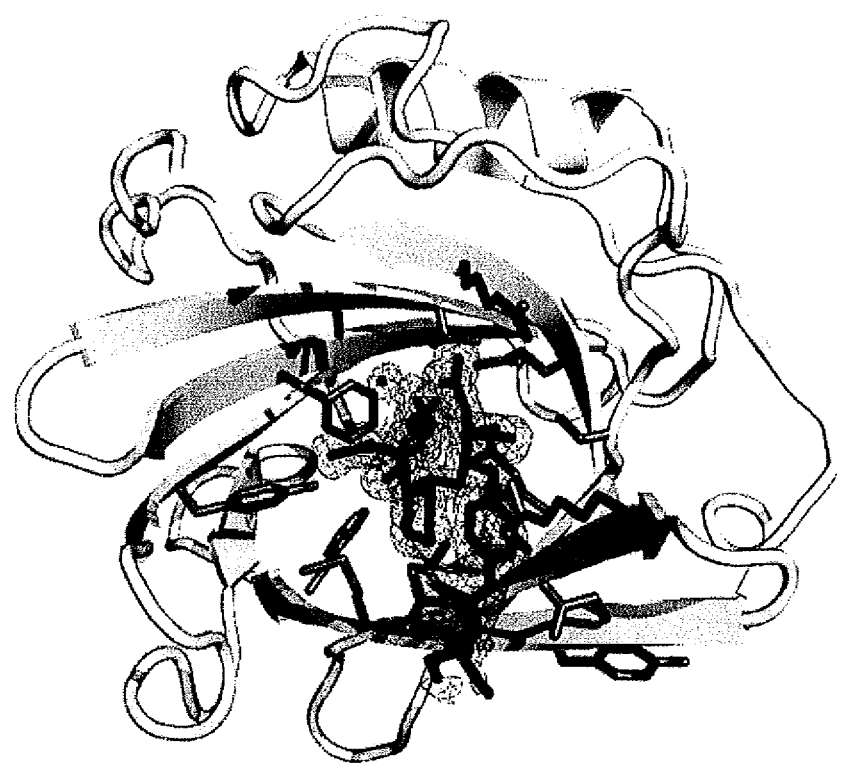
FIG. 3 shows the crystal structure of the hNGAL variant Tb7.N9 in complex with the Y•DTPA-Tris chelate with the polypeptide backbone is shown as ribbon in light grey whereas the bound $Y^{3+}$•DTPA ligand is shown as a black stick model, including its $2F_oF_c$ electron density—contoured at 1σ around the ligand DTPA and one $Y^{3+}$-coordinating water molecule and at 4σ around the $Y^{3+}$ ion. Within a 4 Å radius altogether 15 residues are found in contact distance with the bound metal chelate complex, at least one in each of the eight β-strands: Gln33, Arg36, Thr52, Gln54, Val66, Ala68, Arg70, Asp77, Tyr78 (only via backbone), Leu79, Met81, Phe83, Tyr106, Phe123, and Thr 136. The side chains of these residues are depicted as grey sticks, together with residue Ser134 and a hydrogen-bonded water molecule that forms a bridge to the metal-bound water.
Figure 4:
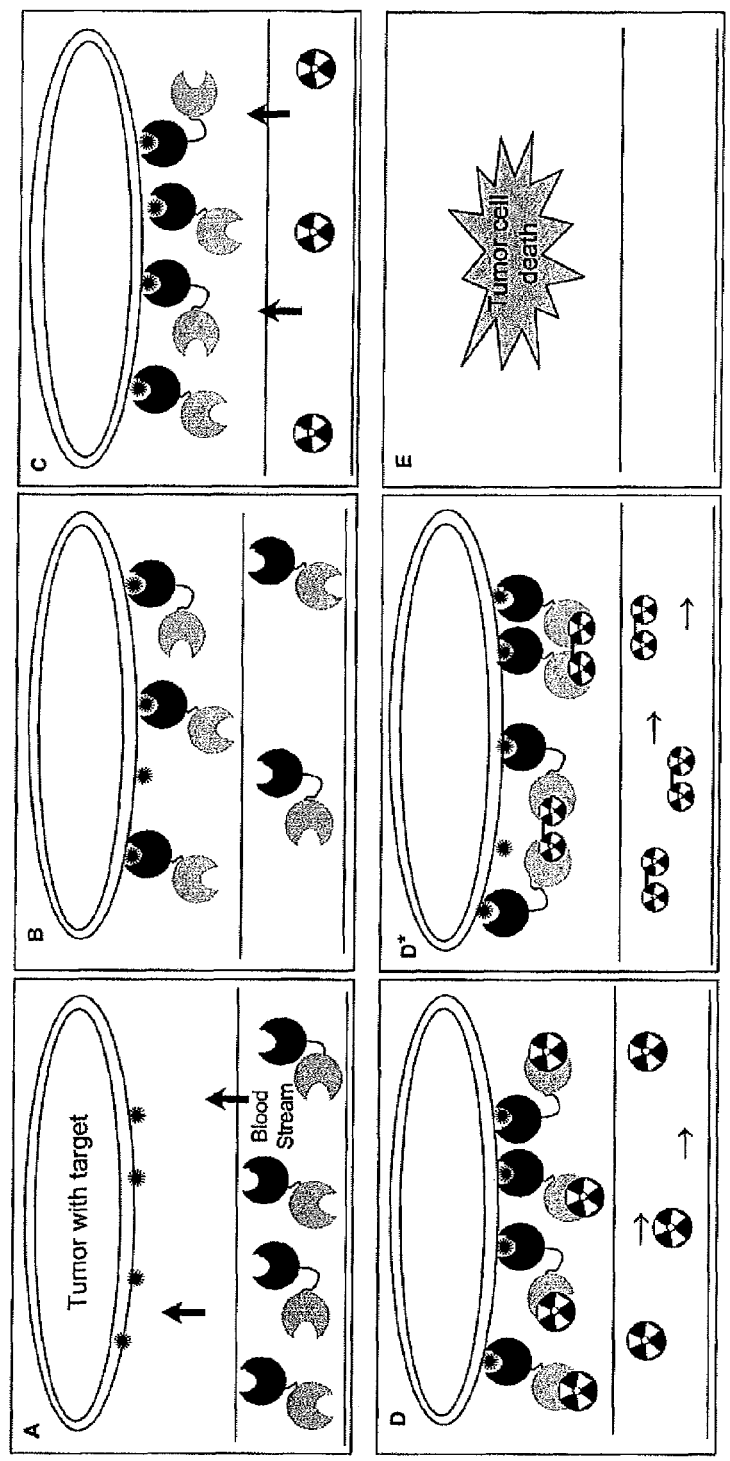
FIG. 4 shows a potential application of hNGAL variants with Me•DTPA binding activity for pretargeting radioimmunotherapy or in vivo imaging.

The hNGAL variants Th7.14 (SEQ ID NO:4) and Th7.N9 (SEQ ID NO:6) were subjected to X-ray crystallographic analysis, the latter in complex with the ligand Y•DTPA-Tris. As expected, both proteins exhibit the typical lipocalin fold comprising an eight-stranded antiparallel β-barrel with an α-helix attached to its side (FIG. 3). Superposition of the 58 mutually equivalent backbone positions of Tb7.14 and of Tb7.N9 (Cα atoms 28-37, 52-58, 63-69, 77-84, 91-94, 106-113, 118-124, 133-139, each from chain A), which are structurally conserved for the β-barrel of the lipocalins (Skerra (2000), supra), resulted in a root mean square deviation (r.m.s.d.) of 0.31 Å. The r.m.s.d. for the chains A of Th7.14 and of hNGAL in complex with trencam-3,2-hopo (PDB entry 1X71), which had been used for molecular replacement, was 0.24 Å (for Cα atoms 7-40 and 49-177) while the mutual r.m.s.d. between chains A/B and A/C in the asymmetric unit of Tb7.14 was 0.43 Å and 0.35 Å, respectively. For chain A of Tb7.14 and chain A of hNGAL in complex with enterobactin (PDB entry 1L6M) the r.m.s.d. was 0.26 Å while the corresponding r.m.s.d. for Tb7.N9 was slightly higher with 0.31 Å. The mutual r.m.s.d. between chains A and B in the asymmetric unit of Tb7.N9 was 0.58 Å. A comparison of the side chain conformations of Th7.14 and Tb7.N9 showed major changes only for residues Gln33, Arg36, Gln49, Gln54, and Thr136. The side chain of Arg36 forms a hydrogen bond between its guanidinium NH1 atom and a carboxylate oxygen (O2) of the bound DTPA (3.3 Å).

In the complex with Tb7.N9 the bound Y•DTPA-Tris nestles at one side of the cleft at the open side of the β-barrel and fills about one third of its volume. The remainder of the cavity is occupied with 9 water molecules, which form a hydrogen bond network. There are no direct contacts between amino acids and the lanthanide ion. The DTPA derivative fills eight of nine coordination sites of Y$^{3+}$ while the ninth site is occupied by a water molecule (HOH9). This water molecule is in hydrogen bond distance with two of the DTPA carboxylate groups (HOH9-LIG O1, 2.9 Å; HOH9-LIG O9, 3.0 Å) and with another crystallographically defined water molecule (HOH143, 2.6 Å distance)—in the second shell around the metal ion—which itself is hydrogen-bonded to Ser134 (HOH 143-Ser134 OG, 2.9 Å).

The entire chelate complex is oriented with its hydrocarbon groups, including the cyclohexane ring and the benzyl side chain, towards a contiguous hydrophobic stretch on β-strands B, C, and D (FIG. 3). The polar carboxylate groups, including the Y$^{3+}$-coordinating water molecule, point towards β-strands G, H, and A, where a gap filled with water molecules is formed, which was previously occupied by the natural siderophore in the case of wild type hNGAL.

The DTPA part of the ligand, which is nicely defined in the electron density revealing the anticipated chirality (Brechbiel and Gansow (1992) *J. Chem. Soc. Perkin Trans* 1, 1173-1178), can be described as a baseball glove with the metal ion representing the grabbed baseball, similar as it was previously seen in the small molecule crystal structure of an In$^{3+}$•DTPA complex (Maecke et al. (1989) *J. Nucl. Med.* 30, 1235-1239). The Y$^{3+}$ ion is coordinated by nine atoms. Eight of them stem from the octadentate chelating ligand, five from its carboxylate oxygens (distances 2.3-2.5 Å) and three from its amine nitrogens (distances 2.5-2.7 Å), whereas one is a bound water oxygen (distance app. 2.7 Å). Similarly as in the natural hNGAL enteroactin complex, there are no direct liganding contacts between the metal ion and protein side chains. The thiourea group protruding from the benzyl side chain of the DTPA derivative and the conjugated Tris moiety are orientated outwards from the lipocalin cleft. There are two hydrogen bonds between atom N4 of the thiourea group and the two carboxylate oxygens of Asp77, (OD1: distance 3.4 Å; OD2: distance 2.9 Å). The terminal tris-hydroxymethyl group is only partially defined in the electron density (FIG. 3).

Structural superposition of the individually refined protein chains from the crystal structures of apo-Tb7.14 and of the Tb7.N9 Y•DTPA-Tris complex with wild type hNGAL in complex with enterobactin shows that despite the large number of 16 amino acid exchanges the overall fold is extremely well conserved. In particular, the β-barrel itself, the short loops at its closed end, the α-helix attached to its side, and even the more or less flexible N- and C-terminal extensions of the polypeptide chain are almost indistinguishable (FIG. 3). The set of 58 Cα positions that are structurally conserved among the lipocalin family (Skerra (2000), supra), show r.m.s.d. values of 0.256, 0.440, 0.290, 0.371, and 0.386 Å, respectively, although the three proteins were crystallized in non-isomorphic space groups and, thus, with different crystal packing neighborhood.

Even more surprising, the set of four loops at the open end of the β-barrel, which harbors most of the side chain substitutions that were introduced to reshape the ligand pocket for the binding of DTPA have largely retained their geometry compared with the wild type protein. Especially loops #2, #3, and #4—connecting β-strands C/D, E/F, and G/H—exhibit an unchanged conformation; except for individual minor shifts of the loops as a whole. A maximum shift of ca. 1.2 Å is seen for the Cα position 73 at the tip of loop #2 in chain C of the apo-Tb7.14 structure, which is likely to reflect a crystal packing effect.

In contrast, the rather long a-type loop #1 shows considerable backbone flexibility among the three different crystal structures. Especially for chains A and C of the apo-Tb7.14 structure it is almost identical with wild type hNGAL in the region of residue 46, while significant deviations occur around residue 41. In the case of chain B, however, the entire segment between residues 40 and 49 is shifted by almost 5 Å (for the backbone). In case of the two chains of the Tb7.N9 DTPA complex this shift is even more severe and individually different, whereby there appears one turn of a $3_{10}$ helix around residue 44 for chain B. Notably, there is no electron density for residues 43-47 (chain A), 42-48 (chain B), and 43-47 (chain C) of this loop in the apo-Tb7.14 X-ray structure and this loop does not form crystal contacts in this structure as well as in the one of the DTPA complex. Hence, the conformation of loop #1 seems not only to be influenced both by the molecular environment but also by the presence of the metal chelate ligand. This behavior suggest that future mutational studies should be focused at loop #1 in order to achieve altered backbone conformations that lead to closer interaction with the bound DTPA ligand and, possibly, to even higher affinities.

Y•DTPA-Tris is bound more deeply than the natural ligand enterobactin at the bottom of the hNGAL cavity and almost situated in the mid among the 12 residues that were randomized in the original random library. The diethylenetriamino moiety interacts mainly with residues on β-strands C and D, whereby the cyclohexane ring packs against the hydrophobic residues Val66, Leu79, and Met81 while the benzyl side chain is sandwiched between Arg70 and Leu79 and protrudes with its Tris substituent into the solvent. The entire cavity is positively charged, similarly to wild type hNGAL (Goetz et al., supra), with the exception of the stretch of the residues Val111, Val121, and Phe123 at the bottom of the cavity. Notably, Met81 has replaced Arg71 in hNGAL, which is one of the three positively charged side chains that were described to participate in cation-π interactions with the bound enterobactin (Goetz et al., supra). Lys134 is replaced by Ser, thus providing space for the metal ion as well as two of the DTPA carboxylate groups and the liganding water molecule, and the more remote residue Lys125 may contribute to a general electrostatic interaction with the overall negatively charged metal chelate complex.

The larger side chain of residue Leu at position 79 compared with the one of Ala in the variant Tb7.14 leads to an improved van der Waals contact to the phenyl thiourea group of DTPA. The additional hydrogen bond between OG1 of the new side chain Thr80 (cf. Table 2) and OG1 of Thr67 locally stabilizes the pairing of strands C/D on the outside of the β-barrel. The buried surface area of the Y•DTPA-Tris amounts to 586 Å$^2$, which is about the same buried surface as for enterobactin bound to hNGAL.

Within a 4 Å radius altogether 15 residues are found in contact distance with the bound metal chelate complex, at least one in each of the eight β-strands: Gln33, Arg36, Thr52, Gln54, Val66, Ala68, Arg70, Asp77, Tyr78 (only via backbone), Leu79, Met81, Phe83, Tyr106, Phe123, and Thr136. Despite the smaller size of the ligand compared with enterobactin this is possible due to its deeper burial within the lipocalin cavity. On the other hand, there are rarely any contacts with the four loops. Among these residues, 9 positions were subject to mutagenesis in the initial hNGAL random library (cf. Table 2). The substitution Asp77Glu was found at a later stage of affinity maturation, whereas only four of the contacting side chains 66, 83, 106, and 123 correspond to original residues of hNGAL. Interestingly, they still exhibit the same rotamers in the Y•DTPA complex. Apart from these minor remnants, the mode of binding is totally different for the $Y^{3+}$•DTPA complex in the case of the engineered lipocalin than for $Fe^{3+}$•enterbactin by hNGAL.

Even though the two crystal structures were obtained for hNGAL variants at intermediate stages of the affinity maturation process, at least some of the additional mutations acquired on the way to our final variant C26 can be understood on their basis. The substitution Ile80Thr, which was repeatedly found in our screening experiments, occurs at a very critical position between Leu79 and Met81 mentioned above. Its side chain is displayed on the outside of the β-barrel and seems to be slightly shifted compared with the original residue in hNGAL and, thus, its replacement may affect a local change in the backbone geometry. The substitution Ser127Gln occurs at the tip of loop #4 and is quite remote from the bound ligand, which is in agreement with its marginal effect on the affinity (Table 3). Of the five additional side chain replacements that were identified for the variant C26 (42, 48, 49, 55, 75) three are located in loop #1, which may lead to a gross conformational change and bring this loop closer to the ligand. The side chain at position 55 occurs on the outside of the β-barrel, but, as in the case of position 80, an Ile residue is exchanged by Thr, which may have a similar effect mediated via the backbone on the neighboring Gln54, which contacts the DPTA ligand. Furthermore, the replacement of Lys75 by Met occurs at the tip of loop #2, at the last position of a stretch of three consecutive Lys residues and may hence influence the interaction with the side chain of the DTPA group.

Example 16

Generation of hNGAL Variants with Affinity to Hexachloronorbornene Hapten

The hNGAL library obtained in Example 2 was used to generate muteins having affinity to a hexachloronorbonene hapten. In more detail, the hexachloronorbornene hapten used was hexachloronorbornene N—$(CH_2)_5$—COOH the synthesis of which was reported by Hilvert et al., J. Am. Chem. Soc. 1989, Vol. 111, 9261-9262 (compound 2 in FIG. 1 of Hilvert et al) which represents a transition state analogue for the [4+2] Diels-Alder reaction (see also, Xu et al., Science, 1999, Vol. 286, 2345-2348). Generation of the hNGAL muteins were carried out essentially in accordance with the experimental procedure as described in Example 3 above and muteins with binding activity to the to hexachloronorbornene hapten were isolated and characterized by ELISA. In these ELISA experiments signals where obtained for selected hNGAL muteins indicating that muteins with at least micromolar $K_D$ were generated (data not shown). Also this data, even though being preliminary, show the suitability of the present invention to generate hNGAL muteins with antibody like properties (that means, for example, having binding affinity to any chosen hapten) by subjecting only the 12 amino acid residues 33, 36, 41, 52, 54, 68, 70, 79, 81, 134, 136 and 138 of the linear polypeptide sequence of hNGAL to mutagenesis.

Example 17

Affinity Maturation of the hNGAL Variant C26 Towards the Metal Chelate Complex, Y•p-NH$_2$-Bn-CHX-A"-DTPA via Phage Display and colony Screening To randomize loop 1 of the hNGAL variant C26 (SEQ ID NO:10), primers NGAL26 (SEQ ID NO:25; 5'-CCC AGG ACT CCA CCT CAG ACC-3') and L1Mback (SEQ ID NO:26; 5'-TGG GGC TGC ATT CCC TGC-3') were applied in a PCR with Taq DNA polymerase as above using pNGAL15-C26 plasmid DNA as template. A second PCR fragment was generated using primers L1Mfor (SEQ ID NO:27; 5'-GCA GGG AAT GCA GCT CCA NNS NNS NNS NNS NNS CTG CTA NNS NNS ACC GCC TAG ACT TAT GAG C-3') and P6 (SEQ ID NO:16). Both fragments were assembled using the flanking primers NGAL26 (SEQ ID NO:25) and P6 (SEQ ID NO:16). The PCR products were subcloned on pNGAL35 for phagemid display selection.

Phage display panning was performed as described in Example 3 but using competitive conditions and the Y•DTPA-RNase target adsorbed to ImmunoSticks. After washing 8 times, bound phagemids were incubated in the presence of a 400 μM solution of the free metal chelate complex, Y•p-NH$_2$-Bn-CHX-A"-DTPA, as competitor for 30 min in the first cycle, for 3 h in the second cycle, and for 24 h in the third cycle, followed by another three washing steps and, finally, acid elution. After three cycles of phagemid selection, the enriched pool of hNGAL variants was subcloned and subjected to the colony screening assay as in Example 3, again applying competitive conditions. Variants giving rise to intense staining signals in the presence of an approximately thousand-fold molar concentration of the unlabelled ligand were sequenced. In this manner the variant L1 (SEQ ID NO:28) was isolated, which exhibits six additional mutations as described in Table 4 (R43P/E44V/K46P/D47E/K50L/M51L).

The new hNGAL variant L1 was analyzed by SPR as in Example 8 using a Biacore CM-5 chip with the covalently attached Y-DTPA-RNaseA conjugate and applying the purified recombinant protein. The measured dissociation rate constant of $2.11 \times 10^{-4}$ s$^{-1}$ was improved by 3.4-fold, compared with the hNGAL variant C26, while the measured association rate constant of $2.96 \times 10^5$ M$^{-1}$ s$^{-1}$ was reduced by 10-fold, resulting in a K$_D$ of 713 pM.

Another randomization of the hNGAL variants was then performed by error-prone PCR using the plasmid DNA encoding C26 and L1, respectively, as template and primers P5 (SEQ ID NO:15) and P6 (SEQ ID NO:16) in the presence of 50 μM dPTP, 50 μM 8-oxo-dGTP, and 1 unit of 9° Nm DNA polymerase, followed by reamplification as described in Example 4. A 1:1 mixed phage display library with respect to the two templates was prepared and used for panning against the Y•DTPA-RNase target as above under competitive conditions. After three cycles of phagemid selection, the enriched pool of hNGAL variants was subcloned and subjected to the colony screening assay, again applying competitive conditions. 6 variants giving rise to intense staining signals were sequenced. All of these variants apparently were direct derivatives of L1 but not of C26. Among those, clone CL31 (SEQ ID NO:31) was isolated as the most promising hNGAL variant, exhibiting six additional mutations compared with L1 as listed in Table 4 (V44M/N65D/G86S/S87P/S99N/L107F).

Figure 2E:
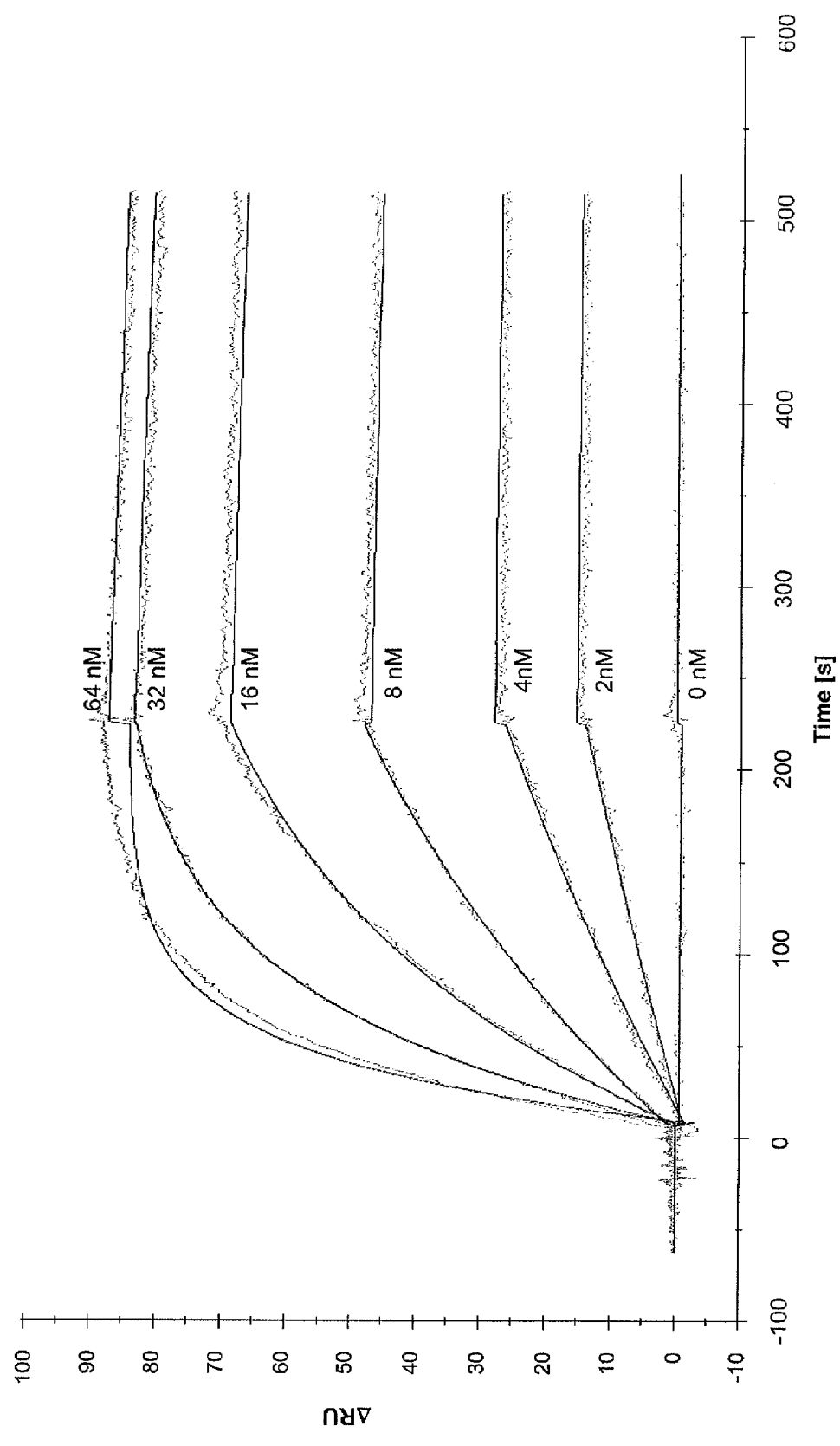
FIG. 2E depicts the kinetic real time analysis of hNGAL variant CL31 measured on a Biacore instrument at a flow rate of 25 μl/min. The Y•DTPA-RNase conjugate was coupled via amine chemistry to a CM5 sensor chip (ΔRU=300), and the purified hNGAL variant CL31 was applied at varying concentrations as indicated. The measured signal is shown as a gray line and the fitted curve as a black line in each case.

After preparation of the corresponding soluble protein and SPR analysis, the variant CL31 revealed clearly improved parameters with an association rate constant of $4.46 \times 10^5$ M$^{-1}$ s$^{-1}$, a dissociation rate constant of $1.06 \times 10^{-4}$ s$^{-1}$, and a 237 pM affinity to the metal chelate ligand (FIG. 2E). Thus, after complex formation CL31 shows a significantly longer half life of dissociation (ca. 1.8 h) over the parental lipocalin mutein C26 (16 min). The other selected variants showed a similar binding activity (data not shown).

TABLE 4

Amino acid positions of selected hNGAL variants that differ from the sequence of C26. C26 carries additional substitutions compared with wild-type hNGAL as detailed in Table 2.

| Residue No.$^a$ | C26 (SEQ ID NO: 10) | L1 (SEQ ID NO: 28) | CL2 (SEQ ID NO: 29) | CL27 (SEQ ID NO: 30) | CL31 (SEQ ID NO: 31) | CL34 (SEQ ID NO: 32) | CL63 (SEQ ID NO: 33) | CL97 (SEQ ID NO: 34) |
|---|---|---|---|---|---|---|---|---|
| 43 | Arg | Pro | Pro | Pro | Pro | Pro | Pro | Pro |
| 44 | Glu | Val | Val | Val | Met | Val | Val | Val |
| 46 | Lys | Pro | Pro | Pro | Pro | Pro | Pro | Pro |
| 47 | Asp | Glu | Glu | Glu | Glu | Glu | Glu | Glu |
| 50 | Lys | Leu | Leu | Leu | Leu | Leu | Leu | Leu |
| 51 | Met | Leu | Leu | Leu | Leu | Leu | Leu | Leu |
| 59 | Lys | Lys | Lys | Lys | Lys | Arg | Lys | Lys |
| 65 | Asn | Asn | Asp | Asp | Asp | Asp | Asp | Asn |
| 78 | Tyr | Tyr | Tyr | Tyr | Tyr | Tyr | Tyr | His |
| 86 | Gly | Gly | Gly | Ser | Ser | Gly | Gly | Gly |
| 87 | Ser | Ser | Ser | Ser | Pro | Ser | Phe | Ser |
| 98 | Lys | Lys | Glu | Lys | Lys | Lys | Lys | Lys |
| 99 | Ser | Ser | Ser | Ser | Asn | Ser | Ser | Ser |
| 103 | Leu | Leu | Leu | Leu | Leu | Leu | Leu | Ile |
| 107 | Leu | Leu | Leu | Leu | Phe | Leu | Leu | Phe |
| 110 | Val | Val | Met | Val | Val | Val | Val | Val |
| 111 | Val | Val | Val | Val | Val | Val | Val | Ala |

$^a$Sequential numbering of the mature protein sequence (cf. SwissProt entry P80188).

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention. The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group. Further embodiments of the invention will become apparent from the following claims.

What is claimed is:

1. A mutein derived from human neutrophil gelatinase-associated lipocalin (hNGAL), said mutein comprising at least 4 mutated amino acid residues at any of the sequence positions corresponding to the sequence positions 33, 36, 41, 52, 54, 68, 70, 79, 81, 134, 136 and 138 of the linear polypeptide sequence of hNGAL (SEQ ID NO: 1), and wherein the mutein binds a given target with detectable affinity.

2. The mutein of claim 1, wherein the mutein comprises mutated amino acid residues in at least 5, at least 6 or at least 7 of amino acid residues at any of the sequence positions corresponding to the sequence positions 33, 36, 41, 52, 54, 68, 70, 79, 81, 134, 136 and 138 of the linear polypeptide sequence of hNGAL.

3. The mutein of claim 1, wherein the mutein comprises mutated amino acid residues in at least 8 at least 10 or all 12 of amino acid residues at any of the sequence positions corresponding to the sequence positions 33, 36, 41, 52, 54, 68, 70, 79, 81, 134, 136 and 138 of the linear polypeptide sequence of hNGAL.

4. The mutein of claim 1, which has an amino acid sequence further differing from the linear polypeptide sequence of hNGAL (SEQ ID NO: 1) by at least one mutated amino acid residue at any of the sequence positions corresponding to the sequence positions 42, 48, 49, 55, 75, 77, 80 and 127 of the linear polypeptide sequence of hNGAL.

5. The mutein of claim 4, wherein the mutein comprises at least 5 mutated amino acid residues at any of the sequence positions corresponding to the sequence positions 33, 36, 41, 42, 48, 49, 52, 54, 55, 68, 70, 75, 77, 79, 80, 81, 127, 134, 136 and 138 of the linear polypeptide sequence of hNGAL.

6. The mutein of claim 5, wherein the mutein comprises mutated amino acid residues at least any 16, 17, 18, 19 or all 20 of said sequence positions.

7. The mutein of claim 1, which has an amino acid sequence further differing from the linear polypeptide sequence of hNGAL (SEQ ID NO: 1) by at least one mutated amino acid residue at any of the sequence positions corresponding to the sequence positions 43, 44, 46, 47, 50, 51, 59, 65, 78, 86, 87, 98, 99, 103, 107, 110 and 111 of the linear polypeptide sequence of hNGAL.

8. The mutein of claim 7, wherein the mutein comprises at least 5 mutated amino acid residues at any of the sequence positions corresponding to the sequence positions 33, 36, 41, 42, 43, 44, 46, 47, 48, 49, 50, 51, 52, 54, 55, 59, 65, 68, 70, 75, 77, 78, 79, 80, 81, 86, 87, 98, 99, 103, 107, 110, 111, 127, 134, 136 and 138 of the linear polypeptide sequence of hNGAL.

9. The mutein of claim 8, wherein the mutein comprises mutated amino acid residues at at least any 22, 24, 26, 28, 29, 30, 31, 32, 33, 35 or all 37 of said sequence positions.

10. The mutein of claim 1, wherein the mutein comprises mutated amino acid residues at at least any 7 of said sequence positions.

11. The mutein of claim 1, wherein the mutein comprises mutated amino acid residues at at least any 10 of said sequence positions.

12. The mutein of claim 11, wherein the mutein comprises mutated amino acid residues at at least any 14 or 15 of said sequence positions.

13. The mutein of claim 1, wherein the mutein further comprises one or more of the amino acid replacements selected from the group consisting of Glu28→His, Cys87→Ser, and Thr145→Ala.

14. The mutein of claim 1, wherein a Cys residue is introduced at at least one of the sequence positions that correspond to sequence positions 14, 21, 60, 84, 88, 116, 141, 145, 143, 146 or 158 of the wild type sequence of hNGAL.

15. The mutein of claim 1, wherein the mutein comprises with respect to the linear polypeptide sequence of hNGAL amino acid sequence additional amino acid replacements at at least one of the sequence positions that correspond to sequence positions 65, 71, 73, 74, 116, 125 and 135 of the linear polypeptide sequence of hNGAL.

16. The mutein of claim 1, wherein the mutein binds a small organic molecule or a peptide.

17. The mutein of claim 16, wherein the small organic molecule is a metal chelating agent or a pharmaceutical agent.

18. The mutein of claim 17, wherein the small organic molecule is diethylenetriamine pentaacetic acid (DPTA), 1,4,7,10-tetra-azacylcododecane-N,N',N'',N'''-tetraacetic acid (DOTA) or a derivative thereof.

19. The mutein of claim 18, wherein the DPTA, DOTA, or derivative thereof is complexed with a metal ion.

20. The mutein of claim 19, wherein the metal is selected from the group consisting of yttrium (Y), terbium (Tb), indium (In), lutetium (Lu) and bismuth (Bi).

21. The mutein of claim 18, wherein the DTPA derivative is cyclohexyl-DTPA.

22. The mutein of claim 21, wherein the mutein binds cyclohexyl-DTPA with a KD of 50 nM or less.

23. The mutein of claim 21, wherein the mutein has an amino acid sequence selected from the group consisting of the sequences set forth in SEQ ID NOs. 2-10 and 28-34.

24. The mutein of claim 1, wherein the mutein comprises with respect to the linear polypeptide sequence of hNGAL at least 3, 4, 5, 6, 7, 8, 9, 10, 11, or 12 amino acid replacements selected from the group consisting of Val33→Gln; Leu36→Arg; Ile41→Ala; Tyr52→Thr; Thr54→Gln; Ser68→Ala; Leu70→Arg; Trp79→Ala, Leu; Arg81→Met; Lys134→Ser; Thr136→Ser; and Tyr138→Leu.

25. The mutein of claim 24, wherein the mutein comprises with respect to the linear polypeptide sequence of hNGAL the amino acid replacements:
(a) Val33→Gln; Leu36→Arg; Ile41→Ala; Tyr52→Thr; Thr54→Gln; Ser68→Ala; Leu70→Arg; Trp79→Ala; Arg81→Met; Lys134→Ser; and Tyr138→Leu;
(b) Val33→Gln; Leu36→Arg; Ile41→Ala; Tyr52→Thr; Thr54→Gln; Ser68→Ala; Leu70→Arg; Trp79→Leu; Arg81→Met; Lys134→Ser; and Tyr138→Leu; or
(c) Val33→Gln; Leu36→Arg; Ile41→Ala; Tyr52→Thr; Thr54→Gln; Ser68→Ala; Leu70→Arg; Trp79→Leu; Arg81→Met; Lys134→Ser; Thr136→Ser; and Tyr138→Leu.

26. The mutein of claim 25, wherein the mutein further comprises with respect to the-linear polypeptide sequence of hNGAL an amino acid replacement selected from the group consisting of Glu28→His, Cys87→Ser, and Thr145→Ala.

27. The mutein of claim 24, wherein the mutein further comprises with respect to the linear polypeptide sequence of hNGAL an amino acid replacement selected from the group consisting of Leu42→Pro, Pro48→Leu, Gln49→Leu, Ile55→Thr, Lys75→Met, Asp77→Glu, Ile80→Thr, and Ser127→Gln.

28. The mutein of claim 27, wherein the mutein comprises with respect to the linear polypeptide sequence of hNGAL the amino acid replacements:
(a). Val33→Gln; Leu36→Arg; Ile41→Ala; Tyr52→Thr; Thr54→Gln; Ser68→Ala; Leu70→Arg; Trp79→Ala; Ile 80→Thr; Arg81→Met; Lys134→Ser; and Tyr138→Leu;
(b). Val33→Gln; Leu36→Arg; Ile41→Ala; Tyr52→Thr; Thr54→Gln; Ser68→Ala; Leu70→Arg; Trp79→Leu; Ile 80→Thr; Arg81→Met; Lys134→Ser; and Tyr138→Leu;
(c). Val33→Gln; Leu36→Arg; Ile41→Ala; Tyr52→Thr; Thr54→Gln; Ser68→Ala; Leu70→Arg; Trp79→Leu; Ile 80→Thr; Arg81→Met; Ser127→Gln; Lys134→Ser; and Tyr138→Leu;
(d). Val33→Gln; Leu36→Arg; Ile41→Ala; Tyr52→Thr; Thr54→Gln; Ser68→Ala; Leu70→Arg; Trp79→Leu; Ile 80→Thr; Arg81→Met; Lys134→Ser; Thr136→Ser; and Tyr138→Leu;
(e). Val33→Gln; Leu36→Arg; Ile41→Ala; Tyr52→Thr; Thr54→Gln; Ser68→Ala; Leu70→Arg; Trp79→Leu; Ile 80→Thr; Arg81→Met; Ser127→Gln; Lys134→Ser; Thr136→Ser; and Tyr138→Leu;
(f). Val33→Gln; Leu36→Arg; Ile41→Ala; Tyr52→Thr; Thr54→Gln; Ser68→Ala; Leu70→Arg; Asp77→Glu; Trp79→Leu; Ile 80→Thr; Arg81→Met; Ser127→Gln; Lys134→Ser; Thr136→Ser; and Tyr138→Leu;
(g). Val33→Gln; Leu36→Arg; Ile41→Ala; Leu42→Pro; Pro48→Leu; Gln49→Leu; Tyr52→Thr; Thr54→Gln; Ile55→Thr; Ser68→Ala; Leu70→Arg; Lys75→Met; Asp77→Glu; Trp79→Leu; Ile 80→Thr; Arg81→Met; Ser127→Gln; Lys134→Ser; Thr136→Ser; and Tyr138→Leu;
(h). Val33→Gln; Leu36→Arg; Ile41→Ala; Leu42→Pro; Arg43→Pro; Glu44→Val; Lys46→Pro; Asp47→Glu; Pro48→Leu; Gln49→Leu; Lys50→Leu; Met51→Leu; Tyr52→Thr; Thr54→Gln; Ile55→Thr; Ser68→Ala; Leu70→Arg; Lys75→Met; Asp77→Glu; Trp79→Leu; Ile80→Thr; Arg81→Met; Ser127→Gln; Lys134→Ser; Thr136→Ser; and Tyr138→Leu;
(i). Val33→Gln; Leu36→Arg; Ile41→Ala; Leu42→Pro; Arg43→Pro; Glu44→Val; Lys46→Pro; Asp47→Glu;

Pro48→Leu; Gln49→Leu; Lys50→Leu; Met51→Leu; Tyr52→Thr; Thr54→Gln; Ile55→Thr; Asn65→Asp; Ser68→Ala; Leu70→Arg; Lys75→Met; Asp77→Glu; Trp79→Leu; Ile 80→Thr; Arg81→Met; Lys98→Glu; Val110→Met; Ser127→Gln; Lys134→Ser; Thr136→Ser; and Tyr138→Leu;

(j). Val33→Gln; Leu36→Arg; Ile41→Ala; Leu42→Pro; Arg43→Pro; Glu44→Val; Lys46→Pro; Asp47→Glu; Pro48→Leu; Gln49→Leu; Lys50→Leu; Met51→Leu; Tyr52→Thr; Thr54→Gln; Ile55→Thr; Asn65→Asp; Ser68→Ala; Leu70→Arg; Lys75→Met; Asp77→Glu; Trp79→Leu; Ile 80→Thr; Arg81→Met; Gly86→Ser; Ser127→Gln; Lys134→Ser; Thr136→Ser; and Tyr138→Leu;

(k). Val33→Gln; Leu36→Arg; Ile41→Ala; Leu42→Pro; Arg43→Pro; Glu44→Met; Lys46→Pro; Asp47→Glu; Pro48→Leu; Gln49→Leu; Lys50→Leu; Met51→Leu; Tyr52→Thr; Thr54→Gln; Ile55→Thr; Asn65→Asp; Ser68→Ala; Leu70→Arg; Lys75→Met; Asp77→Glu; Trp79→Leu; Ile 80→Thr; Arg81→Met; Gly86→Ser; Ser87→Pro; Ser99→Asn; Leu107→Phe; Ser127→Gln; Lys134→Ser; Thr136→Ser; and Tyr138→Leu;

(l). Val33→Gln; Leu36→Arg; Ile41→Ala; Leu42→Pro; Arg43→Pro; Glu44→Val; Lys46→Pro; Asp47→Glu; Pro48→Leu; Gln49→Leu; Lys50→Leu; Met51→Leu; Tyr52→Thr; Thr54→Gln; Ile55→Thr; Lys59→Arg; Asn65→Asp; Ser68→Ala; Leu70→Arg; Lys75→Met; Asp77→Glu; Trp79→Leu; Ile 80→Thr; Arg81→Met; Ser127→Gln; Lys134→Ser; Thr136→Ser; and Tyr138→Leu;

(m). Val33→Gln; Leu36→Arg; Ile41→Ala; Leu42→Pro; Arg43→Pro; Glu44→Val; Lys46→Pro; Asp47→Glu; Pro48→Leu; Gln49→Leu; Lys50→Leu; Met51→Leu; Tyr52→Thr; Thr54→Gln; Ile55→Thr; Asn65→Asp; Ser68→Ala; Leu70→Arg; Lys75→Met; Asp77→Glu; Trp79→Leu; Ile 80→Thr; Arg81→Met; Ser87→Phe; Ser127→Gln; Lys134→Ser; Thr136→Ser; and Tyr138→Leu; or (n). Val33→Gln; Leu36→Arg; Ile41→Ala; Leu42→Pro; Arg43→Pro; Glu44→Val; Lys46→Pro; Asp47→Glu; Pro48→Leu; Gln49→Leu; Lys50→Leu; Met51→Leu; Tyr52→Thr; Thr54→Gln; Ile55→Thr; Ser68→Ala; Leu70→Arg; Lys75→Met; Asp77→Glu; Tyr78→His; Trp79→Leu; Ile 80→Thr; Arg81→Met; Leu103→Ile; Leu107→Phe; Val111→Ala; Ser127→Gln; Lys134→Ser; Thr136→Ser; and Tyr138→Leu.

29. The mutein of claim 24, wherein the mutein further comprises with respect to the linear polypeptide sequence of hNGAL an amino acid replacement selected from the group consisting of Arg43→Pro, Glu44→Val, Glu44→Met, Lys46→Pro, Asp47→Glu, Lys50→Leu, Met51→Leu, Lys59→Arg, Asn65→Asp, Tyr78→His, Gly86→Ser, Ser87→Pro, Ser87→Phe, Lys98→Glu, Ser99→Asn, Leu103→Ile, Leu107→Phe, Val110→Met, and Val111→Ala.

30. The mutein of claim 1, wherein the mutein is conjugated to a targeting moiety with binding affinity for a chosen target molecule, wherein said targeting moiety targets a specific body region in a mammal.

31. The mutein according to claim 30, wherein the targeting moiety is selected from the group consisting of an antibody, an antibody fragment, a lipocalin mutein, and a lipocalin mutein fragment.

32. The mutein of claim 1, wherein the mutein is conjugated to a label selected from the group consisting of organic molecules, enzyme labels, radioactive labels, colored labels, fluorescent labels, chromogenic labels, luminescent labels, haptens, digoxigenin, biotin, metal complexes, metals, and colloidal gold.

33. The mutein of claim 1, wherein the mutein is fused at its N-terminus and/or its C-terminus to a protein, a protein domain or a peptide.

34. The mutein of claim 33, wherein the protein domain extends the serum half-life of the mutein.

35. The mutein of claim 34, wherein the protein domain is a Fc part of an immunoglobulin, a CH3 domain of an immunoglobulin, a CH4 domain of an immunoglobulin, an albumin binding peptide, or an albumin binding protein.

36. The mutein of claim 1, wherein the mutein is conjugated to a moiety that extends the serum half-life of the mutein.

37. The mutein of claim 36, wherein the moiety that extends the serum half-life is selected from the group consisting of a polyalkylene glycol molecule, hydroxyethyl-starch, a Fc part of an immunoglobulin, a CH3 domain of an immunoglobulin, a CH4 domain of an immunoglobulin, an albumin binding peptide, and an albumin binding protein.

38. The mutein of claim 37, wherein the polyalkylene glycol is polyethylene (PEG) or an activated derivative thereof.

39. The mutein of claim 37, wherein the albumin binding protein is a bacterial albumin domain or a lipocalin mutein.

40. The mutein of claim 39, wherein the bacterial albumin binding domain is the albumin binding domain of streptococcal protein G.

41. The mutein of claim 37, wherein the albumin binding peptide has the formula Cys-Xaa1-Xaa2-Xaa3-Xaa4-Cys, wherein Xaa1 is Asp, Asn, Ser, Thr, or Trp; Xaa2 is Asn, Gln, His, Ile, Leu, or Lys; Xaa3 is Ala, Asp, Phe, Trp, or Tyr; and Xaa4 is Asp, Gly, Leu, Phe, Ser, or Thr.

42. An isolated nucleic acid molecule encoding a mutein of claim 1.

43. The isolated nucleic acid molecule of claim 42, wherein the nucleic acid molecule is operably linked to a regulatory sequence.

44. The isolated nucleic acid molecule of claim 42 comprised in a vector.

45. The isolated nucleic acid molecule of claim 42 comprised in a phagemid vector.

46. A host cell containing the nucleic acid molecule of claim 42.

47. A method for the generation of a mutein of claim 1, comprising:

(a) subjecting a nucleic acid molecule encoding an hNGAL protein to mutagenesis at a nucleotide triplet coding for at least 9 of any of the sequence positions corresponding to the sequence positions 33, 36, 41, 52, 54, 68, 70, 79, 81, 134, 136, and 138 of the linear polypeptide sequence of hNGAL (SEQ ID NO: 1), resulting in one or more mutein nucleic acid molecule(s), (b) expressing the one more mutein nucleic acid molecule (s) obtained in (a) in an isolated host cell, and (c) identifying one or mutein nucleic acid molecules encoding a mutein having a detectable binding affinity for a given target by means of selection and/or isolation.

48. The method of claim 47, further comprising subjecting the nucleic acid molecule to mutagenesis in at least 10, 11 or all 12 of the nucleotide triplets coding for sequences corresponding to amino acid positions 33, 36, 41, 52, 54, 68, 70, 79, 81, 134, 136, and 138 of the linear polypeptide sequence of hNGAL (SEQ ID NO: 1).

49. The method of claim 47, further comprising subjecting the nucleic acid molecule to mutagenesis in at least one nucleotide triplet coding for a sequence positions corresponding to amino acid positions 42, 48, 49, 55, 75, 77, 80, and 127 of the linear polypeptide sequence of hNGAL (SEQ ID NO: 1).

50. The method of claim 49, further comprising subjecting the nucleic acid molecule to mutagenesis at nucleotide triplets coding for at least any 9 of the sequence positions corresponding to the amino acid positions 33, 36, 41, 42, 48, 49, 52, 54, 55, 68, 70, 75, 77, 79, 80, 81, 127, 134, 136 and 138 of the linear polypeptide sequence of hNGAL (SEQ ID NO: 1).

51. The method of claim 47, further comprising subjecting the nucleic acid molecule to mutagenesis in at least one nucleotide triplet coding for any of the sequence positions corresponding to amino acid positions 43, 44, 46, 47, 50, 51, 59, 65, 78, 86, 87, 98, 99, 103, 107, 110 and 111 of the linear polypeptide sequence of hNGAL (SEQ ID NO: 1).

52. The method of claim 51, further comprising subjecting the nucleic acid molecule to mutagenesis at nucleotide triplets coding for at least any 9 of the sequence positions corresponding to the amino acid positions 33, 36, 41, 42, 43, 44, 46, 47, 48, 49, 50, 51, 52, 54, 55, 59, 65, 68, 70, 75, 77, 78, 79, 80, 81, 86, 87, 98, 99, 103, 107, 110, 111, 127, 134, 136 and 138 of the linear polypeptide sequence of hNGAL (SEQ ID NO: 1).

53. The mutein of claim 1, which is recombinantly expressed.

54. The mutein of claim 53, wherein the mutein is recombinantly expressed in a bacterial or eucaryotic host organism and is isolated from the host organism or its culture.

55. A pharmaceutical composition comprising the mutein of claim 1 and a pharmaceutically acceptable excipient.

56. A diagnostic or analytical kit comprising the mutein of claim 1 in a container, optionally containing instructions for its use.

57. A method for radio immuno therapy (RIT) in a mammal comprising (a) radiolabeling the mutein of claim 1, and (b) administering to said mammal an effective amount of the radiolabeled mutein.

58. A method for in vivo imaging in a mammal comprising (a) radiolabeling the mutein of claim 1, (b) administering to said mammal an effective amount of the radiolabeled mutein and (c) imaging the mammal.

59. The mutein of claim 1, further comprising a Cys residue in at least one of any of the sequence positions that correspond to amino acid positions 14, 21, 60, 84, 88, 116, 141, 145, 143, 146 or 158 of the wild type sequence of hNGAL and which is coupled to via the thiol group of a Cys residue to a moiety that is able to modify the serum half-life of said protein.

60. The mutein of claim 59, wherein the moiety that is able to modify the serum half-life is selected from the group consisting of a polyalkylene glycol molecule and hydroxyethylstarch.

61. The mutein of claim 1, wherein the mutein binds the given target with a KD of 1 µM or less, 100 µM or less, 1 µM or less, 500 nM, 200 nM or less, 100, nM or less, 50 nM or less, 10 nM or less, or 1 nM or less.

* * * * *

UNITED STATES PATENT AND TRADEMARK OFFICE
CERTIFICATE OF CORRECTION

PATENT NO. : 8,420,051 B2  Page 1 of 1
APPLICATION NO. : 12/737240
DATED : April 16, 2013
INVENTOR(S) : Skerra et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 109 days.

Signed and Sealed this
First Day of September, 2015

Michelle K. Lee
*Director of the United States Patent and Trademark Office*